(12) United States Patent
Florjancic et al.

(10) Patent No.: US 9,346,813 B2
(45) Date of Patent: May 24, 2016

(54) SUBSTITUTED PYRROLO[2,3-D]PYRIMINDINES AS CDK9 KINASE INHIBITORS

(71) Applicant: AbbVie Inc., North Chicago, IL (US)

(72) Inventors: Alan S. Florjancic, Kenosha, WI (US); Yunsong Tong, Libertyville, IL (US); Thomas D. Penning, Elmhurst, IL (US); Andrew J. Souers, Libertyville, IL (US); Rajeev Goswami, Dehradun (IN); Zhi-Fu Tao, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/207,868

(22) Filed: Mar. 13, 2014

(65) Prior Publication Data

US 2014/0275004 A1    Sep. 18, 2014

(51) Int. Cl.
*A61K 31/519*     (2006.01)
*C07D 239/70*     (2006.01)
*C07D 487/04*     (2006.01)

(52) U.S. Cl.
CPC ............ *C07D 487/04* (2013.01); *A61K 31/519* (2013.01)

(58) Field of Classification Search
CPC ..................... A61K 31/519; C07D 239/70
USPC ............. 514/265.1; 544/280; 546/268.1; 548/364.7, 517, 950; 549/356, 429
See application file for complete search history.

(56) References Cited

FOREIGN PATENT DOCUMENTS

| WO | 03/000695 | 1/2003 |
|---|---|---|
| WO | 2006/017443 | 2/2006 |
| WO | 2008079918 | 7/2008 |
| WO | 2008/128072 | 10/2008 |
| WO | 2008145688 | 12/2008 |
| WO | 2010003133 | 1/2010 |
| WO | 2010/020675 | 2/2010 |
| WO | 2013/157021 | 10/2013 |
| WO | WO 2014/160028 | * 10/2014 |

OTHER PUBLICATIONS

Jordan, V. C. Nature Reviews: Drug Discovery, 2, 2003, 205.*
Hackam, et al. JAMA, 296(14), 2006, 1731-1732.*
The International Search Report and Written Opinion for PCT/US2014/025740 mailed May 27, 2014.
The International Search Report and Written Opinion for PCT/US2014/025670 mailed May 22, 2014.

* cited by examiner

*Primary Examiner* — Douglas M Willis
(74) *Attorney, Agent, or Firm* — Changxia Sun

(57) ABSTRACT

Disclosed are compound of Formula (Ia),

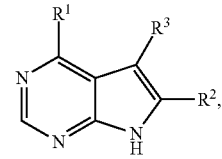

wherein $R^1$, $R^2$, and $R^3$ are as defined in the specification, and pharmaceutically acceptable salts thereof. The compounds may be used as agents in the treatment of diseases, including cancer. Also provided are pharmaceutical compositions, comprising one or more compounds of Formula (Ia).

16 Claims, No Drawings

SUBSTITUTED PYRROLO[2,3-D]PYRIMINDINES AS CDK9 KINASE INHIBITORS

BACKGROUND OF THE INVENTION

Cyclin-dependent kinases (CDKs) are serine/threonine protein kinases whose activity depends on binding and activation by cyclin partners. These heterodimeric complexes can phosphorylate various substrates involved in the control of transcription and cell-cycle progression in response to different stimuli. CDK8 and CDK9 have key roles in the control of transcription by RNA polymerase II. CDK9 responds specifically to several cytokines, including tumor necrosis factor and interleukin-6, indicating that it might have special roles in the regulation of a variety of physiological processes, especially immune responses, inflammation, cell activation, and differentiation.

Deregulated CDK activity is a hallmark of human cancer, and a variety of genetic and epigenetic events, such as over expression of cyclins, diminished levels of CDK inhibiting proteins or gain- of function mutations in CDK, have been described to cause increased activity of these enzymes and provide a selective growth advantage in tumor cells. CDK9 inhibition causes rapid depletion of short-lived mRNA transcripts and their associated protein products. Many genes encoding proteins involved in cell growth, proliferation, and tumor development (Myc, Cyclin D1, and Mcl-1) are characterized by short-lived mRNAs and proteins and hence the consequences of CDK9 inhibition include anti-proliferative and pro-apoptotic effects through loss of function at many cellular pathways. Tumor types that are dependent on labile pro-survival proteins (e.g., Mcl-1), which includes multiple myeloma, CLL, breast, melanoma and pancreatic cancers as well as the MYC-driven tumors (multiple cancer types) would be susceptible to CDK9 inhibition. CDK9 inhibitors might also be effective in combination with standard of care in tumors in which NF-κB is constitutively active and contributing to chemo resistance. This includes hematologic malignancies as well as solid tumors (breast, colorectal, prostate, melanoma and pancreatic). Thus, CDK9 inhibition targets multiple cancer-relevant pathways by inhibition of a single protein and thereby renders CDK9 as an attractive target for anti-cancer therapy. (Nature Reviews Cancer: 2009, 9, 153-166).

CDK9 inhibitors can also find therapeutic application in cardiology and virology as many viruses depend on the infected host for transcription of their genome. (Cyclin-dependent kinase 9: a key transcriptional regulator and potential drug target in oncology, virology and cardiology. Trends in Pharmacol. Sci. 2009, 29. 302-312; Pharmacological targeting of CDK9 in cardiac hypertrophy. Med Res. Rev. 2010 30:646-66; Novel HIV-1 therapeutics through targeting altered host cell pathways. Expert Opin Biol Ther. 2009 9:1369-82).

CDK9 inhibitors have also been reported as potential therapeutics for the treatment of chronic, inflammatory and neuropathic pain (WO2008/049856; WO2009/047359).

In view of the above, there is a need in the art for small molecule therapeutics that can inhibit the activity of CDK9. The present invention fulfills at least this need.

SUMMARY OF THE INVENTION

In one aspect, the present invention relates to compounds of Formula (Ia) or a pharmaceutically acceptable salt thereof,

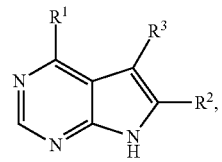

(Ia)

wherein
$R^1$ is selected from the group consisting of phenyl, 5 to 6 membered heteroaryl, 4 to 7 membered heterocycloalkyl and 4 to 7 membered heterocycloalkenyl; wherein the $R^1$ phenyl, 5 to 6 membered heteroaryl, 4 to 7 membered heterocycloalkyl and 4 to 7 membered heterocycloalkenyl are optionally substituted with one or more substituents selected from the group consisting of $R^{1A}$, $OR^{1A}$, $NHSO_2R^{1A}$, halo, CN, and $NHR^{1A}$;

$R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, C(O)OH, and $C(O)OR^{17}$;

$R^2$ is selected from the group consisting of cycloalkyl, cycloalkenyl, heterocycloalkyl and heterocycloalkenyl; wherein the $R^2$ cycloalkyl, cycloalkenyl, heterocycloalkyl and heterocycloalkenyl are optionally substituted with one or more $R^{2A}$;

$R^{2A}$, at each occurrence, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, C(O)OH, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, 4 to 7 membered heterocycloalkenyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}(O)R^{10}$, $NR^{11}C(O)R^{10}$, $NHS(O)_2R^9$, $NR^{11}S(O)_2R^9$, NHC(O)$NH_2$, $NHC(O)NHR^{11}$, $NHC(O)NR^{11}R^{12}$, $NR^{11}C(O)NHR^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, C(O)OH, OH, CN, and halo;

$R^3$ is selected from the group consisting of hydrogen, $C_1$-$C_4$ alkyl, $NO_2$, CN, F, Cl, Br and I;

$R^4$, at each occurrence, is independently selected from the group consisting of $C_1$-$C_5$ alkyl, $C_1$-$C_5$ alkenyl, aryl, 5 to 6 membered heteroaryl, 4 to 7 membered heterocycloalkyl, and $C_3$-$C_7$ cycloalkyl; wherein the $R^4C_1$-$C_5$ alkyl and $C_1$-$C_5$ alkenyl are optionally substituted with one or more substituents selected from the group consisting of halo, $C_1$-$C_3$-haloalkyl, C(O)OH, CN, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, C(O)OH, CN, NH$_2$, NHSO$_2$R$^{17}$; NHC(O)R$^{17}$, C(O)R$^{17}$, C(O)OR$^{17}$, and NHC(O)OR$^{17}$;

R$^5$, R$^6$, R$^7$, R$^8$, R$^9$, R$^{10}$, R$^{11}$, R$^{12}$, R$^{13}$, R$^{14}$, R$^{15}$, R$^{16}$, and R$^{17}$, at each occurrence, are independently selected from the group consisting of C$_1$-C$_6$ alkyl, C$_1$-C$_3$-haloalkyl, C$_2$-C$_5$ alkenyl, aryl, 5 to 6 membered heteroaryl, 4 to 7 membered heterocycloalkyl, and C$_3$-C$_7$ cycloalkyl; wherein the R$^5$, R$^6$, R$^7$, R$^8$, R$^9$, R$^{10}$, R$^{11}$, R$^{12}$, R$^{13}$, R$^{14}$, R$^{15}$, R$^{16}$, and R$^{17}$C$_1$-C$_6$ alkyl, C$_1$-C$_3$-haloalkyl, C$_2$-C$_5$ alkenyl, aryl, 5 to 6 membered heteroaryl, 4 to 7 membered heterocycloalkyl, and C$_3$-C$_7$ cycloalkyl are optionally substituted with one or more substituents selected from the group consisting of C$_1$-C$_6$ alkyl, C$_3$-C$_7$ cycloalkyl, (O), OH, C(O)OR$^{18}$, OR$^{18}$, and C(O)OH; and R$^{18}$, at each occurrence, is C$_1$-C$_6$ alkyl.

In one embodiment of Formula (Ia), R$^3$ is H. In another embodiment of Formula (Ia), R$^3$ is H; and R$^1$ is phenyl; wherein the R$^1$ phenyl is optionally substituted with one or more substituents selected from the group consisting of R$^{1A}$, OR$^{1A}$, NHSO$_2$R$^{1A}$, halo, and NHR$^{1A}$. In another embodiment of Formula (Ia), R$^3$ is H; and R$^1$ is 5 to 6 membered heteroaryl; wherein the R$^1$ 5 to 6 membered heteroaryl is optionally substituted with one or more substituents selected from the group consisting of R$^{1A}$, OR$^{1A}$, NHSO$_2$R$^{1A}$, halo, and NHR$^{1A}$. In another embodiment of Formula (Ia), R$^3$ is H; and R$^1$ is 4 to 7 membered heterocycloalkyl; wherein the R$^1$ 4 to 7 membered heterocycloalkyl is optionally substituted with one or more substituents selected from the group consisting of R$^{1A}$, OR$^{1A}$, NHSO$_2$R$^{1A}$, halo, and NHR$^{1A}$. In another embodiment of Formula (Ia), R$^3$ is H; R$^1$ is phenyl; wherein the R$^1$ phenyl is optionally substituted with one or more substituents selected from the group consisting of R$^{1A}$, OR$^{1A}$, NHSO$_2$R$^{1A}$, halo, and NHR$^{1A}$; and R$^{1A}$, at each occurrence, is independently selected from the group consisting of C$_1$-C$_3$-haloalkyl, O—C$_1$-C$_3$-haloalkyl, C$_1$-C$_6$-alkyl, C$_1$-C$_3$ alkylene-phenyl, C$_1$-C$_3$ alkylene-(5 to 6 membered heteroaryl), and C$_1$-C$_3$ alkylene-(4 to 7 membered heterocycloalkyl); wherein the R$^{1A}$ phenyl, 5 to 6 membered heteroaryl, and 4 to 7 membered heterocycloalkyl rings are optionally substituted with CN. In another embodiment of Formula (Ia), R$^3$ is H; R$^1$ is 5 to 6 membered heteroaryl; wherein the R$^1$ 5 to 6 membered heteroaryl is optionally substituted with one or more substituents selected from the group consisting of R$^{1A}$, OR$^{1A}$, NHSO$_2$R$^{1A}$, halo, and NHR$^{1A}$; and R$^{1A}$, at each occurrence, is independently selected from the group consisting of C$_1$-C$_3$-haloalkyl, O—C$_1$-C$_3$-haloalkyl, C$_1$-C$_6$-alkyl, C$_1$-C$_3$ alkylene-phenyl, C$_1$-C$_3$ alkylene-(5 to 6 membered heteroaryl), and C$_1$-C$_3$ alkylene-(4 to 7 membered heterocycloalkyl); wherein the R$^{1A}$ phenyl, 5 to 6 membered heteroaryl, and 4 to 7 membered heterocycloalkyl rings are optionally substituted with CN. In another embodiment of Formula (Ia), R$^3$ is H; R$^1$ is 4 to 7 membered heterocycloalkyl; wherein the R$^1$ 4 to 7 membered heterocycloalkyl is optionally substituted with one or more substituents selected from the group consisting of R$^{1A}$, OR$^{1A}$, NHSO$_2$R$^{1A}$, halo, and NHR$^{1A}$; and R$^{1A}$, at each occurrence, is independently selected from the group consisting of C$_1$-C$_3$-haloalkyl, O—C$_1$-C$_3$-haloalkyl, C$_1$-C$_6$-alkyl, C$_1$-C$_3$ alkylene-phenyl, C$_1$-C$_3$ alkylene-(5 to 6 membered heteroaryl), and C$_1$-C$_3$ alkylene-(4 to 7 membered heterocycloalkyl); wherein the R$^{1A}$ phenyl, 5 to 6 membered heteroaryl, and 4 to 7 membered heterocycloalkyl rings are optionally substituted with CN. In another embodiment of Formula (Ia), R$^3$ is H; and R$^2$ is heterocycloalkyl; wherein the R$^2$ heterocycloalkyl is optionally substituted with one or more R$^{2A}$. In another embodiment of Formula (Ia), R$^3$ is H; and R$^2$ is heterocycloalkenyl; wherein the R$^2$ heterocycloalk-enyl is optionally substituted with one or more R$^{2A}$. In another embodiment of Formula (Ia), R$^3$ is H; R$^2$ is heterocycloalkyl; wherein the R$^2$ heterocycloalkyl is optionally substituted with one or more R$^{2A}$; and R$^{2A}$, at each occurrence, is independently selected from the group consisting of halo, NHR$^5$, SO$_2$R$^7$, SO$_2$NHC(O)OR$^8$, C(O)R$^8$, C(O)OR$^8$, C(O)OH, C(O)NHR$^5$, C(O)NR$^5$R$^6$, C$_1$-C$_5$ alkyl, and C$_3$-C$_7$ cycloalkyl; wherein the R$^{2A}$ C$_1$-C$_5$ alkyl and C$_3$-C$_7$ cycloalkyl are optionally substituted with one, two, or three substituents independently selected from the group consisting of R$^4$, C(O)NR$^{11}$R$^{12}$, and OH. In another embodiment of Formula (Ia), R$^3$ is H; R$^2$ is heterocycloalkenyl; wherein the R$^2$ heterocycloalkenyl is optionally substituted with one or more R$^{2A}$; and R$^{2A}$, at each occurrence, is independently selected from the group consisting of halo, NHR$^5$, SO$_2$R$^7$, SO$_2$NHC(O)OR$^8$, C(O)R$^8$, C(O)OR$^8$, C(O)OH, C(O)NHR$^5$, C(O)NR$^5$R$^6$, C$_1$-C$_5$ alkyl, and C$_3$-C$_7$ cycloalkyl; wherein the R$^{2A}$ C$_1$-C$_5$ alkyl and C$_3$-C$_7$ cycloalkyl are optionally substituted with one, two, or three substituents independently selected from the group consisting of R$^4$, C(O)NR$^{11}$R$^{12}$, and OH.

Still another embodiment pertains to compounds of Formula (Ia), selected from the group consisting of 4-(5-fluoro-2-methoxyphenyl)-6-(piperidin-4-yl)-7H-pyrrolo[2,3-d]pyrimidine;

4-(5-fluoro-2-methoxyphenyl)-6-(1-methylpiperidin-4-yl)-7H-pyrrolo[2,3-d]pyrimidine;

4-(5-fluoro-2-methoxyphenyl)-6-(1,2,3,6-tetrahydropyridin-4-yl)-7H-pyrrolo[2,3-d]pyrimidine;

4-(5-fluoro-2-methoxyphenyl)-6-(1-methyl-1,2,3,6-tetrahydropyridin-4-yl)-7H-pyrrolo[2,3-d]pyrimidine;

4-(5-fluoro-2-methoxyphenyl)-6-[1-(methylsulfonyl)-1,2,3,6-tetrahydropyridin-4-yl]-7H-pyrrolo[2,3-d]pyrimidine;

1-{4-[4-(5-fluoro-2-methoxyphenyl)-7H-pyrrolo[2,3-d]pyrimidin-6-yl]-3,6-dihydropyridin-1(2H)-yl}ethanone;

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone;

6-[1-(cyclopropylsulfonyl)-1,2,3,6-tetrahydropyridin-4-yl]-4-(5-fluoro-2-methoxyphenyl)-7H-pyrrolo[2,3-d]pyrimidine;

N-benzyl-4-fluoro-3-[6-(piperidin-4-yl)-7H-pyrrolo[2,3-d]pyrimidin-4-yl]aniline;

4-(5-fluoro-2-methoxyphenyl)-6-[1-(propan-2-ylsulfonyl)-1,2,3,6-tetrahydropyridin-4-yl]-7H-pyrrolo[2,3-d]pyrimidine;

cyclopropyl{4-[4-(5-fluoro-2-methoxyphenyl)-7H-pyrrolo[2,3-d]pyrimidin-6-yl]-3,6-dihydropyridin-1(2H)-yl}methanone;

azetidin-2-yl{4-[4-(5-fluoro-2-methoxyphenyl)-7H-pyrrolo[2,3-d]pyrimidin-6-yl]-3,6-dihydropyridin-1(2H)-yl}methanone;

4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one;

5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one;

{4-[4-(5-fluoro-2-methoxyphenyl)-7H-pyrrolo[2,3-d]pyrimidin-6-yl]-3,6-dihydropyridin-1(2H)-yl}(tetrahydro-2H-pyran-3-yl)methanone;

(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone;

4-[4-(5-fluoro-2-methoxyphenyl)-7H-pyrrolo[2,3-d]pyrimidin-6-yl]-N-methyl-3,6-dihydropyridine-1(2H)-carboxamide;

1-{4-[4-(5-fluoro-2-methoxyphenyl)-7H-pyrrolo[2,3-d]pyrimidin-6-yl]-3,6-dihydropyridin-1(2H)-yl}-2-methoxyethanone;

4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide;

3-{4-[4-(5-fluoro-2-methoxyphenyl)-7H-pyrrolo[2,3-d]pyrimidin-6-yl]-3,6-dihydropyridin-1(2H)-yl}propane-1,2-diol;

6-(1-benzyl-1,2,3,6-tetrahydropyridin-4-yl)-4-(5-fluoro-2-methoxyphenyl)-7H-pyrrolo[2,3-d]pyrimidine;

4-({4-[4-(5-fluoro-2-methoxyphenyl)-7H-pyrrolo[2,3-d]pyrimidin-6-yl]-3,6-dihydropyridin-1(2H)-yl}methyl)benzonitrile;

3-({4-[4-(5-fluoro-2-methoxyphenyl)-7H-pyrrolo[2,3-d]pyrimidin-6-yl]-3,6-dihydropyridin-1(2H)-yl}methyl)benzonitrile;

4-(5-fluoro-2-methoxyphenyl)-6-[1-(tetrahydro furan-2-ylmethyl)-1,2,3,6-tetrahydropyridin-4-yl]-7H-pyrrolo[2,3-d]pyrimidine;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide;

4-(5-fluoro-2-methoxyphenyl)-6-[1-(pyridin-2-ylmethyl)-1,2,3,6-tetrahydropyridin-4-yl]-7H-pyrrolo[2,3-d]pyrimidine;

4-(5-fluoro-2-methoxyphenyl)-6-[1-(pyridin-4-ylmethyl)-1,2,3,6-tetrahydropyridin-4-yl]-7H-pyrrolo[2,3-d]pyrimidine;

4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine;

N-benzyl-4-fluoro-3-{6-[1-(methylsulfonyl)-1,2,3,6-tetrahydropyridin-4-yl]-7H-pyrrolo[2,3-d]pyrimidin-4-yl}aniline;

4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

4-fluoro-3-{6-[1-(methylsulfonyl)-1,2,3,6-tetrahydropyridin-4-yl]-7H-pyrrolo[2,3-d]pyrimidin-4-yl}-N-(tetrahydrofuran-2-ylmethyl)aniline;

4-fluoro-3-{6-[1-(methylsulfonyl)-1,2,3,6-tetrahydropyridin-4-yl]-7H-pyrrolo[2,3-d]pyrimidin-4-yl}-N-(pyridin-2-ylmethyl)aniline;

4-(5-fluoro-2-methoxyphenyl)-6-[1-(pyridin-3-ylmethyl)-1,2,3,6-tetrahydropyridin-4-yl]-7H-pyrrolo[2,3-d]pyrimidine;

6-[1-(3-fluorobenzyl)-1,2,3,6-tetrahydropyridin-4-yl]-4-(5-fluoro-2-methoxyphenyl)-7H-pyrrolo[2,3-d]pyrimidine;

6-[1-(3,5-difluorobenzyl)-1,2,3,6-tetrahydropyridin-4-yl]-4-(5-fluoro-2-methoxyphenyl)-7H-pyrrolo[2,3-d]pyrimidine;

4-fluoro-3-{6-[1-(methylsulfonyl)-1,2,3,6-tetrahydropyridin-4-yl]-7H-pyrrolo[2,3-d]pyrimidin-4-yl}-N-(pyridin-4-ylmethyl)aniline;

6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine;

4-(5-fluoro-2-methoxyphenyl)-6-[1-(piperidin-4-ylmethyl)-1,2,3,6-tetrahydropyridin-4-yl]-7H-pyrrolo[2,3-d]pyrimidine;

4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine;

4-(5-chloro-2-fluoro-3-methylphenyl)-6-[1-(methylsulfonyl)-1,2,3,6-tetrahydropyridin-4-yl]-7H-pyrrolo[2,3-d]pyrimidine;

4-(2-butoxy-5-fluorophenyl)-6-[1-(methylsulfonyl)-1,2,3,6-tetrahydropyridin-4-yl]-7H-pyrrolo[2,3-d]pyrimidine;

4-[5-methyl-2-(propan-2-yloxy)phenyl]-6-[1-(methylsulfonyl)-1,2,3,6-tetrahydropyridin-4-yl]-7H-pyrrolo[2,3-d]pyrimidine;

4-(2-methoxy-5-methylphenyl)-6-[1-(methylsulfonyl)-1,2,3,6-tetrahydropyridin-4-yl]-7H-pyrrolo[2,3-d]pyrimidine;

4-(5-chloro-2-methoxyphenyl)-6-[1-(methylsulfonyl)-1,2,3,6-tetrahydropyridin-4-yl]-7H-pyrrolo[2,3-d]pyrimidine;

4-(2,4-difluorophenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethyl)phenyl]-7H-pyrrolo[2,3-d]pyrimidine;

N-(3-{6-[1-(methylsulfonyl)-1,2,3,6-tetrahydropyridin-4-yl]-7H-pyrrolo[2,3-d]pyrimidin-4-yl}phenyl)methanesulfonamide;

4-(5-fluoro-2-propoxyphenyl)-6-[1-(methylsulfonyl)-1,2,3,6-tetrahydropyridin-4-yl]-7H-pyrrolo[2,3-d]pyrimidine;

4-(2-fluoro-5-methylphenyl)-6-[1-(methylsulfonyl)-1,2,3,6-tetrahydropyridin-4-yl]-7H-pyrrolo[2,3-d]pyrimidine;

4-[2-fluoro-5-(trifluoromethyl)phenyl]-6-[1-(methylsulfonyl)-1,2,3,6-tetrahydropyridin-4-yl]-7H-pyrrolo[2,3-d]pyrimidine;

4-[2-fluoro-5-(propan-2-yloxy)phenyl]-6-[1-(methylsulfonyl)-1,2,3,6-tetrahydropyridin-4-yl]-7H-pyrrolo[2,3-d]pyrimidine;

4-(5-methyl-2-propoxyphenyl)-6-[1-(methylsulfonyl)-1,2,3,6-tetrahydropyridin-4-yl]-7H-pyrrolo[2,3-d]pyrimidine;

4-(5-butoxy-2-fluorophenyl)-6-[1-(methylsulfonyl)-1,2,3,6-tetrahydropyridin-4-yl]-7H-pyrrolo[2,3-d]pyrimidine;

4-(2-fluoro-3-methoxyphenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[3-(trifluoromethoxy)phenyl]-7H-pyrrolo[2,3-d]pyrimidine;

4-(1-methyl-1H-pyrazol-4-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethoxy)phenyl]-7H-pyrrolo[2,3-d]pyrimidine;

4-(4-methoxypyridin-3-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-(morpholin-4-yl)-7H-pyrrolo[2,3-d]pyrimidine;

6(4,4-difluorocyclohex-1-en-1-yl)-4-(5-fluoro-2-methoxyphenyl)-7H-pyrrolo[2,3-d]pyrimidine;

6-[1-(methylsulfonyl)-1,2,3,6-tetrahydropyridin-4-yl]-4-(pyrrolidin-1-yl)-7H-pyrrolo[2,3-d]pyrimidine;

4-(4,4-difluoropiperidin-1-yl)-6-[1-(methylsulfonyl)-1,2,3,6-tetrahydropyridin-4-yl]-7H-pyrrolo[2,3-d]pyrimidine;

4-(3,3-difluoroazetidin-1-yl)-6-[1-(methylsulfonyl)-1,2,3,6-tetrahydropyridin-4-yl]-7H-pyrrolo[2,3-d]pyrimidine;

6-(3,6-dihydro-2H-pyran-4-yl)-4-(5-fluoro-2-methoxyphenyl)-7H-pyrrolo[2,3-d]pyrimidine;

tert-butyl 4-[4-(2-ethoxy-5-fluorophenyl)-7H-pyrrolo[2,3-d]pyrimidin-6-yl]-3,6-dihydropyridine-1(2H)-carboxylate;

4-(2-ethoxy-5-fluorophenyl)-6-(1,2,3,6-tetrahydropyridin-4-yl)-7H-pyrrolo[2,3-d]pyrimidine;

N-[4-({4-[4-(2-ethoxy-5-fluorophenyl)-7H-pyrrolo[2,3-d]pyrimidin-6-yl]-3,6-dihydropyridin-1(2H)-yl}methyl)phenyl]acetamide;

tert-butyl [4-({4-[4-(5-fluoro-2-methoxyphenyl)-7H-pyrrolo[2,3-d]pyrimidin-6-yl]-3,6-dihydropyridin-1(2H)-yl}methyl)phenyl]carbamate;

4-({4-[4-(5-fluoro-2-methoxyphenyl)-7H-pyrrolo[2,3-d]pyrimidin-6-yl]-3,6-dihydropyridin-1(2H)-yl}methyl)aniline;

methyl 4-({4-[4-(5-fluoro-2-methoxyphenyl)-7H-pyrrolo[2,3-d]pyrimidin-6-yl]-3,6-dihydropyridin-1(2H)-yl}methyl)benzoate;

4-({4-[4-(5-fluoro-2-methoxyphenyl)-7H-pyrrolo[2,3-d]pyrimidin-6-yl]-3,6-dihydropyridin-1(2H)-yl}methyl)benzoic acid;

methyl trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylate;

trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylic acid;

4-[4-(5-fluoro-2-methoxyphenyl)-7H-pyrrolo[2,3-d]pyrimidin-6-yl]-N,N-dimethyl-3,6-dihydropyridine-1(2H)-carboxamide;

4-[4-(2,3-difluorophenyl)-7H-pyrrolo[2,3-d]pyrimidin-6-yl]-N,N-dimethyl-3,6-dihydropyridine-1(2H)-carboxamide;

(2S)-cyclohexyl({4-[4-(5-fluoro-2-methoxyphenyl)-7H-pyrrolo[2,3-d]cyclohex-3-en-1-yl}amino)acetic acid;

N-{4-[4-(5-fluoro-2-methoxyphenyl)-7H-pyrrolo[2,3-d]pyrimidin-6-yl]cyclohex-3-en-1-yl}-L-valine;

4-[4-(5-fluoro-2-methoxyphenyl)-7H-pyrrolo[2,3-d]pyrimidin-6-yl]cyclohex-3-ene-1-carboxylic acid;

2-{4-[4-(5-fluoro-2-methoxyphenyl)-7H-pyrrolo[2,3-d]pyrimidin-6-yl]-3,6-dihydropyridin-1(2H)-yl}-N,N-dimethylacetamide;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]methanesulfonamide;

ethyl ({4-[4-(5-fluoro-2-methoxyphenyl)-7H-pyrrolo[2,3-d]pyrimidin-6-yl]-3,6-dihydropyridin-1(2H)-yl}sulfonyl)carbamate;

N-{4-[4-(5-fluoro-2-methoxyphenyl)-7H-pyrrolo[2,3-d]pyrimidin-6-yl]cyclohex-3-en-1-yl}-3-methyl-L-valine;

N-{4-[4-(5-fluoro-2-methoxyphenyl)-7H-pyrrolo[2,3-d]pyrimidin-6-yl]cyclohex-3-en-1-yl}-D-valine;

N-{4-[4-(5-fluoro-2-methoxyphenyl)-7H-pyrrolo[2,3-d]pyrimidin-6-yl]cyclohex-3-en-1-yl}-L-leucine;

4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid;

(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid; and pharmaceutically acceptable salts thereof.

In another aspect, the present invention relates to pharmaceutical compositions comprising a pharmaceutically acceptable excipient and a therapeutically effective amount of a compound of Formula (Ia), or a pharmaceutically acceptable salt thereof.

In another aspect, the present invention relates to methods of treating cancer in a patient, comprising administering to a patient suffering from a cancer a therapeutically effective amount of a compound of Formula (Ia), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated radical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of alkyls include methyl, ethyl, n-propyl, isopropyl, n-butyl, isobutyl, sec-butyl, tert-butyl, pentyl, isoamyl, hexyl, pentan-3-y), 2,2-dimethylpropan-2-yl), heptan-4-yl, and 2,6-dimethylheptan-4-yl, and the like.

The term "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms.

The term "O—$C_1$-$C_6$ alkyl" refers to an oxygen atom attached to an alkyl substituent containing from 1 to 6 carbon atoms.

The term "$C_1$-$C_3$ haloalkyl" refers to a haloalkyl substituent containing from 1 to 3 carbon atoms.

The term "O—$C_1$-$C_3$ haloalkyl" refers to an oxygen atom attached to a haloalkyl substituent containing from 1 to 3 carbon atoms.

The term "$C_1$-$C_6$alkyl-O—$C_1$-$C_6$ alkyl" refers to an alkyl substituent containing from 1 to 6 carbon atoms attached to an oxygen atom attached to an alkyl substituent containing from 1 to 6 carbon atoms.

The term "alkylene" (alone or in combination with another term(s)) means a straight- or branched-chain saturated diradical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. The term "$C_1$-$C_3$ alkylene" refers to an alkylene substituent containing from 1 to 3 carbon atoms.

The term "alkenyl" (alone or in combination with another term(s)) means a straight- or branched-chain radical of an alkene containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl(vinyl), 2-propenyl, 3-propenyl, 1,4-pentadienyl, 1,4-butadienyl, 1-butenyl, 2-butenyl, and 3-butenyl and the like. The term "$C_2$-$C_5$ alkenyl" means an alkenyl group containing 2-5 carbon atoms.

The term "alkynyl" (alone or in combination with another term(s)) means a straight- or branched-chain radical of an alkyne containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like. The term "$C_2$-$C_6$ alkynyl" means an alkynyl group of 2 to 6 carbon atoms.

The term "cycloalkyl" (alone or in combination with another term(s)) means a saturated cyclic hydrocarbyl substituent containing from 3 or more carbon ring atoms ("ring atoms" are the atoms bound together to form the ring or rings of a cyclic substituent). A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic (contain more than one ring). Examples of polycyclic cycloalkyls include bridged, fused, and spirocyclic cycloalkyls.

The term "$C_3$-$C_7$ cycloalkyl" (alone or in combination with another term(s)) means a saturated cyclic radical of a monocyclic cycloalkane containing from 3 to 7 carbon ring atoms. Examples of monocyclic cycloalkyl groups include, but are not limited to, cyclopropyl(cyclopropanyl), cyclobutyl(cyclobutanyl), cyclopentyl(cyclopentanyl), cyclopentenyl, cyclohexyl(cyclohexanyl), and cycloheptyl.

The term "cycloalkenyl" (alone or in combination with another term(s)) means a partially unsaturated cyclic hydrocarbyl substituent containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "$C_5$-$C_7$ cycloalkenyl" (alone or in combination with another term(s)) means a partially unsaturated monocylic cycloalkane radical containing from 5 to 7 carbon ring atoms. Examples of single-ring cycloalkenyls include cyclopentenyl, cyclohexenyl, and cycloheptenyl.

The term "heterocycloalkyl" (alone or in combination with another term(s)) means a non-aromatic saturated monocyclic or polycyclic heterocycloalkane radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkyl may be a single carbon ring, which typically contains from 3 to 8 ring atoms and more typically from 3 to 6 ring atoms. Examples of single-ring heterocycloalkyls include oxetanyl, azetidinyl, thietanyl, tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, 3-pyrrolinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, trithianyl, azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl, azocanyl, thiocanyl, oxocanyl, tetrahydro-2H-thiopyranyl 1,1-dioxide and 3,4,5,6-tetrahydro-2H-oxocinyl. A heterocycloalkyl may alternatively be polycyclic (contain more than one ring). Examples of polycyclic heterocycloalkyls include bridged, fused, and spirocyclic heterocycloalkyls in which at least one ring is a heterocycloalkyl and the others are heterocycloalkyl, or cycloalkyl rings.

The term "heterocycloalkenyl" (alone or in combination with another term(s)) means a non-aromatic partially unsaturated monocyclic or polycyclic heterocycloalkene radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkenyl may be a single carbon ring, which typically contains from 3 to 8 ring atoms and more typically from 3 to 6 ring atoms. Examples of single-ring heterocycloalkenyls include 1,2,3,6-tetrahydropyridinyl, and 4,5-dihydro-1H-imidazolyl. A heterocycloalkenyl may alternatively be polycyclic (contain more than one ring). Examples of polycyclic heterocycloalkenyls include bridged, fused, and spirocyclic heterocycloalkenyls in which at least one ring is a heterocycloalkenyl and the others are heterocycloalkenyl, heterocycloalkyl, cycloalkenyl or cycloalkyl rings. Alternatively, a polycyclic heterocycloalkenyl may consist of one or more heterocycloalkyl rings and one or more cycloalkenyl rings. Examples of polycyclic heterocycloalkenyls include 8-azabicyclo[3.2.1]oct-2-enyl, and 1,2,3,3a,4,6a-hexahydrocyclopenta[c]pyrrolyl.

The term "5 to 7-membered heterocycloalkyl" (alone or in combination with another term(s)) means a non-aromatic monocyclic radical having carbon atoms and 1 to 3 heteroatoms independently selected from S, N or O, wherein when two O atoms or one O atom and one S atom are present, the two O atoms or one O atom and one S atom are not bonded to each other, respectively.

The term "4-membered monocyclic heterocycloalkyl" (alone or in combination with another term(s)) means a 4-membered, monocyclic radical having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

The term "5-membered monocyclic heterocycloalkyl" (alone or in combination with another term(s)) means a 5-membered, monocyclic radical having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

The term "6-membered monocyclic heterocycloalkyl" (alone or in combination with another term(s)) means a 6-membered, monocyclic radical having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

The term "7-membered monocyclic heterocycloalkyl" (alone or in combination with another term(s)) means a 7-membered, monocyclic radical having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

The term "8-membered monocyclic heterocycloalkyl" (alone or in combination with another term(s)) means a 8-membered, monocyclic radical having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

The term "aryl" (alone or in combination with another term(s)) means an aromatic hydrocarbon radical. Furthermore, the term "aryl" includes polycyclic aryl groups, such as bicyclic, e.g., naphthyl. Typical aryl groups include phenyl, and naphthyl. The term aryl also includes a "9- to 12-membered bicyclic aryl," which is a ring structure formed by the fusion of a benzene ring to: (1) a cycloalkyl or cycloalkenyl (e.g., indanyl; 1,2,3,4-tetrahydro-naphthalenyl; 6,7,8,9-tetrahydro-5H-benzocycloheptenyl, etc.); (2) another benzene ring (e.g., naphthalenyl); wherein the fusion junctions are at adjacent carbons on the benzene ring; or (3) a heterocycloalkyl or heterocycloalkenyl (e.g., benzo[d][1,3]dioxolyl, isoindolinyl).

The term "heteroaryl" (alone or in combination with another term(s)) means a monocyclic 5 or 6 membered heteroaryl or a bicyclic heteroaryl.

The term "5-membered heteroaryl" (alone or in combination with another term(s)) means a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

The term "6-membered heteroaryl" (alone or in combination with another term(s)) means a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

The term "bicyclic heteroaryl" (alone or in combination with another term(s)) means a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a cycloalkyl or cycloalkenyl; (4) a heterocycloalkyl or heterocycloalkenyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}$H, $^{3}$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^{2}$H), tritium ($^{3}$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK9 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to CDK9 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $R^{1a}$, $R^{1b}$, $R^{1c}$, $R^2$, and $R^3$ in compounds of Formula (I), $R^1$, $R^2$, and $R^3$ in compounds of Formula (Ia), $R^1$ and $R^2$ in compounds of Formula (IIa), and $R^{1B}$, $R^{1C}$, $R^{1D}$, $R^{1E}$, $R^{1F}$, in compounds of Formula (IIIa) are independently selected. The described embodiments of the present invention may be combined. Such combination is contemplated and within the scope of the present invention. For example, it is contemplated that embodiments for any of $R^1$, $R^2$, and $R^3$ in compounds of Formula (Ia) can be combined with embodiments defined for any other of $R^1$, $R^2$, and $R^3$ in compounds of Formula (Ia).

Embodiments of Formula (I)

In one aspect, the present invention relates to compounds of Formula (I) or a pharmaceutically acceptable salt thereof,

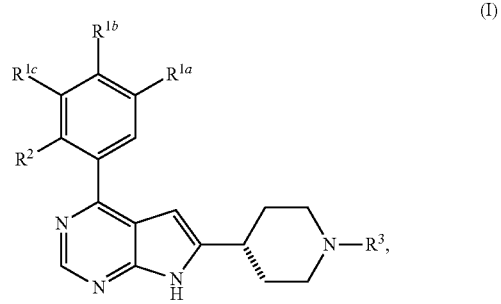

(I)

wherein
two of $R^{1a}$, $R^{1b}$, and $R^{1c}$ are H and the other is selected from the group consisting of: halo, NH—$C_1$-$C_3$alkyene-phenyl, NH—$C_1$-$C_3$alkyene-(5 to 7 membered heteroaryl), and NH—$C_1$-$C_3$alkyene-(5 to 7 membered heterocycloalkyl), O—$C_1$-$C_3$alkyene-phenyl, O—$C_1$-$C_3$alkyene-(5 to 7 membered heteroaryl), and O—$C_1$-$C_3$alkyene-(5 to 7 membered heterocycloalkyl), wherein the phenyl, 5 to 7 membered heteroaryl, or 5 to 7 membered heterocycloalkyl may be substituted with one to three substituents independently selected from the group consisting of: CN, $C_1$-$C_3$ alkyl, halo, OH, OR$^{14}$, NH$_2$, NHR$^{15}$, NR$^{15}$R$^{16}$, C(O)NH$_2$, C(O)NHR$^{15}$, C(O)NR$^{15}$R$^{16}$, SO$_2$NH$_2$, SO$_2$NHR$^{15}$, SO$_2$NR$^{15}$R$^{16}$, C(O)OH, C(O)OR$^{17}$;

R$^2$ is H, CN, C$_1$ haloalkyl, O—C$_1$-C$_3$ alkyl, or halo;

the hashed bond is a single bond or a double bond; and

R$^3$ is selected from the group consisting of: H, SO$_2$R$^7$, SO$_2$NH$_2$, SO$_2$NHR$^5$, SO$_2$NR$^5$R$^6$, C(O)R$^8$, C(O)NH$_2$, C(O)NHR$^5$, C(O)NR$^5$R$^6$, C$_1$-C$_5$ alkyl, C$_2$-C$_5$ alkenyl, aryl, 5 to 7 membered heteroaryl, 5 to 7 membered heterocycloalkyl, C$_5$-C$_7$ cycloalkyl;

where said R$^3$C$_1$-C$_5$ alkyl, C$_2$-C$_5$ alkenyl, aryl, 5 to 7 membered heteroaryl, 5 to 7 membered heterocycloalkyl, or C$_5$-C$_7$cycloalkyl each may be substituted with one, two, or three substituents independently selected from the group consisting of: C$_1$-C$_5$ alkyl, C$_1$-C$_5$ alkenyl, aryl, 5 to 7 membered heteroaryl, 5 to 7 membered heterocycloalkyl, C$_5$-C$_7$cycloalkyl, —C$_1$-C$_3$ haloalkyl, OR$^{10}$, SO$_2$R$^9$, C(O)R$^{10}$, C(O)OR$^{19}$, NH$_2$, NHR$^{11}$, NR$^{11}$R$^{12}$, NHC(O)R$^{10}$, NR$^{11}$C(O)R$^{10}$, NHS(O)$_2$R$^9$, NR$^{11}$S(O)$_2$R$^9$, NHC(O)NH$_2$, NHC(O)NHR$^{11}$, NHC(O)NR$^{11}$R$^{12}$, NR$^{11}$C(O)NHR$^{12}$, NR$^{11}$C(O)NR$^{11}$R$^{13}$, C(O)NH$_2$, C(O)NHR$^{11}$, C(O)NR$^{11}$R$^{12}$, SO$_2$NH$_2$, SO$_2$NHR$^{11}$, SO$_2$NR$^{11}$R$^{12}$, C(O)OH, OH, CN, and halo;

where R$^5$, R$^6$, R$^7$, R$^8$, R$^9$, R$^{19}$, R$^{11}$, R$^{12}$, R$^{13}$, R$^{14}$, R$^{15}$, R$^{16}$, and R$^{17}$ are each independently selected from the group consisting of C$_1$-C$_6$ alkyl, aryl, 5 to 7 membered heteroaryl, 5 to 7 membered heterocycloalkyl, and C$_5$-C$_7$cycloalkyl.

In certain embodiments, R$^3$ is selected from the group consisting of: H, SO$_2$—C$_1$-C$_3$ alkyl; —C$_1$-C$_3$ alkyl, which may be optionally substituted with one or hydroxyls; —C$_1$-C$_3$ haloalkyl; C(O)—C$_1$-C$_3$ alkyl; C(O)—C$_3$-C$_6$ cycloalkyl; C(O)—C$_1$-C$_3$alkylene-OH; SO$_2$—C$_3$-C$_6$ cycloalkyl; C(O)-(5 to 7 membered heterocycloalkyl); wherein the heterocycloalkyl may be substituted with the following: one oxo, or one to three independently chosen —C$_1$-C$_3$ alkyl; C(O)—C$_1$-C$_3$ alkylene-O—C$_1$-C$_3$ alkyl; C(O)NH—C$_1$-C$_3$ alkyl; C(O)NH—C$_2$-C$_5$ alkenyl; C$_3$-C$_6$ cycloalkyl, which may be substituted with one or two hydroxyls; —C$_1$-C$_3$ alkylene-phenyl, wherein the phenyl may be substituted with one to three substituents independently selected from the group consisting of halo, CN, —C$_1$-C$_3$ alkyl, —C$_1$-C$_3$ haloalkyl, and NHC(O)—C$_1$-C$_3$ alkyl, —C$_1$-C$_3$ alkylene-pyridinyl; wherein the pyridinyl may be substituted with one to three substituents independently selected from the group consisting of halo, CN, —C$_1$-C$_3$ alkyl, —C$_1$-C$_3$ haloalkyl, and NHC(O)—C$_1$-C$_3$ alkyl; SO$_2$-(5 to 7 membered heterocycloalkyl); and SO$_2$—C$_1$-C$_3$ haloalkyl. In certain embodiments, R$^1$ is halo and R$^2$ is —O—C$_1$-C$_3$ alkyl. In certain embodiments, R$^1$ is fluoro and R$^2$ is —O-methyl. In certain embodiments, R$^1$ is NH—C$_1$-C$_3$alkyene-phenyl, NH—C$_1$-C$_3$alkyene-pyridinyl, or NH—C$_1$-C$_3$alkyene-tetrahydrofuranyl, wherein the phenyl, pyridinyl, or tetrahydrofuranyl may be substituted with one to three substituents independently selected from the group consisting of: —CN, C$_1$-C$_3$ alkyl, or halo; and R$^2$ is halo. In certain embodiments, R$^1$ is NH—C$_1$-alkyene-phenyl; and R$^2$ is fluoro. In certain embodiments, R$^3$ is selected from the group consisting of: H, SO$_2$—C$_1$-C$_3$ alkyl; —C$_1$-C$_3$ alkyl, which may be optionally substituted with one or hydroxyls; C(O)—C$_1$-C$_3$ alkyl; C(O)—C$_1$-C$_3$alkylene-OH; C(O)NH—C$_1$-C$_3$ alkyl; —C$_1$-C$_3$ alkylene-phenyl, wherein the phenyl may be substituted with one to three substituents independently selected from the group consisting of halo, CN, —C$_1$-C$_3$ alkyl, —C$_1$-C$_3$ haloalkyl, and NHC(O)—C$_1$-C$_3$ alkyl, —C$_1$-C$_3$ alkylene-pyridinyl; wherein the pyridinyl may be substituted with one to three substituents independently selected from the group consisting of halo, CN, —C$_1$-C$_3$ alkyl, —C$_1$-C$_3$ haloalkyl, and NHC(O)—C$_1$-C$_3$ alkyl; SO$_2$-(5 to 7 membered heterocycloalkyl); and SO$_2$—C$_1$-C$_3$ haloalkyl. In certain embodiments, R$^3$ is selected from the group consisting of: H, SO$_2$-methyl, methyl, —C(O)—CH$_3$, —C(O)CH$_2$OH, C(O)NHCH$_3$, CH$_2$CH(OH)CH$_2$OH, and CH$_2$-phenyl-NHC(O)CH$_3$. In certain embodiments, R$^1$ is NH—C$_1$-alkyene-phenyl, and R$^2$ is fluoro; or R$^1$ is fluoro and R$^2$ is —O-methyl. In certain embodiments, R$^3$ is selected from the group consisting of: H, SO$_2$-methyl, methyl, —C(O)—CH$_3$, —C(O)CH$_2$OH, C(O)NHCH$_3$, CH$_2$CH(OH)CH$_2$OH, and CH$_2$-phenyl-NHC(O)CH$_3$. In certain embodiments, the dashed bond is a single bond. In certain embodiments, the dashed bond is a double bond.

In certain embodiments, a compound of formula I is selected from the group consisting of:

4-(5-fluoro-2-methoxyphenyl)-6-(piperidin-4-yl)-7H-pyrrolo[2,3-d]pyrimidine;

4-(5-fluoro-2-methoxyphenyl)-6-(1-methylpiperidin-4-yl)-7H-pyrrolo[2,3-d]pyrimidine;

4-(5-fluoro-2-methoxyphenyl)-6-(1-methyl-1,2,3,6-tetrahydropyridin-4-yl)-7H-pyrrolo[2,3-d]pyrimidine;

4-(5-fluoro-2-methoxyphenyl)-6-[1-(methylsulfonyl)-1,2,3,6-tetrahydropyridin-4-yl]-7H-pyrrolo[2,3-d]pyrimidine;

4-(5-fluoro-2-methoxyphenyl)-6-(1,2,3,6-tetrahydropyridin-4-yl)-7H-pyrrolo[2,3-d]pyrimidine;

1-{4-[4-(5-fluoro-2-methoxyphenyl)-7H-pyrrolo[2,3-d]pyrimidin-6-yl]-3,6-dihydropyridin-1(2H)-yl}ethanone;

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone;

6-[1-(cyclopropylsulfonyl)-1,2,3,6-tetrahydropyridin-4-yl]-4-(5-fluoro-2-methoxyphenyl)-7H-pyrrolo[2,3-d]pyrimidine;

N-benzyl-4-fluoro-3-[6-(piperidin-4-yl)-7H-pyrrolo[2,3-d]pyrimidin-4-yl]aniline;

4-(5-fluoro-2-methoxyphenyl)-6-[1-(propan-2-ylsulfonyl)-1,2,3,6-tetrahydropyridin-4-yl]-7H-pyrrolo[2,3-d]pyrimidine;

cyclopropyl{4-[4-(5-fluoro-2-methoxyphenyl)-7H-pyrrolo[2,3-d]pyrimidin-6-yl]-3,6-dihydropyridin-1(2H)-yl}methanone;

azetidin-2-yl{4-[4-(5-fluoro-2-methoxyphenyl)-7H-pyrrolo[2,3-d]pyrimidin-6-yl]-3,6-dihydropyridin-1(2H)-yl}methanone;

4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one;

5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one;

{4-[4-(5-fluoro-2-methoxyphenyl)-7H-pyrrolo[2,3-d]pyrimidin-6-yl]-3,6-dihydropyridin-1(2H)-yl}(tetrahydro-2H-pyran-3-yl)methanone;

(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone;

4-[4-(5-fluoro-2-methoxyphenyl)-7H-pyrrolo[2,3-d]pyrimidin-6-yl]-N-methyl-3,6-dihydropyridine-1(2H)-carboxamide;

1-{4-[4-(5-fluoro-2-methoxyphenyl)-7H-pyrrolo[2,3-d]pyrimidin-6-yl]-3,6-dihydropyridin-1(2H)-yl}-2-methoxyethanone;

4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide;

3-{4-[4-(5-fluoro-2-methoxyphenyl)-7H-pyrrolo[2,3-d]pyrimidin-6-yl]-3,6-dihydropyridin-1(2H)-yl}propane-1,2-diol;
6-(1-benzyl-1,2,3,6-tetrahydropyridin-4-yl)-4-(5-fluoro-2-methoxyphenyl)-7H-pyrrolo[2,3-d]pyrimidine;
4-({4-[4-(5-fluoro-2-methoxyphenyl)-7H-pyrrolo[2,3-d]pyrimidin-6-yl]-3,6-dihydropyridin-1(2H)-yl}methyl)benzonitrile;
3-({4-[4-(5-fluoro-2-methoxyphenyl)-7H-pyrrolo[2,3-d]pyrimidin-6-yl]-3,6-dihydropyridin-1(2H)-yl}methyl)benzonitrile;
4-(5-fluoro-2-methoxyphenyl)-6-[1-(tetrahydrofuran-2-ylmethyl)-1,2,3,6-tetrahydropyridin-4-yl]-7H-pyrrolo[2,3-d]pyrimidine;
N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide;
4-(5-fluoro-2-methoxyphenyl)-6-[1-(pyridin-2-ylmethyl)-1,2,3,6-tetrahydropyridin-4-yl]-7H-pyrrolo[2,3-d]pyrimidine;
4-(5-fluoro-2-methoxyphenyl)-6-[1-(pyridin-4-ylmethyl)-1,2,3,6-tetrahydropyridin-4-yl]-7H-pyrrolo[2,3-d]pyrimidine;
4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine;
N-benzyl-4-fluoro-3-{6-[1-(methylsulfonyl)-1,2,3,6-tetrahydropyridin-4-yl]-7H-pyrrolo[2,3-d]pyrimidin-4-yl}aniline;
4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;
3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;
4-fluoro-3-{6-[1-(methylsulfonyl)-1,2,3,6-tetrahydropyridin-4-yl]-7H-pyrrolo[2,3-d]pyrimidin-4-yl}-N-(tetrahydrofuran-2-ylmethyl)aniline;
4-fluoro-3-{6-[1-(methylsulfonyl)-1,2,3,6-tetrahydropyridin-4-yl]-7H-pyrrolo[2,3-d]pyrimidin-4-yl}-N-(pyridin-2-ylmethyl)aniline;
4-(5-fluoro-2-methoxyphenyl)-6-[1-(pyridin-3-ylmethyl)-1,2,3,6-tetrahydropyridin-4-yl]-7H-pyrrolo[2,3-d]pyrimidine;
6-[1-(3-fluorobenzyl)-1,2,3,6-tetrahydropyridin-4-yl]-4-(5-fluoro-2-methoxyphenyl)-7H-pyrrolo[2,3-d]pyrimidine;
6-[1-(3,5-difluorobenzyl)-1,2,3,6-tetrahydropyridin-4-yl]-4-(5-fluoro-2-methoxyphenyl)-7H-pyrrolo[2,3-d]pyrimidine;
4-fluoro-3-{6-[1-(methylsulfonyl)-1,2,3,6-tetrahydropyridin-4-yl]-7H-pyrrolo[2,3-d]pyrimidin-4-yl}-N-(pyridin-4-ylmethyl)aniline;
6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine;
4-(5-fluoro-2-methoxyphenyl)-6-[1-(piperidin-4-ylmethyl)-1,2,3,6-tetrahydropyridin-4-yl]-7H-pyrrolo[2,3-d]pyrimidine; and
4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine; or a pharmaceutically acceptable salt thereof.

Embodiments of Formula (Ia)

In one aspect, the present invention relates to compounds of Formula (Ia) or a pharmaceutically acceptable salt thereof,

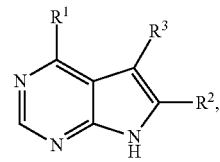

(Ia)

wherein
R$^1$ is selected from the group consisting of phenyl, 5 to 6 membered heteroaryl, 4 to 7 membered heterocycloalkyl and 4 to 7 membered heterocycloalkenyl; wherein the R$^1$ phenyl, 5 to 6 membered heteroaryl, 4 to 7 membered heterocycloalkyl and 4 to 7 membered heterocycloalkenyl are optionally substituted with one or more substituents selected from the group consisting of R$^{1A}$, OR$^{1A}$, NHSO$_2$R$^{1A}$, halo, CN, and NHR$^{1A}$;

R$^{1A}$, at each occurrence, is independently selected from the group consisting of C$_1$-C$_3$-haloalkyl, O—C$_1$-C$_3$-haloalkyl, C$_1$-C$_6$-alkyl, C$_1$-C$_3$ alkylene-phenyl, C$_1$-C$_3$ alkylene-(5 to 6 membered heteroaryl), and C$_1$-C$_3$ alkylene-(4 to 7 membered heterocycloalkyl); wherein the R$^{1A}$ phenyl, 5 to 6 membered heteroaryl, and 4 to 7 membered heterocycloalkyl rings are optionally substituted with one to three substituents independently selected from the group consisting of CN, C$_1$-C$_3$ alkyl, halo, OH, OR$^{14}$, NH$_2$, NHR$^{15}$, NR$^{15}$R$^{16}$, C(O)NH$_2$, C(O)NHR$^{15}$, C(O)NR$^{15}$R$^{16}$, SO$_2$NH$_2$, SO$_2$NHR$^{15}$, SO$_2$NR$^{15}$R$^{16}$, C(O)OH, and C(O)OR$^{17}$;

R$^2$ is selected from the group consisting of cycloalkyl, cycloalkenyl, heterocycloalkyl and heterocycloalkenyl; wherein the R$^2$ cycloalkyl, cycloalkenyl, heterocycloalkyl and heterocycloalkenyl are optionally substituted with one or more R$^{2A}$;

R$^{2A}$, at each occurrence, is independently selected from the group consisting of halo, NHR$^5$, SO$_2$R$^7$, SO$_2$NH$_2$, SO$_2$NHR$^5$, SO$_2$NR$^5$R$^6$, SO$_2$NHC(O)OR$^8$, C(O)R$^8$, C(O)OR$^8$, C(O)OH, C(O)NH$_2$, C(O)NHR$^5$, C(O)NR$^5$R$^6$, C$_1$-C$_5$ alkyl, C$_2$-C$_5$ alkenyl, aryl, 5 to 6 membered heteroaryl, 4 to 7 membered heterocycloalkyl, 4 to 7 membered heterocycloalkenyl, and C$_3$-C$_7$ cycloalkyl; wherein the R$^{2A}$ C$_1$-C$_5$ alkyl, C$_2$-C$_5$ alkenyl, aryl, 5 to 6 membered heteroaryl, 4 to 7 membered heterocycloalkyl, and C$_3$-C$_7$ cycloalkyl are optionally substituted with one, two, or three substituents independently selected from the group consisting of R$^4$, OR$^{19}$, SO$_2$R$^9$, C(O)R$^{19}$, C(O)OR$^{19}$, NH$_2$, NHR$^{11}$, NR$^{11}$R$^{12}$, NHC(O)R$^{19}$, NR$^{11}$C(O)R$^{19}$, NHS(O)$_2$R$^9$, NR$^{11}$S(O)$_2$R$^9$, NHC(O)NH$_2$, NHC(O)NHR$^{11}$, NHC(O)NR$^{11}$R$^{12}$, NR$^{11}$C(O)NHR$^{12}$, NR$^{11}$C(O)NR$^{11}$R$^{13}$, C(O)NH$_2$, C(O)NHR$^{11}$, C(O)NR$^{11}$R$^{12}$, SO$_2$NH$_2$, SO$_2$NHR$^{11}$, SO$_2$NR$^{11}$R$^{12}$, C(O)OH, OH, CN, and halo;

R$^3$ is selected from the group consisting of hydrogen, C$_1$-C$_4$ alkyl, NO$_2$, CN, F, Cl, Br and I;

R$^4$, at each occurrence, is independently selected from the group consisting of C$_1$-C$_5$ alkyl, C$_1$-C$_5$ alkenyl, aryl, 5 to 6 membered heteroaryl, 4 to 7 membered heterocycloalkyl, and C$_3$-C$_7$ cycloalkyl; wherein the R$^4$ C$_1$-C$_5$ alkyl and C$_1$-C$_5$ alkenyl are optionally substituted with one or more substituents selected from the group consisting of halo, C$_1$-C$_3$-haloalkyl, C(O)OH, CN, and NH$_2$; wherein the R$^4$ aryl, 5 to 6 membered heteroaryl, 4 to 7 membered heterocycloalkyl, and C$_3$-C$_7$ cycloalkyl are optionally substituted with one or more substituents selected from the group consisting of halo, C$_1$-C$_3$-haloalkyl, C(O)OH, CN, $NH_2$, $NHSO_2R^{17}$; $NHC(O)R^{17}$, $C(O)R^{17}$, $C(O)OR^{17}$, and $NHC(O)OR^{17}$;

$R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurrence, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and C(O)OH; and $R^{18}$, at each occurrence, is $C_1$-$C_6$ alkyl.

In one embodiment of Formula (Ia), $R^1$ is selected from the group consisting of phenyl, 5 to 6 membered heteroaryl, 4 to 7 membered heterocycloalkyl and 4 to 7 membered heterocycloalkenyl; wherein the $R^1$ phenyl, 5 to 6 membered heteroaryl, 4 to 7 membered heterocycloalkyl and 4 to 7 membered heterocycloalkenyl are optionally substituted with one or more substituents selected from the group consisting of $R^{1A}$, $OR^{1A}$, $NHSO_2R^{1A}$, halo, CN, and $NHR^{1A}$. In another embodiment of Formula (Ia), $R^1$ is selected from the group consisting of phenyl, 5 to 6 membered heteroaryl and 4 to 7 membered heterocycloalkyl; wherein the $R^1$ phenyl, 5 to 6 membered heteroaryl and 4 to 7 membered heterocycloalkyl are optionally substituted with one or more substituents selected from the group consisting of $R^{1A}$, $OR^{1A}$, $NHSO_2R^{1A}$, halo, and $NHR^{1A}$. In another embodiment of Formula (Ia), $R^1$ is phenyl; wherein the $R^1$ phenyl is optionally substituted with one or more substituents selected from the group consisting of $R^{1A}$, $OR^{1A}$, $NHSO_2R^{1A}$, halo, and $NHR^{1A}$. In another embodiment of Formula (Ia), $R^1$ is 5 to 6 membered heteroaryl; wherein the $R^1$ 5 to 6 membered heteroaryl is optionally substituted with one or more substituents selected from the group consisting of $R^{1A}$, $OR^{1A}$, $NHSO_2R^{1A}$, halo, and $NHR^{1A}$. In another embodiment of Formula (Ia), $R^1$ is 4 to 7 membered heterocycloalkyl; wherein the $R^1$ 4 to 7 membered heterocycloalkyl is optionally substituted with one or more substituents selected from the group consisting of $R^{1A}$, $OR^{1A}$, $NHSO_2R^{1A}$, halo, and $NHR^{1A}$.

In one embodiment of Formula (Ia), $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, C(O)OH, and $C(O)OR^{17}$. In another one embodiment of Formula (Ia), $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with CN.

In one embodiment of Formula (Ia), $R^2$ is selected from the group consisting of cycloalkyl, cycloalkenyl, heterocycloalkyl and heterocycloalkenyl; wherein the $R^2$ cycloalkyl, cycloalkenyl, heterocycloalkyl and heterocycloalkenyl are optionally substituted with one or more $R^{2A}$. In another embodiment of Formula (Ia), $R^2$ is selected from the group consisting of cycloalkenyl, heterocycloalkyl and heterocycloalkenyl; wherein the $R^2$ cycloalkenyl, heterocycloalkyl and heterocycloalkenyl are optionally substituted with one or more $R^{2A}$. In another embodiment of Formula (Ia), $R^2$ is cycloalkenyl; wherein the $R^2$ cycloalkenyl is optionally substituted with one or more $R^{2A}$. In another embodiment of Formula (Ia), $R^2$ is heterocycloalkyl; wherein the $R^2$ heterocycloalkyl is optionally substituted with one or more $R^{2A}$. In another embodiment of Formula (Ia), $R^2$ is heterocycloalkenyl; wherein the $R^2$ heterocycloalkenyl is optionally substituted with one or more $R^{2A}$.

In one embodiment of Formula (Ia), $R^{2A}$, at each occurrence, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, C(O)OH, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, 4 to 7 membered heterocycloalkenyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}$, $NHC(O)R^{10}$, $NR^{11}C(O)R^{10}$, $NHS(O)_2R^9$, $NR^{11}S(O)_2R^9$, $NHC(O)NH_2$, $NHC(O)NHR^{11}$, $NHC(O)NR^{11}R^{12}$, $NR^{11}C(O)NHR^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, C(O)OH, OH, CN, and halo. In another embodiment of Formula (Ia), $R^{2A}$, at each occurrence, is independently selected from the group consisting of halo, $NHR^5$, $SO_2R^7$, $SO_2NHC(O)OR^8$, $C(O)R^8$, $C(O)OR^8$, C(O)OH, $C(O)NHR^5$, $C(O)NR^5R^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and OH.

In one embodiment of Formula (Ia), $R^3$ is selected from the group consisting of hydrogen, $C_1$-$C_4$ alkyl, $NO_2$, CN, F, Cl, Br and I. In another embodiment of Formula (Ia), $R^3$ is hydrogen.

In one embodiment of Formula (Ia), $R^4$, at each occurrence, is independently selected from the group consisting of $C_1$-$C_5$ alkyl, $C_1$-$C_5$ alkenyl, aryl, 5 to 6 membered heteroaryl, 4 to 7 membered heterocycloalkyl, and $C_3$-$C_7$ cycloalkyl; wherein the $R^4C_1$-$C_5$ alkyl and $C_1$-$C_5$ alkenyl are optionally substituted with one or more substituents selected from the group consisting of halo, $C_1$-$C_3$-haloalkyl, C(O)OH, CN, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, C(O)OH, CN, $NH_2$, $NHSO_2R^{17}$; $NHC(O)R^{17}$, $C(O)R^{17}$, $C(O)OR^{17}$, and $NHC(O)OR^{17}$. In another embodiment of Formula (Ia), $R^4$, at each occurrence, is independently selected from the group consisting of $C_1$-$C_5$ alkyl, aryl, 5 to 6 membered heteroaryl, and 4 to 7 membered heterocycloalkyl; wherein the $R^4C_1$-$C_5$ alkyl is optionally substituted with one or more C(O)OH; wherein the $R^4$ aryl, 5 to 6 membered heteroaryl, and 4 to 7 membered heterocycloalkyl are optionally substituted with one or more substituents selected from the group consisting of halo, $C_1$-$C_3$-haloalkyl, C(O)OH, CN, $NH_2$, $NHSO_2R^{17}$; $NHC(O)R^{17}$, $C(O)OR^{17}$, and $NHC(O)OR^{17}$.

In one embodiment of Formula (Ia), $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurrence, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, C(O)OR$^{18}$, OR$^{18}$, and C(O)OH; and R$^{18}$, at each occurrence, is $C_1$-$C_6$ alkyl. In another embodiment of Formula (Ia), $R^5$, $R^6$, $R^7$, $R^8$, $R^{11}$, $R^{12}$, and $R^{17}$, at each occurrence, are independently selected from the group consisting of $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl; wherein the $R^5$, $R^6$, $R^7$, $R^8$, $R^{11}$, $R^{12}$, and $R^{17}C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, C(O)OR$^{18}$, OR$^{18}$, and C(O)OH; and R$^{18}$, at each occurrence, is $C_1$-$C_6$ alkyl.

In one embodiment of Formula (Ia), $R^1$ is selected from the group consisting of phenyl, 5 to 6 membered heteroaryl, and 4 to 7 membered heterocycloalkyl; wherein the $R^1$ phenyl, 5 to 6 membered heteroaryl, and 4 to 7 membered heterocycloalkyl are optionally substituted with one or more substituents selected from the group consisting of $R^{1A}$, OR$^{1A}$, NHSO$_2$R$^{1A}$, halo, and NHR$^{1A}$;

$R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three CN;

$R^2$ is selected from the group consisting of cycloalkenyl, heterocycloalkyl and heterocycloalkenyl; wherein the $R^2$ cycloalkenyl, heterocycloalkyl and heterocycloalkenyl are optionally substituted with one or more $R^{2A}$;

$R^{2A}$, at each occurrence, is independently selected from the group consisting of halo, NHR$^5$, SO$_2$R$^7$, SO$_2$NHC(O)OR$^8$, C(O)R$^8$, C(O)OR$^8$, C(O)OH, C(O)NHR$^5$, C(O)NR$^5$R$^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, C(O)NR$^{11}$R$^{12}$, and OH;

$R^3$ is hydrogen;

$R^4$, at each occurrence, is independently selected from the group consisting of $C_1$-$C_5$ alkyl, aryl, 5 to 6 membered heteroaryl, and 4 to 7 membered heterocycloalkyl; wherein the $R^4C_1$-$C_5$ alkyl is optionally substituted with one or more C(O)OH; wherein the $R^4$ aryl, 5 to 6 membered heteroaryl, and 4 to 7 membered heterocycloalkyl are optionally substituted with one or more substituents selected from the group consisting of halo, $C_1$-$C_3$-haloalkyl, C(O)OH, CN, NH$_2$, NHSO$_2$R$^{17}$; NHC(O)R$^{17}$, C(O)OR$^{17}$, and NHC(O)OR$^{17}$;

$R^5$, $R^6$, $R^7$, $R^8$, $R^{11}$, $R^{12}$, and $R^{17}$, at each occurrence, are independently selected from the group consisting of $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl; wherein the $R^5$, $R^6$, $R^7$, $R^8$, $R^{11}$, $R^{12}$, and $R^{17}C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, C(O)OR$^{18}$, OR$^{18}$, and C(O)OH; and R$^{18}$, at each occurrence, is $C_1$-$C_6$ alkyl.

Still another embodiment pertains to compounds of Formula (Ia), selected from the group consisting of 4-(5-fluoro-2-methoxyphenyl)-6-(piperidin-4-yl)-7H-pyrrolo[2,3-d]pyrimidine;

4-(5-fluoro-2-methoxyphenyl)-6-(1-methylpiperidin-4-yl)-7H-pyrrolo[2,3-d]pyrimidine;

4-(5-fluoro-2-methoxyphenyl)-6-(1,2,3,6-tetrahydropyridin-4-yl)-7H-pyrrolo[2,3-d]pyrimidine;

4-(5-fluoro-2-methoxyphenyl)-6-(1-methyl-1,2,3,6-tetrahydropyridin-4-yl)-7H-pyrrolo[2,3-d]pyrimidine;

4-(5-fluoro-2-methoxyphenyl)-6-[1-(methylsulfonyl)-1,2,3,6-tetrahydropyridin-4-yl]-7H-pyrrolo[2,3-d]pyrimidine;

1-{4-[4-(5-fluoro-2-methoxyphenyl)-7H-pyrrolo[2,3-d]pyrimidin-6-yl]-3,6-dihydropyridin-1(2H)-yl}ethanone;

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone;

6-[1-(cyclopropylsulfonyl)-1,2,3,6-tetrahydropyridin-4-yl]-4-(5-fluoro-2-methoxyphenyl)-7H-pyrrolo[2,3-d]pyrimidine;

N-benzyl-4-fluoro-3-[6-(piperidin-4-yl)-7H-pyrrolo[2,3-d]pyrimidin-4-yl]aniline;

4-(5-fluoro-2-methoxyphenyl)-6-[1-(propan-2-ylsulfonyl)-1,2,3,6-tetrahydropyridin-4-yl]-7H-pyrrolo[2,3-d]pyrimidine;

cyclopropyl{4-[4-(5-fluoro-2-methoxyphenyl)-7H-pyrrolo[2,3-d]pyrimidin-6-yl]-3,6-dihydropyridin-1(2H)-yl}methanone;

azetidin-2-yl{4-[4-(5-fluoro-2-methoxyphenyl)-7H-pyrrolo[2,3-d]pyrimidin-6-yl]-3,6-dihydropyridin-1(2H)-yl}methanone;

4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one;

5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one;

{4-[4-(5-fluoro-2-methoxyphenyl)-7H-pyrrolo[2,3-d]pyrimidin-6-yl]-3,6-dihydropyridin-1(2H)-yl}(tetrahydro-2H-pyran-3-yl)methanone;

(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone;

4-[4-(5-fluoro-2-methoxyphenyl)-7H-pyrrolo[2,3-d]pyrimidin-6-yl]-N-methyl-3,6-dihydropyridine-1(2H)-carboxamide;

1-{4-[4-(5-fluoro-2-methoxyphenyl)-7H-pyrrolo[2,3-d]pyrimidin-6-yl]-3,6-dihydropyridin-1(2H)-yl}-2-methoxyethanone;

4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide;

3-{4-[4-(5-fluoro-2-methoxyphenyl)-7H-pyrrolo[2,3-d]pyrimidin-6-yl]-3,6-dihydropyridin-1(2H)-yl}propane-1,2-diol;

6-(1-benzyl-1,2,3,6-tetrahydropyridin-4-yl)-4-(5-fluoro-2-methoxyphenyl)-7H-pyrrolo[2,3-d]pyrimidine;

4-({4-[4-(5-fluoro-2-methoxyphenyl)-7H-pyrrolo[2,3-d]pyrimidin-6-yl]-3,6-dihydropyridin-1(2H)-yl}methyl)benzonitrile;

3-({4-[4-(5-fluoro-2-methoxyphenyl)-7H-pyrrolo[2,3-d]pyrimidin-6-yl]-3,6-dihydropyridin-1(2H)-yl}methyl)benzonitrile;

4-(5-fluoro-2-methoxyphenyl)-6-[1-(tetrahydrofuran-2-yl-methyl)-1,2,3,6-tetrahydropyridin-4-yl]-7H-pyrrolo[2,3-d]pyrimidine;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide;

4-(5-fluoro-2-methoxyphenyl)-6-[1-(pyridin-2-ylmethyl)-1,2,3,6-tetrahydropyridin-4-yl]-7H-pyrrolo[2,3-d]pyrimidine;

4-(5-fluoro-2-methoxyphenyl)-6-[1-(pyridin-4-ylmethyl)-1,2,3,6-tetrahydropyridin-4-yl]-7H-pyrrolo[2,3-d]pyrimidine;

4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine;

N-benzyl-4-fluoro-3-{6-[1-(methylsulfonyl)-1,2,3,6-tetrahydropyridin-4-yl]-7H-pyrrolo[2,3-d]pyrimidin-4-yl}aniline;

4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

4-fluoro-3-{6-[1-(methylsulfonyl)-1,2,3,6-tetrahydropyridin-4-yl]-7H-pyrrolo[2,3-d]pyrimidin-4-yl}-N-(tetrahydrofuran-2-ylmethyl)aniline;

4-fluoro-3-{6-[1-(methylsulfonyl)-1,2,3,6-tetrahydropyridin-4-yl]-7H-pyrrolo[2,3-d]pyrimidin-4-yl}-N-(pyridin-2-ylmethyl)aniline;

4-(5-fluoro-2-methoxyphenyl)-6-[1-(pyridin-3-ylmethyl)-1,2,3,6-tetrahydropyridin-4-yl]-7H-pyrrolo[2,3-d]pyrimidine;

6-[1-(3-fluorobenzyl)-1,2,3,6-tetrahydropyridin-4-yl]-4-(5-fluoro-2-methoxyphenyl)-7H-pyrrolo[2,3-d]pyrimidine;

6-[1-(3,5-difluorobenzyl)-1,2,3,6-tetrahydropyridin-4-yl]-4-(5-fluoro-2-methoxyphenyl)-7H-pyrrolo[2,3-d]pyrimidine;

4-fluoro-3-{6-[1-(methylsulfonyl)-1,2,3,6-tetrahydropyridin-4-yl]-7H-pyrrolo[2,3-d]pyrimidin-4-yl}-N-(pyridin-4-ylmethyl)aniline;

6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine;

4-(5-fluoro-2-methoxyphenyl)-6-[1-(piperidin-4-ylmethyl)-1,2,3,6-tetrahydropyridin-4-yl]-7H-pyrrolo[2,3-d]pyrimidine;

4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine;

4-(5-chloro-2-fluoro-3-methylphenyl)-6-[1-(methylsulfonyl)-1,2,3,6-tetrahydropyridin-4-yl]-7H-pyrrolo[2,3-d]pyrimidine;

4-(2-butoxy-5-fluorophenyl)-6-[1-(methylsulfonyl)-1,2,3,6-tetrahydropyridin-4-yl]-7H-pyrrolo[2,3-d]pyrimidine;

4-[5-methyl-2-(propan-2-yloxy)phenyl]-6-[1-(methylsulfonyl)-1,2,3,6-tetrahydropyridin-4-yl]-7H-pyrrolo[2,3-d]pyrimidine;

4-(2-methoxy-5-methylphenyl)-6-[1-(methylsulfonyl)-1,2,3,6-tetrahydropyridin-4-yl]-7H-pyrrolo[2,3-d]pyrimidine;

4-(5-chloro-2-methoxyphenyl)-6-[1-(methylsulfonyl)-1,2,3,6-tetrahydropyridin-4-yl]-7H-pyrrolo[2,3-d]pyrimidine;

4-(2,4-difluorophenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethyl)phenyl]-7H-pyrrolo[2,3-d]pyrimidine;

N-(3-{6-[1-(methylsulfonyl)-1,2,3,6-tetrahydropyridin-4-yl]-7H-pyrrolo[2,3-d]pyrimidin-4-yl}phenyl)methanesulfonamide;

4-(5-fluoro-2-propoxyphenyl)-6-[1-(methylsulfonyl)-1,2,3,6-tetrahydropyridin-4-yl]-7H-pyrrolo[2,3-d]pyrimidine;

4-(2-fluoro-5-methylphenyl)-6-[1-(methylsulfonyl)-1,2,3,6-tetrahydropyridin-4-yl]-7H-pyrrolo[2,3-d]pyrimidine;

4-[2-fluoro-5-(trifluoromethyl)phenyl]-6-[1-(methylsulfonyl)-1,2,3,6-tetrahydropyridin-4-yl]-7H-pyrrolo[2,3-d]pyrimidine;

4-[2-fluoro-5-(propan-2-yloxy)phenyl]-6-[1-(methylsulfonyl)-1,2,3,6-tetrahydropyridin-4-yl]-7H-pyrrolo[2,3-d]pyrimidine;

4-(5-methyl-2-propoxyphenyl)-6-[1-(methylsulfonyl)-1,2,3,6-tetrahydropyridin-4-yl]-7H-pyrrolo[2,3-d]pyrimidine;

4-(5-butoxy-2-fluorophenyl)-6-[1-(methylsulfonyl)-1,2,3,6-tetrahydropyridin-4-yl]-7H-pyrrolo[2,3-d]pyrimidine;

4-(2-fluoro-3-methoxyphenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[3-(trifluoromethoxy)phenyl]-7H-pyrrolo[2,3-d]pyrimidine;

4-(1-methyl-1H-pyrazol-4-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethoxy)phenyl]-7H-pyrrolo[2,3-d]pyrimidine;

4-(4-methoxypyridin-3-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-(morpholin-4-yl)-7H-pyrrolo[2,3-d]pyrimidine;

6-(4,4-difluorocyclohex-1-en-1-yl)-4-(5-fluoro-2-methoxyphenyl)-7H-pyrrolo[2,3-d]pyrimidine;

6-[1-(methylsulfonyl)-1,2,3,6-tetrahydropyridin-4-yl]-4-(pyrrolidin-1-yl)-7H-pyrrolo[2,3-d]pyrimidine;

4-(4,4-difluoropiperidin-1-yl)-6-[1-(methylsulfonyl)-1,2,3,6-tetrahydropyridin-4-yl]-7H-pyrrolo[2,3-d]pyrimidine;

4-(3,3-difluoroazetidin-1-yl)-6-[1-(methylsulfonyl)-1,2,3,6-tetrahydropyridin-4-yl]-7H-pyrrolo[2,3-d]pyrimidine;

6-(3,6-dihydro-2H-pyran-4-yl)-4-(5-fluoro-2-methoxyphenyl)-7H-pyrrolo[2,3-d]pyrimidine;

tert-butyl 4-[4-(2-ethoxy-5-fluorophenyl)-7H-pyrrolo[2,3-d]pyrimidin-6-yl]-3,6-dihydropyridine-1(2H)-carboxylate;

4-(2-ethoxy-5-fluorophenyl)-6-(1,2,3,6-tetrahydropyridin-4-yl)-7H-pyrrolo[2,3-d]pyrimidine;

N-[4-({4-[4-(2-ethoxy-5-fluorophenyl)-7H-pyrrolo[2,3-d]pyrimidin-6-yl]-3,6-dihydropyridin-1(2H)-yl}methyl)phenyl]acetamide;

tert-butyl [4-({4-[4-(5-fluoro-2-methoxyphenyl)-7H-pyrrolo[2,3-d]pyrimidin-6-yl]-3,6-dihydropyridin-1(2H)-yl}methyl)phenyl]carbamate;

4-({4-[4-(5-fluoro-2-methoxyphenyl)-7H-pyrrolo[2,3-d]pyrimidin-6-yl]-3,6-dihydropyridin-1(2H)-yl}methyl)aniline;

methyl 4-({4-[4-(5-fluoro-2-methoxyphenyl)-7H-pyrrolo[2,3-d]pyrimidin-6-yl]-3,6-dihydropyridin-1(2H)-yl}methyl)benzoate;

4-({4-[4-(5-fluoro-2-methoxyphenyl)-7H-pyrrolo[2,3-d]pyrimidin-6-yl]-3,6-dihydropyridin-1(2H)-yl}methyl)benzoic acid;

methyl trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylate;

trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylic acid;

4-[4-(5-fluoro-2-methoxyphenyl)-7H-pyrrolo[2,3-d]pyrimidin-6-yl]-N,N-dimethyl-3,6-dihydropyridine-1(2H)-carboxamide;

4-[4-(2,3-difluorophenyl)-7H-pyrrolo[2,3-d]pyrimidin-6-yl]-N,N-dimethyl-3,6-dihydropyridine-1(2H)-carboxamide;
(2S)-cyclohexyl({4-[4-(5-fluoro-2-methoxyphenyl)-7H-pyrrolo[2,3-d]pyrimidin-6-yl]cyclohex-3-en-1-yl}amino)acetic acid;
N-{4-[4-(5-fluoro-2-methoxyphenyl)-7H-pyrrolo[2,3-d]pyrimidin-6-yl]cyclohex-3-en-1-yl}-L-valine;
4-[4-(5-fluoro-2-methoxyphenyl)-7H-pyrrolo[2,3-d]pyrimidin-6-yl]cyclohex-3-ene-1-carboxylic acid;
2-{4-[4-(5-fluoro-2-methoxyphenyl)-7H-pyrrolo[2,3-d]pyrimidin-6-yl]-3,6-dihydropyridin-1(2H)-yl}-N,N-dimethylacetamide;
N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]methanesulfonamide;
ethyl ({4-[4-(5-fluoro-2-methoxyphenyl)-7H-pyrrolo[2,3-d]pyrimidin-6-yl]-3,6-dihydropyridin-1(2H)-yl}sulfonyl)carbamate;
N-{4-[4-(5-fluoro-2-methoxyphenyl)-7H-pyrrolo[2,3-d]pyrimidin-6-yl]cyclohex-3-en-1-yl}-3-methyl-L-valine;
N-{4-[4-(5-fluoro-2-methoxyphenyl)-7H-pyrrolo[2,3-d]pyrimidin-6-yl]cyclohex-3-en-1-yl}-D-valine;
N-{4-[4-(5-fluoro-2-methoxyphenyl)-7H-pyrrolo[2,3-d]pyrimidin-6-yl]cyclohex-3-en-1-yl}-L-leucine;
4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid;
(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid; and pharmaceutically acceptable salts thereof.

Embodiments of Formula (IIa)

In one aspect, the present invention relates to compounds of Formula (IIa) or a pharmaceutically acceptable salt thereof,

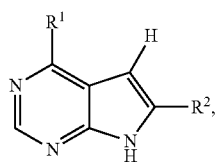
(IIa)

wherein
$R^1$ is selected from the group consisting of phenyl, 5 to 6 membered heteroaryl, 4 to 7 membered heterocycloalkyl and 4 to 7 membered heterocycloalkenyl; wherein the $R^1$ phenyl, 5 to 6 membered heteroaryl, 4 to 7 membered heterocycloalkyl and 4 to 7 membered heterocycloalkenyl are optionally substituted with one or more substituents selected from the group consisting of $R^{14}$, $OR^{14}$, $NHSO_2R^{14}$, halo, CN, and $NHR^{14}$;
$R^{14}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{14}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, $C(O)OH$, and $C(O)OR^{17}$;
$R^2$ is selected from the group consisting of cycloalkyl, cycloalkenyl, heterocycloalkyl and heterocycloalkenyl; wherein the $R^2$ cycloalkyl, cycloalkenyl, heterocloalkyl and heterocycloalkenyl are optionally substituted with one or more $R^{2A}$;
$R^{2A}$, at each occurrence, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, $C(O)OH$, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, 4 to 7 membered heterocycloalkenyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}$, $NHC(O)R^{10}$, $NR^{11}C(O)R^{10}$, $NHS(O)_2R^9$, $NR^{11}S(O)_2R^9$, $NHC(O)NH_2$, $NHC(O)NHR^{11}$, $NHC(O)NR^{11}R^{12}$, $NR^{11}C(O)NHR^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, $C(O)OH$, OH, CN, and halo;
$R^4$, at each occurrence, is independently selected from the group consisting of $C_1$-$C_5$ alkyl, $C_1$-$C_5$ alkenyl, aryl, 5 to 6 membered heteroaryl, 4 to 7 membered heterocycloalkyl, and $C_3$-$C_7$ cycloalkyl; wherein the $R^4$ $C_1$-$C_5$ alkyl and $C_1$-$C_5$ alkenyl are optionally substituted with one or more substituents selected from the group consisting of halo, $C_1$-$C_3$-haloalkyl, $C(O)OH$, CN, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, $C(O)OH$, CN, $NH_2$, $NHSO_2R^{17}$; $NHC(O)R^{17}$, $C(O)R^{17}$, $C(O)OR^{17}$, and $NHC(O)OR^{17}$;
$R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurrence, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^7$, $R^8$, $R^9$, $R^{10}$, $R^{11}$, $R^{12}$, $R^{13}$, $R^{14}$, $R^{15}$, $R^{16}$, and $R^{17}$ $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and
$R^{18}$, at each occurrence, is $C_1$-$C_6$ alkyl.

In one embodiment of Formula (IIa), $R^1$ is selected from the group consisting of phenyl, 5 to 6 membered heteroaryl, 4 to 7 membered heterocycloalkyl and 4 to 7 membered heterocycloalkenyl; wherein the $R^1$ phenyl, 5 to 6 membered heteroaryl, 4 to 7 membered heterocycloalkyl and 4 to 7 membered heterocycloalkenyl are optionally substituted with one or more substituents selected from the group consisting of $R^{14}$, $OR^{14}$, $NHSO_2R^{14}$, halo, CN, and $NHR^{14}$. In another embodiment of Formula (IIa), $R^1$ is selected from the group consisting of phenyl, 5 to 6 membered heteroaryl and 4 to 7 membered heterocycloalkyl; wherein the $R^1$ phenyl, 5 to 6 membered heteroaryl and 4 to 7 membered heterocycloalkyl are optionally substituted with one or more substituents selected from the group consisting of $R^{14}$, $OR^{14}$, $NHSO_2R^{14}$, halo, and $NHR^{14}$. In another embodiment of Formula (IIa), $R^1$ is phenyl; wherein the $R^1$ phenyl is optionally substituted with one or more substituents selected from the group consisting of $R^{14}$, $OR^{14}$, $NHSO_2R^{14}$, halo, and $NHR^{14}$. In another embodiment of Formula (IIa), $R^1$ is 5 to 6 membered heteroaryl; wherein the $R^1$ 5 to 6 membered heteroaryl is optionally substituted with one or more substituents selected from the group consisting of $R^{14}$, $OR^{14}$, $NHSO_2R^{14}$, halo, and $NHR^{14}$. In another embodiment of Formula (IIa), $R^1$ is 4 to 7 membered heterocycloalkyl; wherein the $R^1$ 4 to 7 membered heterocycloalkyl is optionally substituted with one or more substituents selected from the group consisting of $R^{14}$, $OR^{14}$, $NHSO_2R^{14}$, halo, and $NHR^{14}$.

In one embodiment of Formula (IIa), $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, $C(O)OH$, and $C(O)OR^{17}$. In another one embodiment of Formula (IIa), $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with CN.

In one embodiment of Formula (IIa), $R^2$ is selected from the group consisting of cycloalkyl, cycloalkenyl, heterocycloalkyl and heterocycloalkenyl; wherein the $R^2$ cycloalkyl, cycloalkenyl, heterocycloalkyl and heterocycloalkenyl are optionally substituted with one or more $R^{2A}$. In another embodiment of Formula (IIa), $R^2$ is selected from the group consisting of cycloalkenyl, heterocycloalkyl and heterocycloalkenyl; wherein the $R^2$ cycloalkyl, heterocycloalkyl and heterocycloalkenyl are optionally substituted with one or more $R^{2A}$. In another embodiment of Formula (IIa), $R^2$ is cycloalkenyl; wherein the $R^2$ cycloalkenyl is optionally substituted with one or more $R^{2A}$. In another embodiment of Formula (IIa), $R^2$ is heterocycloalkyl; wherein the $R^2$ heterocycloalkyl is optionally substituted with one or more $R^{2A}$. In another embodiment of Formula (IIa), $R^2$ is heterocycloalkenyl; wherein the $R^2$ heterocycloalkenyl is optionally substituted with one or more $R^{2A}$.

In one embodiment of Formula (IIa), $R^{2A}$, at each occurrence, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, $C(O)OH$, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}$, $NHC(O)R^{10}$, $NR^{11}C(O)R^{10}$, $NHS(O)_2R^9$, $NR^{11}S(O)_2R^9$, $NHC(O)NH_2$, $NHC(O)NHR^{11}$, $NHC(O)NR^{11}R^{12}$, $N^{11}C(O)NHR^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, $C(O)OH$, OH, CN, and halo. In another embodiment of Formula (IIa), $R^{2A}$, at each occurrence, is independently selected from the group consisting of halo, $NHR^5$, $SO_2R^7$, $SO_2NHC(O)OR^8$, $C(O)R^8$, $C(O)OR^8$, $C(O)OH$, $C(O)NHR^5$, $C(O)NR^5R^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and OH.

In one embodiment of Formula (IIa), $R^4$, at each occurrence, is independently selected from the group consisting of $C_1$-$C_5$ alkyl, $C_1$-$C_5$ alkenyl, aryl, 5 to 6 membered heteroaryl, 4 to 7 membered heterocycloalkyl, and $C_3$-$C_7$ cycloalkyl; wherein the $R^4C_1$-$C_5$ alkyl and $C_1$-$C_5$ alkenyl are optionally substituted with one or more substituents selected from the group consisting of halo, $C_1$-$C_3$-haloalkyl, $C(O)OH$, CN, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, $C(O)OH$, CN, $NH_2$, $NHSO_2R^{17}$, $NHC(O)R^{17}$, $C(O)R^{17}$, $C(O)OR^{17}$, and $NHC(O)OR^{17}$. In another embodiment of Formula (IIa), $R^4$, at each occurrence, is independently selected from the group consisting of $C_1$-$C_5$ alkyl, aryl, 5 to 6 membered heteroaryl, and 4 to 7 membered heterocycloalkyl; wherein the $R^4C_1$-$C_5$ alkyl is optionally substituted with one or more $C(O)OH$; wherein the $R^4$ aryl, 5 to 6 membered heteroaryl, and 4 to 7 membered heterocycloalkyl are optionally substituted with one or more substituents selected from the group consisting of halo, $C_1$-$C_3$-haloalkyl, $C(O)OH$, CN, $NH_2$, $NHSO_2R^{17}$; $NHC(O)R^{17}$, $C(O)OR^{17}$, and $NHC(O)OR^{17}$.

In one embodiment of Formula (IIa), $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurrence, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurrence, is $C_1$-$C_6$ alkyl. In another embodiment of Formula (IIa), $R^5$, $R^6$, $R^7$, $R^8$, $R^{11}$, $R^{12}$, and $R^{17}$, at each occurrence, are independently selected from the group consisting of $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl; wherein the $R^5$, $R^6$, $R^7$, $R^8$, $R^{11}$, $R^{12}$, and $R^{17}C_6$ alkyl, $C_1$-$C_3$-haloalkyl, $C_2$-$C_5$ alkenyl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurrence, is $C_1$-$C_6$ alkyl.

In one embodiment of Formula (IIa),
$R^1$ is selected from the group consisting of phenyl, 5 to 6 membered heteroaryl, and 4 to 7 membered heterocycloalkyl; wherein the $R^1$ phenyl, 5 to 6 membered heteroaryl, and 4 to 7 membered heterocycloalkyl are optionally substituted with one or more substituents selected from the group consisting of $R^{14}$, $OR^{14}$, $NHSO_2R^{14}$, halo, and $NHR^{14}$;
$R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three CN;

R² is selected from the group consisting of cycloalkenyl, heterocycloalkyl and heterocycloalkenyl; wherein the R² cycloalkenyl, heterocycloalkyl and heterocycloalkenyl are optionally substituted with one or more $R^{2,4}$;

$R^{2,4}$, at each occurrence, is independently selected from the group consisting of halo, $NHR^5$, $SO_2R^7$, $SO_2NHC(O)OR^8$, $C(O)R^8$, $C(O)OR^8$, $C(O)OH$, $C(O)NHR^5$, $C(O)NR^5R^6$, $C_1$-$C_5$ alkyl, and $C_3$-$C_7$ cycloalkyl; wherein the $R^{2,4}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and OH;

$R^4$, at each occurrence, is independently selected from the group consisting of $C_1$-$C_5$ alkyl, aryl, 5 to 6 membered heteroaryl, and 4 to 7 membered heterocycloalkyl; wherein the $R^4$ $C_1$-$C_5$ alkyl is optionally substituted with one or more $C(O)OH$; wherein the $R^4$ aryl, 5 to 6 membered heteroaryl, and 4 to 7 membered heterocycloalkyl are optionally substituted with one or more substituents selected from the group consisting of halo, $C_1$-$C_3$-haloalkyl, $C(O)OH$, CN, $NH_2$, $NHSO_2R^{17}$; $NHC(O)R^{17}$, $C(O)OR^{17}$, and $NHC(O)OR^{17}$;

$R^5$, $R^6$, $R^7$, $R^8$, $R^{11}$, $R^{12}$, and $R^{17}$, at each occurrence, are independently selected from the group consisting of $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl; wherein the $R^5$, $R^6$, $R^7$, $R^8$, $R^{11}$, $R^{12}$, and $R^{17}$ $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurrence, is $C_1$-$C_6$ alkyl.

Still another embodiment pertains to compounds of Formula (IIa), selected from the group consisting of 4-(5-fluoro-2-methoxyphenyl)-6-(piperidin-4-yl)-7H-pyrrolo[2,3-d]pyrimidine;

4-(5-fluoro-2-methoxyphenyl)-6-(1-methylpiperidin-4-yl)-7H-pyrrolo[2,3-d]pyrimidine;

4-(5-fluoro-2-methoxyphenyl)-6-(1,2,3,6-tetrahydropyridin-4-yl)-7H-pyrrolo[2,3-d]pyrimidine;

4-(5-fluoro-2-methoxyphenyl)-6-[1-methyl-1,2,3,6-tetrahydropyridin-4-yl]-7H-pyrrolo[2,3-d]pyrimidine;

4-(5-fluoro-2-methoxyphenyl)-6-[1-(methylsulfonyl)-1,2,3,6-tetrahydropyridin-4-yl]-7H-pyrrolo[2,3-d]pyrimidine;

1-{4-[4-(5-fluoro-2-methoxyphenyl)-7H-pyrrolo[2,3-d]pyrimidin-6-yl]-3,6-dihydropyridin-1(2H)-yl}ethanone;

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone;

6-[1-(cyclopropylsulfonyl)-1,2,3,6-tetrahydropyridin-4-yl]-4-(5-fluoro-2-methoxyphenyl)-7H-pyrrolo[2,3-d]pyrimidine;

N-benzyl-4-fluoro-3-[6-(piperidin-4-yl)-7H-pyrrolo[2,3-d]pyrimidin-4-yl]aniline;

4-(5-fluoro-2-methoxyphenyl)-6-[1-(propan-2-ylsulfonyl)-1,2,3,6-tetrahydropyridin-4-yl]-7H-pyrrolo[2,3-d]pyrimidine;

cyclopropyl{4-[4-(5-fluoro-2-methoxyphenyl)-7H-pyrrolo[2,3-d]pyrimidin-6-yl]-3,6-dihydropyridin-1(2H)-yl}methanone;

azetidin-2-yl{4-[4-(5-fluoro-2-methoxyphenyl)-7H-pyrrolo[2,3-d]pyrimidin-6-yl]-3,6-dihydropyridin-1(2H)-yl}methanone;

4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one;

5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one;

{4-[4-(5-fluoro-2-methoxyphenyl)-7H-pyrrolo[2,3-d]pyrimidin-6-yl]-3,6-dihydropyridin-1(2H)-yl}(tetrahydro-2H-pyran-3-yl)methanone;

(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone;

4-[4-(5-fluoro-2-methoxyphenyl)-7H-pyrrolo[2,3-d]pyrimidin-6-yl]-N-methyl-3,6-dihydropyridine-1(2H)-carboxamide;

1-{4-[4-(5-fluoro-2-methoxyphenyl)-7H-pyrrolo[2,3-d]pyrimidin-6-yl]-3,6-dihydropyridin-1(2H)-yl}-2-methoxyethanone;

4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide;

3-{4-[4-(5-fluoro-2-methoxyphenyl)-7H-pyrrolo[2,3-d]pyrimidin-6-yl]-3,6-dihydropyridin-1(2H)-yl}propane-1,2-diol;

6-(1-benzyl-1,2,3,6-tetrahydropyridin-4-yl)-4-(5-fluoro-2-methoxyphenyl)-7H-pyrrolo[2,3-d]pyrimidine;

4-({4-[4-(5-fluoro-2-methoxyphenyl)-7H-pyrrolo[2,3-d]pyrimidin-6-yl]-3,6-dihydropyridin-1(2H)-yl}methyl)benzonitrile;

3-({4-[4-(5-fluoro-2-methoxyphenyl)-7H-pyrrolo[2,3-d]pyrimidin-6-yl]-3,6-dihydropyridin-1(2H)-yl}methyl)benzonitrile;

4-(5-fluoro-2-methoxyphenyl)-6-[1-(tetrahydrofuran-2-ylmethyl)-1,2,3,6-tetrahydropyridin-4-yl]-7H-pyrrolo[2,3-d]pyrimidine;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide;

4-(5-fluoro-2-methoxyphenyl)-6-[1-(pyridin-2-ylmethyl)-1,2,3,6-tetrahydropyridin-4-yl]-7H-pyrrolo[2,3-d]pyrimidine;

4-(5-fluoro-2-methoxyphenyl)-6-[1-(pyridin-4-ylmethyl)-1,2,3,6-tetrahydropyridin-4-yl]-7H-pyrrolo[2,3-d]pyrimidine;

4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine;

N-benzyl-4-fluoro-3-{6-[1-(methylsulfonyl)-1,2,3,6-tetrahydropyridin-4-yl]-7H-pyrrolo[2,3-d]pyrimidin-4-yl}aniline;

4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

4-fluoro-3-{6-[1-(methylsulfonyl)-1,2,3,6-tetrahydropyridin-4-yl]-7H-pyrrolo[2,3-d]pyrimidin-4-yl}-N-(tetrahydrofuran-2-ylmethyl)aniline;

4-fluoro-3-{6-[1-(methylsulfonyl)-1,2,3,6-tetrahydropyridin-4-yl]-7H-pyrrolo[2,3-d]pyrimidin-4-yl}-N-(pyridin-2-ylmethyl)aniline;

4-(5-fluoro-2-methoxyphenyl)-6-[1-(pyridin-3-ylmethyl)-1,2,3,6-tetrahydropyridin-4-yl]-7H-pyrrolo[2,3-d]pyrimidine;

6-[1-(3-fluorobenzyl)-1,2,3,6-tetrahydropyridin-4-yl]-4-(5-fluoro-2-methoxyphenyl)-7H-pyrrolo[2,3-d]pyrimidine;

6-[1-(3,5-difluorobenzyl)-1,2,3,6-tetrahydropyridin-4-yl]-4-(5-fluoro-2-methoxyphenyl)-7H-pyrrolo[2,3-d]pyrimidine;

4-fluoro-3-{6-[1-(methylsulfonyl)-1,2,3,6-tetrahydropyridin-4-yl]-7H-pyrrolo[2,3-d]pyrimidin-4-yl}-N-(pyridin-4-ylmethyl)aniline;

6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine;

4-(5-fluoro-2-methoxyphenyl)-6-[1-(piperidin-4-ylmethyl)-1,2,3,6-tetrahydropyridin-4-yl]-7H-pyrrolo[2,3-d]pyrimidine;

4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine;

4-(5-chloro-2-fluoro-3-methylphenyl)-6-[1-(methylsulfonyl)-1,2,3,6-tetrahydropyridin-4-yl]-7H-pyrrolo[2,3-d]pyrimidine;

4-(2-butoxy-5-fluorophenyl)-6-[1-(methylsulfonyl)-1,2,3,6-tetrahydropyridin-4-yl]-7H-pyrrolo[2,3-d]pyrimidine;

4-[5-methyl-2-(propan-2-yloxy)phenyl]-6-[1-(methylsulfonyl)-1,2,3,6-tetrahydropyridin-4-yl]-7H-pyrrolo[2,3-d]pyrimidine;

4-(2-methoxy-5-methylphenyl)-6-[1-(methylsulfonyl)-1,2,3,6-tetrahydropyridin-4-yl]-7H-pyrrolo[2,3-d]pyrimidine;

4-(5-chloro-2-methoxyphenyl)-6-[1-(methylsulfonyl)-1,2,3,6-tetrahydropyridin-4-yl]-7H-pyrrolo[2,3-d]pyrimidine;

4-(2,4-difluorophenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethyl)phenyl]-7H-pyrrolo[2,3-d]pyrimidine;

N-(3-{6-[1-(methylsulfonyl)-1,2,3,6-tetrahydropyridin-4-yl]-7H-pyrrolo[2,3-d]pyrimidin-4-yl}phenyl)methanesulfonamide;

4-(5-fluoro-2-propoxyphenyl)-6-[1-(methylsulfonyl)-1,2,3,6-tetrahydropyridin-4-yl]-7H-pyrrolo[2,3-d]pyrimidine;

4-(2-fluoro-5-methylphenyl)-6-[1-(methylsulfonyl)-1,2,3,6-tetrahydropyridin-4-yl]-7H-pyrrolo[2,3-d]pyrimidine;

4-[2-fluoro-5-(trifluoromethyl)phenyl]-6-[1-(methylsulfonyl)-1,2,3,6-tetrahydropyridin-4-yl]-7H-pyrrolo[2,3-d]pyrimidine;

4-[2-fluoro-5-(propan-2-yloxy)phenyl]-6-[1-(methylsulfonyl)-1,2,3,6-tetrahydropyridin-4-yl]-7H-pyrrolo[2,3-d]pyrimidine;

4-(5-methyl-2-propoxyphenyl)-6-[1-(methylsulfonyl)-1,2,3,6-tetrahydropyridin-4-yl]-7H-pyrrolo[2,3-d]pyrimidine;

4-(5-butoxy-2-fluorophenyl)-6-[1-(methylsulfonyl)-1,2,3,6-tetrahydropyridin-4-yl]-7H-pyrrolo[2,3-d]pyrimidine;

4-(2-fluoro-3-methoxyphenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[3-(trifluoromethoxy)phenyl]-7H-pyrrolo[2,3-d]pyrimidine;

4-(1-methyl-1H-pyrazol-4-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethoxy)phenyl]-7H-pyrrolo[2,3-d]pyrimidine;

4-(4-methoxypyridin-3-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-(morpholin-4-yl)-7H-pyrrolo[2,3-d]pyrimidine;

6-(4,4-difluorocyclohex-1-en-1-yl)-4-(5-fluoro-2-methoxyphenyl)-7H-pyrrolo[2,3-d]pyrimidine;

6-[1-(methylsulfonyl)-1,2,3,6-tetrahydropyridin-4-yl]-4-(pyrrolidin-1-yl)-7H-pyrrolo[2,3-d]pyrimidine;

4-(4,4-difluoropiperidin-1-yl)-6-[1-(methylsulfonyl)-1,2,3,6-tetrahydropyridin-4-yl]-7H-pyrrolo[2,3-d]pyrimidine;

4-(3,3-difluoroazetidin-1-yl)-6-[1-(methylsulfonyl)-1,2,3,6-tetrahydropyridin-4-yl]-7H-pyrrolo[2,3-d]pyrimidine;

6-(3,6-dihydro-2H-pyran-4-yl)-4-(5-fluoro-2-methoxyphenyl)-7H-pyrrolo[2,3-d]pyrimidine;

tert-butyl 4-[4-(2-ethoxy-5-fluorophenyl)-7H-pyrrolo[2,3-d]pyrimidin-6-yl]-3,6-dihydropyridine-1(2H)-carboxylate;

4-(2-ethoxy-5-fluorophenyl)-6-(1,2,3,6-tetrahydropyridin-4-yl)-7H-pyrrolo[2,3-d]pyrimidine;

N-[4-({4-[4-(2-ethoxy-5-fluorophenyl)-7H-pyrrolo[2,3-d]pyrimidin-6-yl]-3,6-dihydropyridin-1(2H)-yl}methyl)phenyl]acetamide;

tert-butyl [4-({4-[4-(5-fluoro-2-methoxyphenyl)-7H-pyrrolo[2,3-d]pyrimidin-6-yl]-3,6-dihydropyridin-1(2H)-yl}methyl)phenyl]carbamate;

4-({4-[4-(5-fluoro-2-methoxyphenyl)-7H-pyrrolo[2,3-d]pyrimidin-6-yl]-3,6-dihydropyridin-1(2H)-yl}methyl)aniline;

methyl 4-({4-[4-(5-fluoro-2-methoxyphenyl)-7H-pyrrolo[2,3-d]pyrimidin-6-yl]-3,6-dihydropyridin-1(2H)-yl}methyl)benzoate;

4-({4-[4-(5-fluoro-2-methoxyphenyl)-7H-pyrrolo[2,3-d]pyrimidin-6-yl]-3,6-dihydropyridin-1(2H)-yl}methyl)benzoic acid;

methyl trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylate;

trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylic acid;

4-[4-(5-fluoro-2-methoxyphenyl)-7H-pyrrolo[2,3-d]pyrimidin-6-yl]-N,N-dimethyl-3,6-dihydropyridine-1(2H)-carboxamide;

4-[4-(2,3-difluorophenyl)-7H-pyrrolo[2,3-d]pyrimidin-6-yl]-N,N-dimethyl-3,6-dihydropyridine-1(2H)-carboxamide;

(2S)-cyclohexyl({4-[4-(5-fluoro-2-methoxyphenyl)-7H-pyrrolo[2,3-d]pyrimidin-6-yl]cyclohex-3-en-1-yl}amino)acetic acid;

N-{4-[4-(5-fluoro-2-methoxyphenyl)-7H-pyrrolo[2,3-d]pyrimidin-6-yl]cyclohex-3-en-1-yl}-L-valine;

4-[4-(5-fluoro-2-methoxyphenyl)-7H-pyrrolo[2,3-d]pyrimidin-6-yl]cyclohex-3-ene-1-carboxylic acid;

2-{4-[4-(5-fluoro-2-methoxyphenyl)-7H-pyrrolo[2,3-d]pyrimidin-6-yl]-3,6-dihydropyridin-1(2H)-yl}-N,N-dimethylacetamide;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]methanesulfonamide;

ethyl ({4-[4-(5-fluoro-2-methoxyphenyl)-7H-pyrrolo[2,3-d]pyrimidin-6-yl]-3,6-dihydropyridin-1(2H)-yl}sulfonyl)carbamate;

N-{4-[4-(5-fluoro-2-methoxyphenyl)-7H-pyrrolo[2,3-d]pyrimidin-6-yl]cyclohex-3-en-1-yl}-3-methyl-L-valine;

N-{4-[4-(5-fluoro-2-methoxyphenyl)-7H-pyrrolo[2,3-d]pyrimidin-6-yl]cyclohex-3-en-1-yl}-D-valine;

N-{4-[4-(5-fluoro-2-methoxyphenyl)-7H-pyrrolo[2,3-d]pyrimidin-6-yl]cyclohex-3-en-1-yl}-L-leucine;

4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid;

(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid; and pharmaceutically acceptable salts thereof.

Embodiments of Formula (IIIa)

In one aspect, the present invention relates to compounds of Formula (IIIa) or a pharmaceutically acceptable salt thereof,

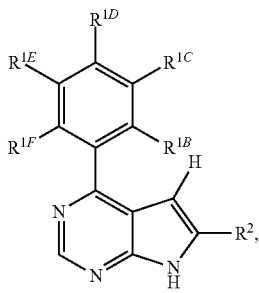

(IIIa)

wherein
- $R^{1B}$, $R^{1C}$, $R^{1D}$, $R^{1E}$, and $R^{1F}$ are each independently selected from the group consisting of H, $R^{1A}$, $OR^{1A}$, $NHSO_2R^{1A}$, halo, CN, and $NHR^{1A}$;
- $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, $C(O)OH$, and $C(O)OR^{17}$;
- $R^2$ is selected from the group consisting of cycloalkyl, cycloalkenyl, heterocycloalkyl and heterocycloalkenyl; wherein the $R^2$ cycloalkyl, cycloalkenyl, heterocycloalkyl and heterocycloalkenyl are optionally substituted with one or more $R^{2A}$;
- $R^{2A}$, at each occurrence, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, $C(O)OH$, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, 4 to 7 membered heterocycloalkenyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}$, $NHC(O)R^{10}$, $NR^{11}C(O)R^{10}$, $NHS(O)_2R^9$, $NR^{11}S(O)_2R^9$, $NHC(O)NH_2$, $NHC(O)NHR^{11}$, $NHC(O)NR^{11}R^{12}$, $NR^{11}C(O)NHR^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, $C(O)OH$, OH, CN, and halo;
- $R^4$, at each occurrence, is independently selected from the group consisting of $C_1$-$C_5$ alkyl, $C_1$-$C_5$ alkenyl, aryl, 5 to 6 membered heteroaryl, 4 to 7 membered heterocycloalkyl, and $C_3$-$C_7$ cycloalkyl; wherein the $R^4$ $C_1$-$C_5$ alkyl and $C_1$-$C_5$ alkenyl are optionally substituted with one or more substituents selected from the group consisting of halo, $C_1$-$C_3$-haloalkyl, $C(O)OH$, CN, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, $C(O)OH$, CN, $NH_2$, $NHSO_2R^{17}$; $NHC(O)R^{17}$, $C(O)R^{17}$, $C(O)OR^{17}$, and $NHC(O)OR^{17}$;
- $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurrence, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^7$, $R^8$, $R^9$, $R^{10}$, $R^{11}$, $R^{12}$, $R^{13}$, $R^{14}$, $R^{15}$, $R^{16}$, and $R^{17}$ $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and
- $R^{18}$, at each occurrence, is $C_1$-$C_6$ alkyl.

In one embodiment of Formula (IIIa), $R^{1B}$, $R^{1C}$, $R^{1D}$, $R^{1E}$, and $R^{1F}$ are each independently selected from the group consisting of H, $R^{1A}$, $OR^{1A}$, $NHSO_2R^{1A}$, halo, CN, and $NHR^{1A}$. In another embodiment of Formula (IIIa), at least one of $R^{1B}$, $R^{1C}$, $R^{1D}$, $R^{1E}$, and $R^{1F}$ are independently selected from the group consisting of $R^{1A}$, $OR^{1A}$, $NHSO_2R^{1A}$, halo, CN, and $NHR^{1A}$; and the remainder are H. In another one embodiment of Formula (IIIa), $R^{1B}$ is independently selected from the group consisting of H, $OR^{1A}$, and halo, CN, and $NHR^{1A}$; $R^{1c}$ is independently selected selected from the group consisting of H, $R^{1A}$, $OR^{1A}$, $NHSO_2R^{1A}$, halo, and $NHR^{1A}$; $R^{1D}$ is independently selected from the group consisting of H and halo; $R^{1E}$ is independently selected selected from the group consisting of H, $OR^{1A}$, and halo; and $R^{1F}$ is independently selected from the group consisting of H, $R^{1A}$, $OR^{1A}$, and halo. In another one embodiment of Formula (IIIa), $R^{1B}$ is H; $R^{1C}$ is halo; $R^{1D}$ is H; $R^{1E}$ is H; and $R^{1F}$ is $OR^{1A}$. In another one embodiment of Formula (IIIa), $R^{1B}$ is H; $R^{1c}$ is F; $R^{1D}$ is H; $R^{1E}$ is H; and $R^{1F}$ is $OCH_3$.

In one embodiment of Formula (IIIa), $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, $C(O)OH$, and $C(O)OR^{17}$. In another one embodiment of Formula (IIIa), $R^{1A}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with CN.

In one embodiment of Formula (IIIa), $R^2$ is selected from the group consisting of cycloalkyl, cycloalkenyl, heterocycloalkyl and heterocycloalkenyl; wherein the $R^2$ cycloalkyl, cycloalkenyl, heterocycloalkyl and heterocycloalkenyl are optionally substituted with one or more $R^{2A}$. In another embodiment of Formula (IIIa), $R^2$ is selected from the group consisting of cycloalkenyl, heterocycloalkyl and heterocycloalkenyl; wherein the $R^2$ cycloalkenyl, heterocycloalkyl and heterocycloalkenyl are optionally substituted with one or more $R^{2A}$. In another embodiment of Formula (IIIa), $R^2$ is cycloalkenyl; wherein the $R^2$ cycloalkenyl is optionally substituted with one or more $R^{2A}$. In another embodiment of Formula (IIIa), $R^2$ is heterocycloalkyl; wherein the $R^2$ heterocycloalkyl is optionally substituted with one or more $R^{2A}$. In another embodiment of Formula (IIIa), $R^2$ is heterocycloalkenyl; wherein the $R^2$ heterocycloalkenyl is optionally substituted with one or more $R^{2A}$.

In one embodiment of Formula (IIIa), $R^{2A}$, at each occurrence, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, $C(O)OH$, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, 4 to 7 membered heterocycloalkenyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}$, $NHC(O)R^{10}$, $NR^{11}C(O)R^{10}$, $NHS(O)_2R^9$, $NR^{11}S(O)_2R^9$, $NHC(O)NH_2$, $NHC(O)NHR^{11}$, $NHC(O)NR^{11}R^{12}$, $NHC(O)NR^{11}R^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, $C(O)OH$, $OH$, $CN$, and halo. In another embodiment of Formula (IIIa), $R^{2A}$, at each occurrence, is independently selected from the group consisting of halo, $NHR^5$, $SO_2R^7$, $SO_2NHC(O)OR^8$, $C(O)R^8$, $C(O)OR^8$, $C(O)OH$, $C(O)NHR^5$, $C(O)NR^5R^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and $OH$.

In one embodiment of Formula (IIIa), $R^4$, at each occurrence, is independently selected from the group consisting of $C_1$-$C_5$ alkyl, $C_1$-$C_5$ alkenyl, aryl, 5 to 6 membered heteroaryl, 4 to 7 membered heterocycloalkyl, and $C_3$-$C_7$ cycloalkyl; wherein the $R^4 C_1$-$C_5$ alkyl and $C_1$-$C_5$ alkenyl are optionally substituted with one or more substituents selected from the group consisting of halo, $C_1$-$C_3$-haloalkyl, $C(O)OH$, $CN$, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, $C(O)OH$, $CN$, $NH_2$, $NHSO_2R^{17}$; $NHC(O)R^{17}$, $C(O)R^{17}$, $C(O)OR^{17}$, and $NHC(O)OR^{17}$. In another embodiment of Formula (IIIa), $R^4$, at each occurrence, is independently selected from the group consisting of $C_1$-$C_5$ alkyl, aryl, 5 to 6 membered heteroaryl, and 4 to 7 membered heterocycloalkyl; wherein the $R^4 C_1$-$C_5$ alkyl is optionally substituted with one or more $C(O)OH$; wherein the $R^4$ aryl, 5 to 6 membered heteroaryl, and 4 to 7 membered heterocycloalkyl are optionally substituted with one or more substituents selected from the group consisting of halo, $C_1$-$C_3$-haloalkyl, $C(O)OH$, $CN$, $NH_2$, $NHSO_2R^{17}$; $NHC(O)R^{17}$, $C(O)OR^{17}$, and $NHC(O)OR^{17}$.

In one embodiment of Formula (IIIa), $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurrence, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ $C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurrence, is $C_1$-$C_6$ alkyl. In another embodiment of Formula (IIIa), $R^5$, $R^6$, $R^7$, $R^8$, $R^{11}$, $R^{12}$, and $R^{17}$, at each occurrence, are independently selected from the group consisting of $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl; wherein the $R^5$, $R^6$, $R^7$, $R^8$, $R^{11}$, $R^{12}$, and $R^{17}$ $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurrence, is $C_1$-$C_6$ alkyl.

In one embodiment of Formula (IIIa), $R^{1B}$, $R^{1C}$, $R^{1D}$, $R^{1E}$, and $R^{1F}$ are each independently selected from the group consisting of H, $R^{14}$, $OR^{14}$, $NHSO_2R^{14}$, halo, and $NHR^{14}$;

$R^{14}$, at each occurrence, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{14}$ phenyl, 5 to 6 membered heteroaryl, and 4 to 7 membered heterocycloalkyl rings are optionally substituted with one to three CN;

$R^2$ is selected from the group consisting of cycloalkenyl, heterocycloalkyl and heterocycloalkenyl; wherein the $R^2$ cycloalkenyl, heterocycloalkyl and heterocycloalkenyl are optionally substituted with one or more $R^{2A}$;

$R^{2A}$, at each occurrence, is independently selected from the group consisting of halo, $NHR^5$, $SO_2R^7$, $SO_2NHC(O)OR^8$, $C(O)R^8$, $C(O)OR^8$, $C(O)OH$, $C(O)NHR^5$, $C(O)NR^5R^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and $OH$;

$R^4$, at each occurrence, is independently selected from the group consisting of $C_1$-$C_5$ alkyl, aryl, 5 to 6 membered heteroaryl, and 4 to 7 membered heterocycloalkyl; wherein the $R^4 C_1$-$C_5$ alkyl is optionally substituted with one or more $C(O)OH$; wherein the $R^4$ aryl, 5 to 6 membered heteroaryl, and 4 to 7 membered heterocycloalkyl are optionally substituted with one or more substituents selected from the group consisting of halo, $C_1$-$C_3$-haloalkyl, $C(O)OH$, $CN$, $NH_2$, $NHSO_2R^{17}$; $NHC(O)R^{17}$, $C(O)OR^{17}$, and $NHC(O)OR^{17}$;

$R^5$, $R^6$, $R^7$, $R^8$, $R^{11}$, $R^{12}$, and $R^{17}$, at each occurrence, are independently selected from the group consisting of $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl; wherein the $R^5$, $R^6$, $R^7$, $R^8$, $R^{11}$, $R^{12}$, and $R^{17}$ $C_1$-$C_6$ alkyl, $C_1$-$C_3$-haloalkyl, $C_2$-$C_5$ alkenyl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurrence, is $C_1$-$C_6$ alkyl.

Still another embodiment pertains to compounds of Formula (IIIa), selected from the group consisting of 4-(5-fluoro-2-methoxyphenyl)-6-(piperidin-4-yl)-7H-pyrrolo[2,3-d]pyrimidine;

4-(5-fluoro-2-methoxyphenyl)-6-(1-methylpiperidin-4-yl)-7H-pyrrolo[2,3-d]pyrimidine;

4-(5-fluoro-2-methoxyphenyl)-6-(1,2,3,6-tetrahydropyridin-4-yl)-7H-pyrrolo[2,3-d]pyrimidine;

4-(5-fluoro-2-methoxyphenyl)-6-(1-methyl-1,2,3,6-tetrahydropyridin-4-yl)-7H-pyrrolo[2,3-d]pyrimidine;

4-(5-fluoro-2-methoxyphenyl)-6-[1-(methylsulfonyl)-1,2,3,6-tetrahydropyridin-4-yl]-7H-pyrrolo[2,3-d]pyrimidine;

1-{4-[4-(5-fluoro-2-methoxyphenyl)-7H-pyrrolo[2,3-d]pyrimidin-6-yl]-3,6-dihydropyridin-1(2H)-yl}ethanone;

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone;
6-[1-(cyclopropylsulfonyl)-1,2,3,6-tetrahydropyridin-4-yl]-4-(5-fluoro-2-methoxyphenyl)-7H-pyrrolo[2,3-d]pyrimidine;
N-benzyl-4-fluoro-3-[6-(piperidin-4-yl)-7H-pyrrolo[2,3-d]pyrimidin-4-yl]aniline;
4-(5-fluoro-2-methoxyphenyl)-6-[1-(propan-2-ylsulfonyl)-1,2,3,6-tetrahydropyridin-4-yl]-7H-pyrrolo[2,3-d]pyrimidine;
cyclopropyl{4-[4-(5-fluoro-2-methoxyphenyl)-7H-pyrrolo[2,3-d]pyrimidin-6-yl]-3,6-dihydropyridin-1(2H)-yl}methanone;
azetidin-2-yl{4-[4-(5-fluoro-2-methoxyphenyl)-7H-pyrrolo[2,3-d]pyrimidin-6-yl]-3,6-dihydropyridin-1(2H)-yl}methanone;
4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one;
5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one;
{4-[4-(5-fluoro-2-methoxyphenyl)-7H-pyrrolo[2,3-d]pyrimidin-6-yl]-3,6-dihydropyridin-1(2H)-yl}(tetrahydro-2H-pyran-3-yl)methanone;
(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone;
4-[4-(5-fluoro-2-methoxyphenyl)-7H-pyrrolo[2,3-d]pyrimidin-6-yl]-N-methyl-3,6-dihydropyridine-1(2H)-carboxamide;
1-{4-[4-(5-fluoro-2-methoxyphenyl)-7H-pyrrolo[2,3-d]pyrimidin-6-yl]-3,6-dihydropyridin-1(2H)-yl}-2-methoxyethanone;
4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide;
3-{4-[4-(5-fluoro-2-methoxyphenyl)-7H-pyrrolo[2,3-d]pyrimidin-6-yl]-3,6-dihydropyridin-1(2H)-yl}propane-1,2-diol;
6-(1-benzyl-1,2,3,6-tetrahydropyridin-4-yl)-4-(5-fluoro-2-methoxyphenyl)-7H-pyrrolo[2,3-d]pyrimidine;
4-({4-[4-(5-fluoro-2-methoxyphenyl)-7H-pyrrolo[2,3-d]pyrimidin-6-yl]-3,6-dihydropyridin-1(2H)-yl}methyl)benzonitrile;
3-({4-[4-(5-fluoro-2-methoxyphenyl)-7H-pyrrolo[2,3-d]pyrimidin-6-yl]-3,6-dihydropyridin-1(2H)-yl}methyl)benzonitrile;
4-(5-fluoro-2-methoxyphenyl)-6-[1-(tetrahydro furan-2-ylmethyl)-1,2,3,6-tetrahydropyridin-4-yl]-7H-pyrrolo[2,3-d]pyrimidine;
N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide;
4-(5-fluoro-2-methoxyphenyl)-6-[1-(pyridin-2-ylmethyl)-1,2,3,6-tetrahydropyridin-4-yl]-7H-pyrrolo[2,3-d]pyrimidine;
4-(5-fluoro-2-methoxyphenyl)-6-[1-(pyridin-4-ylmethyl)-1,2,3,6-tetrahydropyridin-4-yl]-7H-pyrrolo[2,3-d]pyrimidine;
4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine;
N-benzyl-4-fluoro-3-{6-[1-(methylsulfonyl)-1,2,3,6-tetrahydropyridin-4-yl]-7H-pyrrolo[2,3-d]pyrimidin-4-yl}aniline;
4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;
3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;
4-fluoro-3-{6-[1-(methylsulfonyl)-1,2,3,6-tetrahydropyridin-4-yl]-7H-pyrrolo[2,3-d]pyrimidin-4-yl}-N-(tetrahydrofuran-2-ylmethyl)aniline;
4-fluoro-3-{6-[1-(methylsulfonyl)-1,2,3,6-tetrahydropyridin-4-yl]-7H-pyrrolo[2,3-d]pyrimidin-4-yl}-N-(pyridin-2-ylmethyl)aniline;
4-(5-fluoro-2-methoxyphenyl)-6-[1-(pyridin-3-ylmethyl)-1,2,3,6-tetrahydropyridin-4-yl]-7H-pyrrolo[2,3-d]pyrimidine;
6-[1-(3-fluorobenzyl)-1,2,3,6-tetrahydropyridin-4-yl]-4-(5-fluoro-2-methoxyphenyl)-7H-pyrrolo[2,3-d]pyrimidine;
6-[1-(3,5-difluorobenzyl)-1,2,3,6-tetrahydropyridin-4-yl]-4-(5-fluoro-2-methoxyphenyl)-7H-pyrrolo[2,3-d]pyrimidine;
4-fluoro-3-{6-[1-(methylsulfonyl)-1,2,3,6-tetrahydropyridin-4-yl]-7H-pyrrolo[2,3-d]pyrimidin-4-yl}-N-(pyridin-4-ylmethyl)aniline;
6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine;
4-(5-fluoro-2-methoxyphenyl)-6-[1-(piperidin-4-ylmethyl)-1,2,3,6-tetrahydropyridin-4-yl]-7H-pyrrolo[2,3-d]pyrimidine;
4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine;
4-(5-chloro-2-fluoro-3-methylphenyl)-6-[1-(methylsulfonyl)-1,2,3,6-tetrahydropyridin-4-yl]-7H-pyrrolo[2,3-d]pyrimidine;
4-(2-butoxy-5-fluorophenyl)-6-[1-(methylsulfonyl)-1,2,3,6-tetrahydropyridin-4-yl]-7H-pyrrolo[2,3-d]pyrimidine;
4-[5-methyl-2-(propan-2-yloxy)phenyl]-6-[1-(methylsulfonyl)-1,2,3,6-tetrahydropyridin-4-yl]-7H-pyrrolo[2,3-d]pyrimidine;
4-(2-methoxy-5-methylphenyl)-6-[1-(methylsulfonyl)-1,2,3,6-tetrahydropyridin-4-yl]-7H-pyrrolo[2,3-d]pyrimidine;
4-(5-chloro-2-methoxyphenyl)-6-[1-(methylsulfonyl)-1,2,3,6-tetrahydropyridin-4-yl]-7H-pyrrolo[2,3-d]pyrimidine;
4-(2,4-difluorophenyl)-6-[1-(methylsulfonyl)-1,2,3,6-tetrahydropyridin-4-yl]-7H-pyrrolo[2,3-d]pyrimidine;
6-[1-(methylsulfonyl)-1,2,3,6-tetrahydropyridin-4-yl]-4-[2-(trifluoromethyl)phenyl]-7H-pyrrolo[2,3-d]pyrimidine;
N-(3-{6-[1-(methylsulfonyl)-1,2,3,6-tetrahydropyridin-4-yl]-7H-pyrrolo[2,3-d]pyrimidin-4-yl}phenyl)methanesulfonamide;
4-(5-fluoro-2-propoxyphenyl)-6-[1-(methylsulfonyl)-1,2,3,6-tetrahydropyridin-4-yl]-7H-pyrrolo[2,3-d]pyrimidine;
4-(2-fluoro-5-methylphenyl)-6-[1-(methylsulfonyl)-1,2,3,6-tetrahydropyridin-4-yl]-7H-pyrrolo[2,3-d]pyrimidine;
4-[2-fluoro-5-(trifluoromethyl)phenyl]-6-[1-(methylsulfonyl)-1,2,3,6-tetrahydropyridin-4-yl]-7H-pyrrolo[2,3-d]pyrimidine;
4-[2-fluoro-5-(propan-2-yloxy)phenyl]-6-[1-(methylsulfonyl)-1,2,3,6-tetrahydropyridin-4-yl]-7H-pyrrolo[2,3-d]pyrimidine;
4-(5-methyl-2-propoxyphenyl)-6-[1-(methylsulfonyl)-1,2,3,6-tetrahydropyridin-4-yl]-7H-pyrrolo[2,3-d]pyrimidine;
4-(5-butoxy-2-fluorophenyl)-6-[1-(methylsulfonyl)-1,2,3,6-tetrahydropyridin-4-yl]-7H-pyrrolo[2,3-d]pyrimidine;
4-(2-fluoro-3-methoxyphenyl)-6-[1-(methylsulfonyl)-1,2,3,6-tetrahydropyridin-4-yl]-7H-pyrrolo[2,3-d]pyrimidine;
6-[1-(methylsulfonyl)-1,2,3,6-tetrahydropyridin-4-yl]-4-[3-(trifluoromethoxy)phenyl]-7H-pyrrolo[2,3-d]pyrimidine;
6-[1-(methylsulfonyl)-1,2,3,6-tetrahydropyridin-4-yl]-4-[2-(trifluoromethoxy)phenyl]-7H-pyrrolo[2,3-d]pyrimidine;

6-(4,4-difluorocyclohex-1-en-1-yl)-4-(5-fluoro-2-methoxyphenyl)-7H-pyrrolo[2,3-d]pyrimidine;
6-(3,6-dihydro-2H-pyran-4-yl)-4-(5-fluoro-2-methoxyphenyl)-7H-pyrrolo[2,3-d]pyrimidine;
tert-butyl 4-[4-(2-ethoxy-5-fluorophenyl)-7H-pyrrolo[2,3-d]pyrimidin-6-yl]-3,6-dihydropyridine-1(2H)-carboxylate;
4-(2-ethoxy-5-fluorophenyl)-6-(1,2,3,6-tetrahydropyridin-4-yl)-7H-pyrrolo[2,3-d]pyrimidine;
N-[4-({4-[4-(2-ethoxy-5-fluorophenyl)-7H-pyrrolo[2,3-d]pyrimidin-6-yl]-3,6-dihydropyridin-1(2H)-yl}methyl)phenyl]acetamide;
tert-butyl [4-({4-[4-(5-fluoro-2-methoxyphenyl)-7H-pyrrolo[2,3-d]pyrimidin-6-yl]-3,6-dihydropyridin-1(2H)-yl}methyl)phenyl]carbamate;
4-({4-[4-(5-fluoro-2-methoxyphenyl)-7H-pyrrolo[2,3-d]pyrimidin-6-yl]-3,6-dihydropyridin-1(2H)-yl}methyl)aniline;
methyl 4-({4-[4-(5-fluoro-2-methoxyphenyl)-7H-pyrrolo[2,3-d]pyrimidin-6-yl]-3,6-dihydropyridin-1(2H)-yl}methyl)benzoate;
4-({4-[4-(5-fluoro-2-methoxyphenyl)-7H-pyrrolo[2,3-d]pyrimidin-6-yl]-3,6-dihydropyridin-1(2H)-yl}methyl)benzoic acid;
methyl trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylate;
trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylic acid;
4-[4-(5-fluoro-2-methoxyphenyl)-7H-pyrrolo[2,3-d]pyrimidin-6-yl]-N,N-dimethyl-3,6-dihydropyridine-1(2H)-carboxamide;
4-[4-(2,3-difluorophenyl)-7H-pyrrolo[2,3-d]pyrimidin-6-yl]-N,N-dimethyl-3,6-dihydropyridine-1(2H)-carboxamide;
(2S)-cyclohexyl({4-[4-(5-fluoro-2-methoxyphenyl)-7H-pyrrolo[2,3-d]pyrimidin-6-yl]cyclohex-3-en-1-yl}amino)acetic acid;
N-{4-[4-(5-fluoro-2-methoxyphenyl)-7H-pyrrolo[2,3-d]pyrimidin-6-yl]cyclohex-3-en-1-yl}-L-valine;
4-[4-(5-fluoro-2-methoxyphenyl)-7H-pyrrolo[2,3-d]pyrimidin-6-yl]cyclohex-3-ene-1-carboxylic acid;
2-{4-[4-(5-fluoro-2-methoxyphenyl)-7H-pyrrolo[2,3-d]pyrimidin-6-yl]-3,6-dihydropyridin-1(2H)-yl}-N,N-dimethylacetamide;
N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]methanesulfonamide;
ethyl ({4-[4-(5-fluoro-2-methoxyphenyl)-7H-pyrrolo[2,3-d]pyrimidin-6-yl]-3,6-dihydropyridin-1(2H)-yl}sulfonyl)carbamate;
N-{4-[4-(5-fluoro-2-methoxyphenyl)-7H-pyrrolo[2,3-d]pyrimidin-6-yl]cyclohex-3-en-1-yl}-3-methyl-L-valine;
N-{4-[4-(5-fluoro-2-methoxyphenyl)-7H-pyrrolo[2,3-d]pyrimidin-6-yl]cyclohex-3-en-1-yl}-D-valine;
N-{4-[4-(5-fluoro-2-methoxyphenyl)-7H-pyrrolo[2,3-d]pyrimidin-6-yl]cyclohex-3-en-1-yl}-L-leucine;
4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid;
(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid; and pharmaceutically acceptable salts thereof.

Schemes

Compounds of the present invention (e.g., compounds of Formula I) can be prepared by applying synthetic methodology known in the art and synthetic methodology outlined in the schemes set forth below.

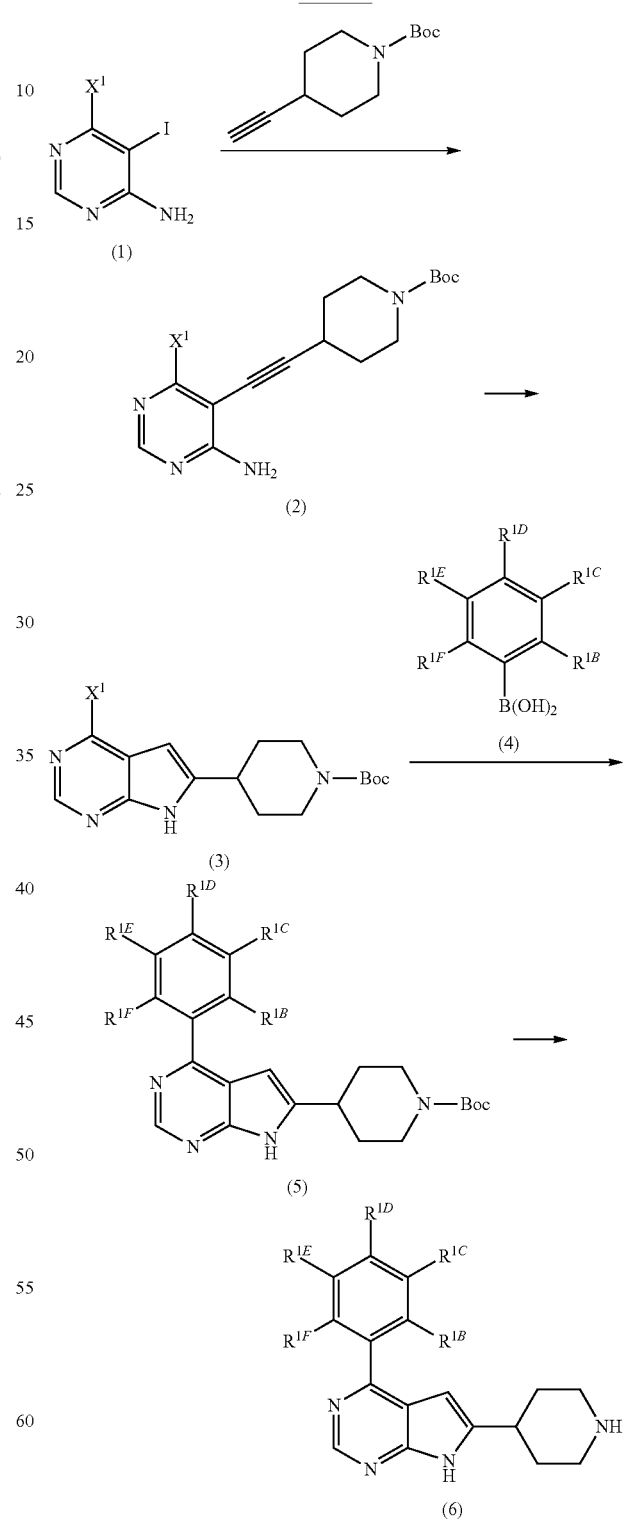

As shown in Scheme 1, compounds of formula (1) wherein $X^1$ is an appropriate halide or triflate, can be reacted with tert-butyl 4-ethynylpiperidine-1-carboxylate in the presence of copper (I) iodide, a base such as but not limited to triethylamine, and a catalyst such as but not limited to bis(triphenylphosphine) palladium(II)chloride, to provide compounds of formula (2). The reaction is typically performed at ambient temperature in a solvent such as but not limited to N,N-dimethylformamide. Compounds of formula (3) can be prepared by reacting compounds of formula (2) with a base such as but not limited to potassium tert-butoxide in the presence of 18-crown-6. The reaction is typically performed in a solvent such as but not limited to toluene under a nitrogen atmosphere at an elevated temperature (e.g., 65° C.). Compounds of formula (3) can be reacted with compounds of formula (4), wherein $R^{1B}$, $R^{1C}$, $R^{1D}$, $R^{1E}$, and $R^{1F}$ are as described herein, under Suzuki coupling reaction conditions (N. Miyama and A. Suzuki, Chem. Rev. 1995, 95:2457-2483, J. Organomet. Chem. 1999, 576:147-148) to provide compounds of formula (5). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but are not limited to, carbonates or phosphates of sodium, potassium, and cesium, acetates of sodium or potassium, and cesium fluoride. Examples of suitable ligands include, but are not limited to, 2-(dicyclohexylphosphino)biphenyl, 1,3,5,7-tetramethyl-6-phenyl-2,4,8-trioxa-6-phosphaadamante, 2-dicyclohexylphosphino-2',4',6'-triisopropylbiphenyl(X-phos), and 1,1'-bis(diphenylphosphanyl)ferrocene. Non-limiting examples of suitable solvent include methanol, ethanol, dimethoxyethane, N,N-dimethylformamide, dimethylsulfoxide, dioxane, tetrahydropyran, and water, or mixtures thereof. Compounds of formula (6), which are representative of compounds of Formula (IIIa), can be prepared by deprotecting compounds of formula (5) under conditions described herein (e.g. with an acid such as hydrochloric acid in a solvent such as dioxane, ethanol or ethyl acetate or trifluoroacetic acid in a solvent such as dichloromethane).

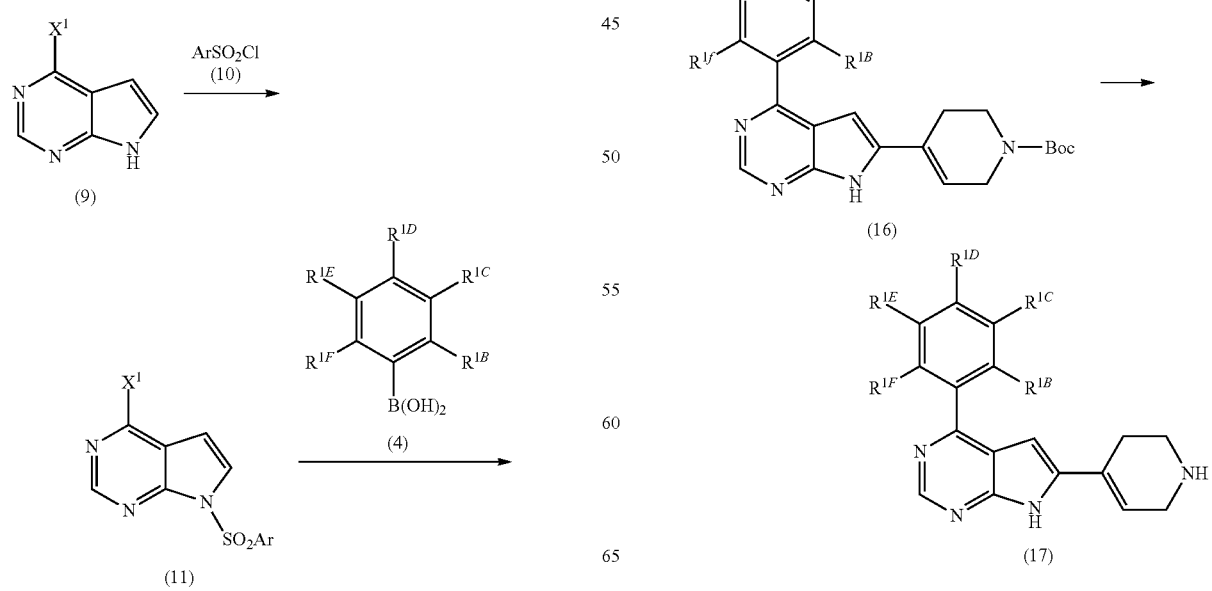

Compounds of formula (9), wherein $X^1$ is a suitable halide or triflate, can be treated with a strong base such as but not limited to sodium hydride followed by reaction with compounds of formula (10), wherein Ar is a suitable aryl group, to provide compounds of formula (11). The reaction is typically performed in a solvent such as but not limited to N,N-dimethylformamide at low temperature (e.g., 0° C.). Compounds of formula (13) can be prepared by reacting compounds of formula (11) with compounds of formula (4), under Suzuki Coupling reaction conditions as described above in Scheme 1. Compounds of formula (14) can be prepared by reacting compounds of formula (13) with a strong base such as but not limited to lithium diisopropylamide, followed by reaction with iodide. The reaction is typically performed in a solvent such as but not limited to tetrahydrofuran at low temperature (e.g., −78° C.). tert-Butyl 4-(4,4,5,5-tetramethyl-1,3,2-dioxaborolan-2-yl)-5,6-dihydropyridine-1(2H)-carboxylate can be reacted with compounds of formula (14) under Suzuki Coupling reaction conditions as described above in Scheme 1, to provide compounds of formula (15). Compounds of formula (16) can be prepared by reacting compounds of formula (15) with a base, such as but not limited to, sodium hydroxide. The reaction is typically performed in a solvent such as, but not limited to dioxane at an elevated temperature (e.g., 100° C.). Compounds of formula (17), which are representative of compounds of Formula (IIIa), can be prepared by deprotecting compounds of formula (16) under conditions described herein (e.g. with an acid such as hydrochloric acid in a solvent such as dioxane, ethanol or ethyl acetate or trifluoroacetic acid in a solvent such as dichloromethane).

Compounds of formula (21), which are representative of compounds of Formula (IIIa), wherein $R^4$ is as described herein for substituents on the $R^{2A}$ $C_1$-alkyl, and ⇝ indicates a single or double bond, can be prepared by reacting compounds of formula (18), wherein $R^{1B}$, $R^{1C}$, $R^{1D}$, $R^{1E}$, and $R^{1F}$ are as described herein, with compounds of formula (19) or (20) under appropriate alkylation or reductive amination conditions. Compounds of formula (23), which are representative of compounds of Formula (IIIa) and wherein $R^5$ is as described herein for Formula (IIIa), can be prepared by reacting compounds of formula (18) with compounds of formula (22) under appropriate urea formation conditions. Compounds of formula (25), which are representative of compounds of Formula (IIIa) and wherein $R^7$ is as described herein for Formula (IIIa), can be prepared by reacting compounds of formula (18) with compounds of formula (24) under appropriate sulfonamidation conditions. Compounds of formula (28), which are representative of compounds of Formula (IIIa) and wherein $R^8$ is as described herein for Formula (IIIa), can be prepared by reacting compounds of formula (18) with compounds of formula (26) or formula (27) under appropriate acylation conditions. Compounds of formula (30), which are representative of compounds of Formula (IIIa) can be prepared by reacting compounds of formula (18) with compounds of formula (29) under appropriate reductive amination conditions.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a phar- Scheme 3

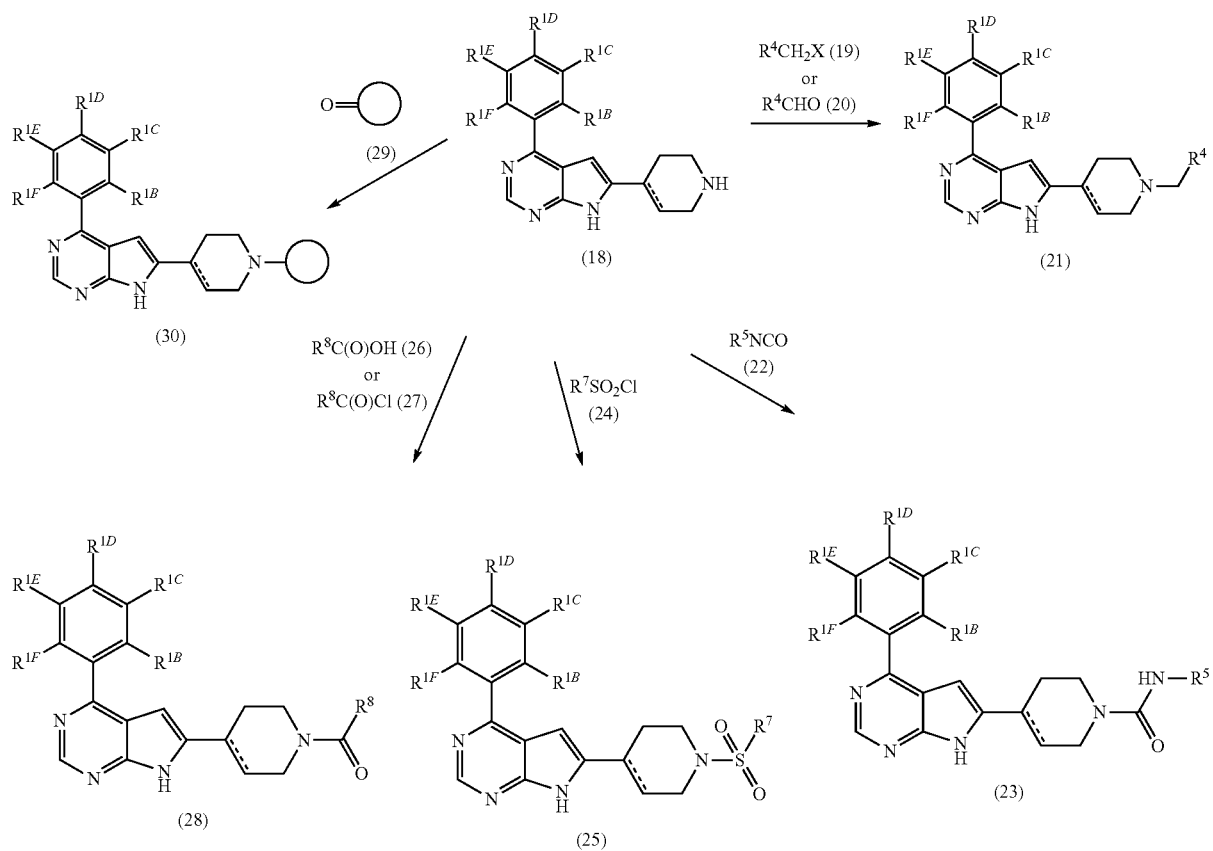

maceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a CDK9-mediated disorder or condition. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of formula I can be administered by injection, that is, intravenously, intramuscularly, intracutaneously, subcutaneously, intraduodenally, parentally, or intraperitoneally. In certain embodiments, a compound of formula I may be administered orally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. CDK9-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti- HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The following Examples may be used for illustrative purposes and should not be deemed to narrow the scope of the invention.

EXAMPLES

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

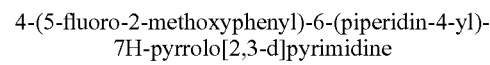
4-(5-fluoro-2-methoxyphenyl)-6-(piperidin-4-yl)-7H-pyrrolo[2,3-d]pyrimidine Example 1A

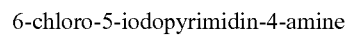
6-chloro-5-iodopyrimidin-4-amine

To a solution of 6-chloropyrimidin-4-amine (1 g, 7.8 mmol) in 5 mL N,N-dimethylformamide was added N-iodosuccinimide (2.6 g, 11.6 mmol) and the mixture subjected to microwave irradiation (Biotage Initiator) at 100° C. for 30 minutes. The mixture was diluted with water and ethyl acetate and the ethyl acetate layer was washed with water and brine, dried over sodium sulfate, filtered, and concentrated. Purification by column chromatography (silica gel, 25% ethyl acetate in hexane) afforded the title compound. LCMS: 255.91 (M+1)⁺.

Example 1B tert-butyl 4-((4-amino-6-chloropyrimidin-5-yl)ethynyl)piperidine-1-carboxylate To a degassed solution of Example 1A (400 mg, 1.6 mmol) in N,N-dimethylformamide (6 mL) was added copper (I) iodide (120 mg, 0.63 mmol) and triethylamine (2 mL, 14.33 mmol). The mixture was degassed for 5 minutes and tert-butyl 4-ethynylpiperidine-1-carboxylate (1.67 g, 7.98 mmol) and bis(triphenylphosphine) palladium(II)chloride (220 mg, 0.31 mmol) were added. The mixture was stirred at room temperature for 3 hours and diluted with water and extracted with ethyl acetate. The ethyl acetate layers were washed with water and brine, dried over sodium sulfate, filtered, and concentrated. Purification by column chromatography (silica gel, 30% ethyl acetate in hexane) afforded the title compound. LCMS: 337.1 (M+1)+.

Example 1C tert-butyl 4-(4-chloro-7H-pyrrolo[2,3-d]pyrimidin-6-yl)piperidine-1-carboxylate To a solution of Example 1B (250 mg, 0.74 mmol), in toluene (5 mL), was added potassium tert-butoxide (249 mg, 2.22 mmol) followed by 18-crown-6 (15 mg, 0.057 mmol) and the mixture was heated under nitrogen at 65° C. for 12 hours. The mixture was cooled to room temperature, diluted with ethyl acetate, washed with water and brine, dried over sodium sulfate, filtered, concentrated and purified by column chromatography (silica gel, 40% ethyl acetate in hexane) to afford the title compound. LCMS: 337.1 (M+1)+.

Example 1D tert-butyl 4-(4-(5-fluoro-2-methoxyphenyl)-7H-pyrrolo[2,3-d]pyrimidin-6-yl)piperidine-1-carboxylate To a solution of Example 1C (200 mg, 0.6 mmol) in N,N-dimethylformamide (8 mL), was added a solution of sodium bicarbonate (0.118 g, 1.404 mmol) in 0.5 mL water followed by 5-fluoro-2-methoxyphenylboronic acid (204 mg, 1.2 mmol). The mixture was degassed with nitrogen and [1,1'-bis (di tert butyl phosphino)ferrocene]palladium(II) dichloride (21 mg, 0.033 mmol) was added. The mixture was heated under microwave conditions (Biotage Initiator) at 100° C. for 1 hour. The mixture was diluted with ethyl acetate and filtered through diatomaceous earth. The organic layer was washed with water and brine, dried over sodium sulfate, filtered, concentrated and purified by column chromatography (silica gel, 40% ethyl acetate-hexane) to afford the title compound. LCMS: 427.21 (M+1)+.

Example 1E 4-(5-fluoro-2-methoxyphenyl)-6-(piperidin-4-yl)-7H-pyrrolo[2,3-d]pyrimidine To a solution of Example 1D (100 mg, 0.23 mmol) in dichloromethane (2 mL), was added hydrogen chloride-saturated ethyl acetate (2 mL) and the mixture was stirred at room temperature for 2 hours. The mixture was concentrated and purified by preparative HPLC (Agilent AD/SP/C18-25/011 reversed phase column) eluting with a gradient of 0.01% trifluoroacetic acid in water to 1:1 methanol/acetonitrile to afford the title compound as the hydrochloride salt. LCMS: 327.1 (M+H)+; 1H NMR (400 MHz, DMSO-d6/D2O): δ 1.77-1.87 (m, 2H), 2.23 (d, J=12 Hz, 2H), 3.0-3.06 (m, 2H), 3.33-3.41 (m, 3H), 3.79 (s, 3H), 6.45 (s, 1H), 7.29-7.32 (m, 1H), 7.44-7.50 (m, 2H), 8.99 (s, 1H).

Example 2

4-(5-fluoro-2-methoxyphenyl)-6-(1-methylpiperidin-4-yl)-7H-pyrrolo[2,3-d]pyrimidine A solution of Example 1D (50 mg, 0.117 mmol) in 2 mL tetrahydrofuran was cooled to 0° C. and 1M lithium aluminum hydride in tetrahydrofuran (0.469 mL) was added under nitrogen. The mixture was warmed to room temperature and heated at 60° C. for 2 hours. The mixture was cooled to 0° C. and 5 mL ethyl acetate and 2 mL saturated ammonium chloride were added. After stirring for 30 minutes, the mixture was extracted with ethyl acetate, and the organic layers were washed with water and brine, dried over sodium sulfate, filtered, concentrated and purified by preparative HPLC (Zorbax XDB C-18 (32) reversed phase column) eluting with a gradient of 0.01% trifluoroacetic acid in water to 1:1 methanol/acetonitrile to afford the title compound as the trifluoroacetate salt. LCMS: 341.1 (M+H)+. 1H NMR (400 MHz, CDCl3): δ 1.30-1.35 (m, 2H), 2.02-2.04 (m, 2H), 2.43-25.0 (m, 2H), 2.96 (s, 3H), 3.241-3.254 (m, 2H), 3.68-3.69 (m, 1H), 3.93 (s, 3H), 6.62 (s, 1H), 6.73 (s, 1H), 7.36-7.39 (m, 1H), 7.47-7.53 (m, 1H), 7.54-7.57 (m, 1H), 9.03 (s, 1H).

Example 3

4-(5-fluoro-2-methoxyphenyl)-6-(1,2,3,6-tetrahydropyridin-4-yl)-7H-pyrrolo[2,3-d]pyrimidine

Example 3A 4-bromo-7-(phenylsulfonyl)-7H-pyrrolo[2,3-d]pyrimidine

To a solution of 4-bromo-7H-pyrrolo[2,3-d]pyrimidine (2.5 g, 12.62 mmol) in 50 mL N,N-dimethylformamide at 0° C. was added 95% sodium hydride (0.351 g, 13.89 mmol). The mixture was stirred at 0° C. for 30 minutes, benzenesulfonyl chloride (1.772 mL, 13.89 mmol) was added, and the mixture was stirred at 0° C. for an additional 2 hours. The mixture was quenched with 20 mL saturated ammonium chloride and diluted with water (100 mL). The resulting suspension was stirred for 5 minutes, filtered, and dried under-vacuum to give the title compound. MS (ESI+) m/z 340.0 (M+H)+.

Example 3B 4-(5-fluoro-2-methoxyphenyl)-7-(phenylsulfonyl)-7H-pyrrolo[2,3-d]pyrimidine To a suspension of Example 3A (5 g, 14.79 mmol) in 2:1 1,2-dimethyoxyethane/ethanol (150 mL) was added 2M aqueous sodium carbonate (29.6 mL, 59.1 mmol), (5-fluoro-2-methoxyphenyl)boronic acid (3.02 g, 17.74 mmol) and dichlorobis(triphenylphosphine) palladium(II) (1.038 g, 1.479 mmol). The mixture was heated at 100° C. for 1.5 hours, cooled and diluted with 100 mL ethyl acetate. The organic layer was washed with saturated sodium bicarbonate solution, water, and brine, dried over magnesium sulfate, filtered, and concentrated. The residue was triturated with dichloromethane, filtered, and dried under vacuum. The filtrate was concentrated to ⅓ volume, and the solid filtered and rinsed with dichloromethane. The remainder of the filtrate was purified by flash chromatography on silica (Analogix 280) eluting with a gradient of 15 to 70% ethyl acetate/hexane. This was combined with the triturated material and dried over vacuum to give the title compound. MS (ESI$^+$) m/z 383.5 (M+H)$^+$.

Example 3C 4-(5-fluoro-2-methoxyphenyl)-6-iodo-7-(phenylsulfonyl)-7H-pyrrolo[2,3-d]pyrimidine To a solution of Example 3B (2.5 g, 6.52 mmol) in 50 mL tetrahydrofuran at −78° C. was added 2M lithium diisopropylamide (4.89 mL, 9.78 mmol) over 5 minutes. The solution was stirred at −78° C. for 30 minutes and a solution of iodine (3.31 g, 13.04 mmol) in tetrahydrofuran (50 mL) was added over 5 minutes. The mixture was stirred at −78° C. for 2 hours and quenched with 50 mL 1M sodium thiosulfate. The aqueous layer was extracted with ethyl acetate (3×50 mL) and the combined organic layers were washed with brine, dried over magnesium sulfate, filtered and concentrated to give the title compound, which was used without further purification. MS (ESI$^+$) m/z 509.51 (M+H)$^+$.

Example 3D tert-butyl 4-(4-(5-fluoro-2-methoxyphenyl)-7-(phenylsulfonyl)-7H-pyrrolo[2,3-d]pyrimidin-6-yl)-5,6-dihydropyridine-1(2H)-carboxylate To a solution of Example 3C (3.07 g, 6.03 mmol) in 70 mL 1,2-dimethyoxyethane/ethanol (50:20) was added tert-butyl 4-(4,4,5,5-tetramethyl-1,3,2-dioxaborolan-2-yl)-5,6-dihydropyridine-1(2H)-carboxylate (2.80 g, 9.04 mmol), 2M sodium carbonate (12.06 mL, 24.11 mmol) and bis(triphenylphosphine)palladium(II) dichloride (0.423 g, 0.603 mmol). The mixture was stirred at 100° C. for 3 hours, cooled and diluted with 50 mL ethyl acetate. The organic layer was washed with saturated sodium bicarbonate, water and brine, dried over magnesium sulfate, filtered, and concentrated. Purification by flash chromatography on silica (Analogix 280) eluting with a gradient of 20% to 80% ethyl acetate/hexane gave the title compound. MS (ESI$^+$) m/z 565.43 (M+H)$^+$.

Example 3E tert-butyl 4-(4-(5-fluoro-2-methoxyphenyl)-7H-pyrrolo[2,3-d]pyrimidin-6-yl)-5,6-dihydropyridine-1(2H)-carboxylate To a solution of Example 3D (2.6 g, 4.60 mmol) in dioxane was added 6M sodium hydroxide (7.67 mL, 46 mmol). The mixture was stirred at 100° C. for 2 hours, cooled and diluted with 50 mL ethyl acetate. The organic layer was washed with saturated sodium bicarbonate solution, water and brine, dried over magnesium sulfate, filtered, and concentrated to give the title compound, which was used without further purification. MS (ESI$^+$) m/z 425.43 (M+H)$^+$.

Example 3F 4-(5-fluoro-2-methoxyphenyl)-6-(1,2,3,6-tetrahydropyridin-4-yl)-7H-pyrrolo[2,3-d]pyrimidine To a solution of Example 3E (900 mg, 2.120 mmol) in 10 mL dicholoromethane was added trifluoroacetic acid (1.634 mL, 21.2 mmol). The mixture was stirred at room temperature for 2 hours and the solvent was removed by azeotroping with ethyl acetate. The residue was dissolved in 3 mL methanol and treated with 2M hydrogen chloride in ether (1 mL) for 1 hour. The mixture was diluted with ether and the solid filtered to give the title compound as a hydrochloride salt. $^1$H NMR (300 MHz, DMSO-d$_6$) δ 2.64-2.81 (m, 2H) 3.76-3.82 (m, 3H) 3.81-3.90 (m, 2H) 6.52 (s, 1H) 6.56 (s, 1H) 7.17-7.33 (m, 1H) 7.32-7.49 (m, 2H) 8.86 (s, 1H) 8.95 (s, 2H) 12.57 (s, 1H). MS (ESI$^+$) m/z 325.1 (M+H)$^+$.

Example 4

4-(5-fluoro-2-methoxyphenyl)-6-(1-methyl-1,2,3,6-tetrahydropyridin-4-yl)-7H-pyrrolo[2,3-d]pyrimidine

Example 4A 4-(5-fluoro-2-methoxyphenyl)-6-(1-methyl-1,2,3,6-tetrahydropyridin-4-yl)-7-(phenylsulfonyl)-7H-pyrrolo[2,3-d]pyrimidine The title compound was prepared as described in Example 3D, using 1-methyl-4-(4,4,5,5-tetramethyl-1,3,2-dioxaborolan-2-yl)-1,2,3,6-tetrahydropyridine in place of tert-butyl 444,4,5,5-tetramethyl-1,3,2-dioxaborolan-2-yl)-5,6-dihydropyridine-1(2H)-carboxylate. MS (ESI$^+$) m/z 478.89 (M+H)$^+$.

Example 4B 4-(5-fluoro-2-methoxyphenyl)-6-(1-methyl-1,2,3,6-tetrahydropyridin-4-yl)-7H-pyrrolo[2,3-d]pyrimidine The title compound was prepared as described in Example 3E, using Example 4A in place of Example 3D. The crude material was triturated with ethyl acetate to give the title compound. $^1$H NMR (300 MHz, DMSO-d$_6$) δ 2.28 (s, 3H) 2.55 (t, J=5.09 Hz, 2H) 3.06 (d, J=3.05 Hz, 2H) 3.72-3.81 (m, 3H) 6.27 (d, J=1.70 Hz, 1H) 6.48-6.59 (m, 1H) 7.17-7.27 (m, 1H) 8.76 (s, 1H) 12.19 (s, 1H). MS (ESI$^+$) m/z 339.0 (M+H)$^+$.

Example 5

4-(5-fluoro-2-methoxyphenyl)-6-[1-(methylsulfonyl)-1,2,3,6-tetrahydropyridin-4-yl]-7H-pyrrolo[2,3-d]pyrimidine To a solution of Example 3F (100 mg, 0.277 mmol) in 3 mL N,N-dimethylformamide was added N-ethyl-N-isopropylpropan-2-amine (0.169 mL, 0.97 mmol) followed by methanesulfonyl chloride (0.028 mL, 0.36 mmol). The mixture was stirred at room temperature for 1 hour and was diluted with 30 mL ethyl acetate. The organic layer was washed with saturated sodium bicarbonate solution, water and brine, dried over magnesium sulfate, filtered, and concentrated. The residue was triturated with ethyl acetate to give the title compound. $^1$H NMR (300 MHz, DMSO-d$_6$) δ 2.63 (s, 2H) 2.94 (s, 3H) 3.38 (t, J=5.76 Hz, 2H) 3.78 (s, 3H) 3.93 (d, J=3.05 Hz, 2H) 6.36 (s, 1H) 6.59 (s, 1H) 7.17-7.28 (m, 1H) 7.29-7.41 (m, 2H) 8.78 (s, 1H) 12.29 (s, 1H). MS (ESI$^+$) m/z 403.0 (M+H)$^+$

Example 6

1-{4-[4-(5-fluoro-2-methoxyphenyl)-7H-pyrrolo[2,3-d]pyrimidin-6-yl]-3,6-dihydropyridin-1(2H)-yl}ethanone The title compound was prepared as described in Example 5, using acetic anhydride in place of methanesulfonyl chloride. The crude material was purified by flash chromatography on silica (Analogix 280) eluting with a gradient of 0% to 5% methanol in dichloromethane to give the title compound. $^1$H NMR (500 MHz, DMSO-$d_6$) δ 2.06 (d, J=13.73 Hz, 3H) 2.46 (s, 1H) 2.57 (s, 1H) 3.55-3.69 (m, 2H) 3.78 (d, J=1.83 Hz, 3H) 4.18 (dd, J=30.52, 2.14 Hz, 2H) 6.34 (d, J=7.02 Hz, 1H) 6.57 (s, 1H) 7.17-7.28 (m, 1H) 7.35 (t, J=7.48 Hz, 2H) 8.78 (s, 1H) 12.29 (d, J=14.65 Hz, 1H). MS (ESI$^+$) m/z 367.1 (M+H)$^+$.

Example 7

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone To a solution of Example 3F (150 mg, 0.416 mmol) in N,N-dimethylformamide was added N-ethyl-N-isopropylpropan-2-amine (0.254 mL, 1.455 mmol), 1H-benzo[d][1,2,3]triazol-1-ol hydrate (95 mg, 0.624 mmol), N$^1$-((ethylimino)methylene)-N$^3$,N$^3$-dimethylpropane-1,3-diamine hydrochloride (120 mg, 0.624 mmol) and 2-hydroxyacetic acid (0.054 mL, 0.624 mmol). The mixture was stirred at room temperature for 1 hour and diluted with 40 mL ethyl acetate. The organic layer was washed with saturated sodium bicarbonate solution, water and brine, dried over magnesium sulfate, filtered, and concentrated. The residue was purified by flash chromatography on silica (Analogix 280) eluting with a gradient of 0% to 6% methanol in dichloromethane to give the title compound. $^1$H NMR (500 MHz, DMSO-$d_6$) δ 2.56 (s, 1H) 3.47-3.74 (m, 2H) 3.78 (s, 3H) 4.15 (dd, J=21.21, 5.04 Hz, 4H) 4.51-4.70 (m, 1H) 6.35 (d, J=7.93 Hz, 1H) 6.57 (d, J=15.87 Hz, 1H) 7.17-7.27 (m, 1H) 7.29-7.40 (m, 2H) 8.78 (s, 1H) 12.30 (d, J=10.68 Hz, 1H). MS (ESI$^+$) m/z 383.1 (M+H)$^+$.

Example 8

6-[1-(cyclopropylsulfonyl)-1,2,3,6-tetrahydropyridin-4-yl]-4-(5-fluoro-2-methoxyphenyl)-7H-pyrrolo[2,3-d]pyrimidine The title compound was prepared as described in Example 5, using cyclopropanesulfonyl chloride in place of methanesulfonyl chloride. The crude material was purified by flash chromatography on silica (Analogix 280) eluting with a gradient of 1% to 6% methanol/dichloromethane to give the title compound. $^1$H NMR (300 MHz, DMSO-$d_6$) δ 0.91-1.05 (m, 4H) 2.55-2.73 (m, 3H) 3.37-3.52 (m, 2H) 3.69-3.84 (m, 3H) 3.93-4.13 (m, 2H) 7.19-7.28 (m, 1H) 7.29-7.40 (m, 2H) 8.78 (s, 1H) 12.30 (s, 1H). MS (ESI$^+$) m/z 429.0 (M+H)$^+$.

Example 9

N-benzyl-4-fluoro-3-[6-(piperidin-4-yl)-7H-pyrrolo[2,3-d]pyrimidin-4-yl]aniline

Example 9A

N-benzyl-3-bromo-4-fluoroaniline

To a solution of 2-bromo-4-fluoroaniline (2 g, 10.4 mmol) in 1,2-dichloroethane (5 mL) and acetic acid (5 mL) was added benzaldehyde (1.33 mg, 12.5 mmol) and the mixture was stirred at room temperature for 4 hours. Sodium triacetoxyborohydride (8.92 g, 42.1 mmol) was added at 5° C. and the mixture was stirred at room temperature for 12 hours. The mixture was diluted with water and treated with saturated aqueous sodium bicarbonate. The aqueous layer was extracted with ethyl acetate. The organic layer was washed with water and brine, dried over sodium sulfate, filtered, concentrated and purified by column chromatography (silica gel, 15% ethyl acetate in hexane) to afford the title compound. LCMS: 281 (M+3)$^+$.

Example 9B

N-benzyl-4-fluoro-3-(4,4,5,5-tetramethyl-1,3,2-dioxaborolan-2-yl)aniline

To a solution of Example 9A (500 mg, 1.785 mmol) in 5 mL 1,4-dioxane, was added potassium acetate (526 mg, 5.35 mmol) and 4,4,4',4',5,5,5',5'-octamethyl-2,2'-bi(1,3,2-dioxaborolane) (544 mg, 2.142 mmol). The mixture was degassed for 5 minutes and [1,1'-bis(diphenylphosphino)ferrocene]dichloropalladium(II)-dichloromethane adduct (72.9 mg, 0.089 mmol) was added and the mixture was heated at 75° C. for 12 hours. The mixture was diluted with ethyl acetate and filtered through diatomaceous earth. The organic layer was washed with brine, dried over sodium sulfate, filtered, and concentrated to afford the title compound. LCMS: 328.1 (M+H)$^+$.

Example 9C tert-butyl 4-(4-(5-(benzylamino)-2-fluorophenyl)-7H-pyrrolo[2,3-d]pyrimidin-6-yl)piperidine-1-carboxylate To a solution of Example 1C (150 mg, 0.343 mmol) in N,N-dimethylformamide (3 mL) was added sodium bicarbonate (0.087 g, 1.03 mmol) in 0.5 mL water followed by Example 9B (168 mg, 0.515 mmol). The mixture was degassed with nitrogen and [1,1'-bis(di tert butyl phosphino)ferrocene]palladium(II) dichloride (21 mg, 0.033 mmol) was added and the mixture was heated in a microwave (Biotage Initiator) at 100° C. for 1 hour. The mixture was diluted with ethyl acetate and filtered through diatomaceous earth. The organic layer was washed with water and brine, dried over sodium sulfate, filtered, concentrated and purified by column chromatography (silica gel, 40% ethyl acetate-hexane) to afford the title compound. LCMS: 502.2 (M+H)$^+$.

Example 9D

N-benzyl-4-fluoro-3-(6-(piperidin-4-yl)-7H-pyrrolo[2,3-d]pyrimidin-4-yl)aniline

Example 9C (130 mg, 0.259 mmol) was stirred in 4 mL of hydrogen chloride-saturated ethyl acetate at room temperature for 2 hours. The mixture was concentrated and purified by preparative HPLC (AG/AD/PP/C18-15/031 reversed phase column) eluting with 0.01% trifluoroacetic acid in water to afford the title compound as the trifluoroacetate salt. LCMS: 402.15 (M+H)$^+$, $^1$H NMR (400 MHz, CD$_3$OD): δ 1.93-1.97 (m, 2H), 2.32-2.36 (m, 2H), 3.33-3.34 (m, 2H), 3.54-3.58 (m, 3H), 4.41 (s, 2H), 6.42 (s, 1H), 6.93 (dd, J=3.2, 5.6 Hz, 1H), 6.98-7.01 (m, 1H), 7.18-7.23 (m, 1H), 7.28-7.29 (m, 1H), 7.33-7.42 (m, 4H), 8.95 (s, 1H).

Example 10

4-(5-fluoro-2-methoxyphenyl)-6-[1-(propan-2-ylsulfonyl)-1,2,3,6-tetrahydropyridin-4-yl]-7H-pyrrolo[2,3-d]pyrimidine The title compound was prepared as described in Example 5, using propane-2-sulfonyl chloride in place methanesulfonyl chloride. The crude material was purified by flash chromatography on silica (Analogix 280) eluting with a gradient of 1% to 6% methanol/dichloromethane to give the title compound. $^1$H NMR (400 MHz, DMSO-d$_6$) δ 1.24 (d, J=7.02 Hz, 6H) 2.47-2.54 (m, 2H) 2.56 (s, 2H) 3.36-3.45 (m, 1H) 3.50 (t, J=5.65 Hz, 2H) 3.78 (s, 3H) 4.03 (d, J=2.44 Hz, 2H) 6.28-6.43 (m, 1H) 6.50-6.68 (m, 1H) 7.18-7.27 (m, 1H) 7.30-7.39 (m, 2H). MS (ESI$^+$) m/z 431.2 (M+H)$^+$.

Example 11 cyclopropyl{4-[4-(5-fluoro-2-methoxyphenyl)-7H-pyrrolo[2,3-d]pyrimidin-6-yl]-3,6-dihydropyridin-1(2H)-yl}methanone The title compound was prepared as described in Example 5, using cyclopropanecarbonyl chloride in place of methanesulfonyl chloride. The crude material was purified by flash chromatography on silica (Analogix 280) eluting with a gradient of 1% to 6% methanol/dichloromethane to give the title compound. $^1$H NMR (400 MHz, DMSO-d$_6$) δ 0.66-0.82 (m, 4H) 1.12-1.30 (m, 1H) 1.92-2.14 (m, 1H) 2.55-2.65 (m, 1H) 3.63-3.73 (m, 1H) 3.74-3.82 (m, 3H) 3.83-3.93 (m, 1H) 4.13-4.23 (m, 1H) 4.39-4.51 (m, 1H) 6.31-6.39 (m, 1H) 6.52-6.65 (m, 1H) 7.18-7.27 (m, 1H) 7.30-7.38 (m, 2H) 8.64-8.91 (m, 1H) 12.09-12.43 (m, 1H). MS (ESI$^+$) m/z 393.2 (M+H)$^+$.

Example 12 azetidin-2-yl{4-[4-(5-fluoro-2-methoxyphenyl)-7H-pyrrolo[2,3-d]pyrimidin-6-yl]-3,6-dihydropyridin-1(2H)-yl}methanone The title compound was prepared as described in Example 7, using 1-(tert-butoxycarbonyl)azetidine-2-carboxylic acid in place of 2-hydroxyacetic acid. The crude material was purified by flash chromatography on silica (Analogix 280) eluting with a gradient of 1% to 6% methanol/dichloromethane to give the BOC-protected intermediate. The intermediate was dissolved in 3 mL dichloromethane and treated with excess trifluoroacetic acid for 1 hour. The solvent was removed and the residue was dissolved in 3 mL methanol and treated with 2M hydrogen chloride in ether for 15 minutes. The mixture was diluted with 40 mL diethyl ether and the solid was filtered to provide the title compound as the hydrochloride salt. $^1$H NMR (400 MHz, DMSO-d$_6$) δ 2.37-2.73 (m, 5H) 2.73-2.90 (m, 1H) 4.28 (s, 1H) 5.24-5.54 (m, 1H) 6.65-6.84 (m, 2H) 7.26-7.39 (m, 1H) 7.44-7.57 (m, 2H) 8.77 (s, 1H) 9.04 (s, 1H) 10.07 (s, 1H) 13.33 (s, 1H). MS (ESI$^+$) m/z 408.1 (M+H)$^+$.

Example 13

4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one The title compound was prepared as described in Example 7, using 4-oxoazetidine-2-carboxylic acid in place of 2-hydroxyacetic acid. The crude material was purified by flash chromatography on silica (Analogix 280) eluting with a gradient of 1% to 6% methanol/dichloromethane to give the title compound. $^1$H NMR (300 MHz, DMSO-d$_6$) δ 2.53-2.66 (m, 1H) 2.84 (t, J=13.73 Hz, 1H) 3.15-3.28 (m, 2H) 3.48-3.68 (m, 2H) 3.69-3.85 (m, 3H) 4.19 (s, 1H) 4.37-4.56 (m, 1H) 6.35 (d, J=5.76 Hz, 1H) 6.56 (d, J=10.85 Hz, 1H) 7.17-7.28 (m, 1H) 7.29-7.40 (m, 2H) 8.25 (s, 1H) 8.78 (s, 1H) 12.28 (s, 1H). MS (ESI$^+$) m/z 422.2 (M+H)$^+$.

Example 14

5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one The title compound was prepared as described in Example 7, using 6-oxopiperidine-3-carboxylic acid in place of 2-hydroxyacetic acid. The crude material was purified by flash chromatography on silica (Analogix 280) eluting with a gradient of 1% to 8% methanol/dichloromethane to give the title compound. $^1$H NMR (300 MHz, DMSO-d$_6$) δ 1.62-1.99 (m, 2H) 2.09-2.43 (m, 2H) 2.53-2.67 (m, 2H) 3.05-3.27 (m, 3H) 3.62-3.77 (m, 2H) 3.76-3.83 (m, 3H) 4.06-4.27 (m, 1H) 4.27-4.42 (m, 1H) 6.35 (s, 1H) 6.57 (s, 1H) 7.18-7.28 (m, 1H) 7.29-7.40 (m, 2H) 7.43 (s, 1H) 8.78 (s, 1H) 12.28 (d, J=1.36 Hz, 1H). MS (ESI$^+$) m/z 450.2 (M+H)$^+$.

Example 15

4-[4-(5-fluoro-2-methoxyphenyl)-7H-pyrrolo[2,3-d]pyrimidin-6-yl]-3,6-dihydropyridin-1(2H)-yl(tetrahydro-2H-pyran-3-yl)methanone The title compound was prepared as described in Example 7, using tetrahydro-2H-pyran-3-carboxylic acid in place of 2-hydroxyacetic acid. The crude material was purified by flash chromatography on silica (Analogix 280) eluting with a gradient of 0% to 4% methanol/dichloromethane to give the title compound. $^1$H NMR (300 MHz, DMSO-d$_6$) δ 1.59 (s, 3H) 1.74-1.93 (m, 1H) 2.36-2.67 (m, 2H) 2.90 (d, J=10.17 Hz, 1H) 3.33-3.42 (m, 2H) 3.57-3.75 (m, 2H) 3.75-3.89 (m, 6H) 6.34 (s, 1H) 6.56 (s, 1H) 7.18-7.27 (m, 1H) 7.30-7.40 (m, 2H) 8.55-8.99 (m, 1H) 12.27 (s, 1H). MS (ESI$^+$) m/z 437.2 (M+H)$^+$.

Example 16

(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone The title compound was prepared as described in Example 7, using 1-ethylpyrrolidine-3-carboxylic acid in place of 2-hydroxyacetic acid. Purification by preparative HPLC (Waters LC4000, Phenomenex Luna C8(2) 5 μm 100A AXIA column) using a gradient of 10% to 95% acetonitrile/0.1% trifluoroacetic acid in water provided the title compound. $^1$H NMR (400 MHz, DMSO-d$_6$) δ 1.09-1.33 (m, 3H) 1.74-2.19 (m, 1H) 2.18-2.50 (m, 1H) 2.63 (s, 1H) 2.88-3.44 (m, 4H) 3.47-3.91 (m, 8H) 4.07-4.44 (m, 2H) 6.55 (s, 1H) 6.66 (s, 1H) 7.22-7.35 (m, 1H) 7.44 (t, J=7.48 Hz, 2H) 8.94 (s, 1H) 9.91 (d, J=148.01 Hz, 1H) 12.81 (s, 1H). MS (ESI$^+$) m/z 450.2 (M+H)$^+$.

Example 17

4-[4-(5-fluoro-2-methoxyphenyl)-7H-pyrrolo[2,3-d]pyrimidin-6-yl]-N-methyl-3,6-dihydropyridine-1(2H)-carboxamide The title compound was prepared as described in Example 5, using 2,5-dioxopyrrolidin-1-yl methylcarbamate in place of methanesulfonyl chloride. The mixture was quenched with 10 mL water and the solid was filtered and dried under vacuum to give the title compound $^1$H NMR (300 MHz, DMSO-$d_6$) δ 2.45 (s, 2H) 2.59 (d, J=4.41 Hz, 3H) 3.51 (t, J=5.59 Hz, 2H) 3.78 (s, 3H) 4.02 (d, J=2.37 Hz, 2H) 6.34 (s, 1H) 6.41-6.51 (m, 1H) 6.56 (s, 1H) 7.18-7.27 (m, 1H) 7.29-7.39 (m, 2H) 8.77 (s, 1H) 12.23 (s, 1H). MS (ESI$^+$) m/z 382.2 (M+H)$^+$.

Example 18

1-{4-[4-(5-fluoro-2-methoxyphenyl)-7H-pyrrolo[2,3-d]pyrimidin-6-yl]-3,6-dihydropyridin-1(2H)-yl}-2-methoxyethanone The title compound was prepared as described in Example 5, using 2-methoxyacetyl chloride in place of methanesulfonyl chloride. The crude material was purified by flash chromatography on silica (Analogix 280) eluting with a gradient of 1% to 5% methanol/dichloromethane to give the title compound. $^1$H NMR (300 MHz, DMSO-$d_6$) δ 2.56 (s, 1H) 3.53-3.72 (m, 2H) 3.73-3.83 (m, 4H) 4.10-4.22 (m, 4H) 6.35 (s, 1H) 6.57 (s, 1H) 7.18-7.27 (m, 1H) 7.29-7.41 (m, 2H) 8.78 (s, 1H) 12.28 (s, 1H). MS (ESI$^+$) m/z 397.2 (M+H)$^+$.

Example 19

4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide The title compound was prepared as described in Example 5, using 3-isocyanatoprop-1-ene in place of methanesulfonyl chloride. The residue was triturated with dichloromethane to give the title compound. $^1$H NMR (300 MHz, DMSO-$d_6$) δ 2.41-2.49 (m, 2H) 3.54 (t, J=5.59 Hz, 2H) 3.69 (t, J=5.43 Hz, 2H) 3.78 (s, 3H) 3.96-4.13 (m, 2H) 4.89-5.22 (m, 2H) 5.70-5.96 (m, 1H) 6.34 (d, J=1.70 Hz, 1H) 6.57 (s, 1H) 6.71 (t, J=5.59 Hz, 1H) 7.13-7.28 (m, 1H) 7.29-7.42 (m, 2H) 8.77 (s, 1H) 12.23 (s, 1H). MS (ESI$^+$) m/z 408.2 (M+H)$^+$.

Example 20

3-{4-[4-(5-fluoro-2-methoxyphenyl)-7H-pyrrolo[2,3-d]pyrimidin-6-yl]-3,6-dihydropyridin-1(2H)-yl}propane-1,2-diol To a solution of Example 3 (100 mg, 0.252 mmol), triethylamine (0.077 mL, 0.554 mmol) and acetic acid (0.072 mL, 1.259 mmol) in 2 mL dichloromethane was added 2,3-dihydroxypropanal (45.3 mg, 0.503 mmol) and Biotage MP-cyanoborohydride resin (2.49 mmol/g, 400 mg, 1.007 mmol). The mixture was shaken on an orbital shaker overnight. The suspension was diluted with ethyl acetate, the resin was filtered off and the filtrate was concentrated. Purification by preparative HPLC (Waters LC4000, Phenomenex Luna C8(2) 5 μm 100A AXIA column) using a gradient of 10% to 95% acetonitrile/0.1% trifluoroacetic acid in water provided the title compound as the trifluoroacetic acid salt. $^1$H NMR (300 MHz, DMSO-$d_6$) δ 2.83 (s, 2H) 3.02-3.24 (m, 1H) 3.34 (dd, J=10.85, 6.10 Hz, 3H) 3.40-3.52 (m, 1H) 3.58-3.86 (m, 4H) 3.88-4.06 (m, 2H) 4.06-4.24 (m, 1H) 6.48-6.61 (m, 2H) 7.20-7.34 (m, 1H) 8.89 (s, 1H) 9.74 (s, 1H) 12.66 (s, 1H). MS (ESI$^+$) m/z 399.1 (M+H)$^+$.

Example 21

6-(1-benzyl-1,2,3,6-tetrahydropyridin-4-yl)-4-(5-fluoro-2-methoxyphenyl)-7H-pyrrolo[2,3-d]pyrimidine The title compound was prepared as described in Example 20, using benzaldehyde in place of 2,3-dihydroxypropanal. $^1$H NMR (500 MHz, DMSO-$d_6$) δ 2.86 (s, 2H) 3.27 (s, 1H) 3.64 (s, 1H) 3.79 (s, 3H) 3.91 (s, 2H) 4.45 (d, J=9.16 Hz, 2H) 6.39-6.65 (m, 2H) 7.28 (dd, J=8.85, 3.97 Hz, 1H) 7.36-7.45 (m, 2H) 7.47-7.53 (m, 3H) 7.53-7.59 (m, 2H) 8.90 (s, 1H) 10.23 (s, 1H) 12.74 (s, 1H). MS (ESI$^+$) m/z 415.2 (M+H)$^+$.

Example 22

4-({4-[4-(5-fluoro-2-methoxyphenyl)-7H-pyrrolo[2,3-d]pyrimidin-6-yl]-3,6-dihydropyridin-1(2H)-yl}methyl)benzonitrile The title compound was prepared as described in Example 20, using 4-formylbenzonitrile in place of 2,3-dihydroxypropanal. $^1$H NMR (500 MHz, DMSO-$d_6$) δ 2.84 (s, 2H) 3.20-3.46 (m, 1H) 3.55-3.73 (m, 1H) 3.74-3.83 (m, 3H) 3.85-4.00 (m, 2H) 4.53 (s, 2H) 6.44-6.66 (m, 2H) 7.27 (dd, J=8.54, 4.27 Hz, 1H) 7.35-7.46 (m, 2H) 7.72-7.80 (m, 2H) 8.00 (d, J=8.55 Hz, 2H) 8.66-9.01 (m, 1H) 10.42 (s, 1H) 12.69 (s, 1H). MS (ESI$^+$) m/z 440.2 (M+H)$^+$.

Example 23

3-({4-[4-(5-fluoro-2-methoxyphenyl)-7H-pyrrolo[2,3-d]pyrimidin-6-yl]-3,6-dihydropyridin-1(2H)-yl}methyl)benzonitrile The title compound was prepared as described in Example 20, using 3-formylbenzonitrile in place of 2,3-dihydroxypropanal. $^1$H NMR (500 MHz, DMSO-$d_6$) δ 2.85 (s, 2H) 3.29 (d, J=19.84 Hz, 1H) 3.64 (s, 1H) 3.73-3.84 (m, 3H) 3.86-4.01 (m, 2H) 4.36-4.60 (m, 2H) 6.47-6.62 (m, 2H) 7.28 (dd, J=9.00, 4.12 Hz, 1H) 7.35-7.47 (m, 2H) 7.72 (t, J=7.78 Hz, 1H) 7.90 (d, J=7.93 Hz, 1H) 7.98 (d, J=7.63 Hz, 1H) 8.04 (s, 1H) 8.69-9.05 (m, 1H) 10.34 (s, 1H) 12.73 (s, 1H). MS (ESI$^+$) m/z 440.1 (M+H)$^+$.

Example 24

4-(5-fluoro-2-methoxyphenyl)-6-[1-(tetrahydrofuran-2-ylmethyl)-1,2,3,6-tetrahydropyridin-4-yl]-7H-pyrrolo[2,3-d]pyrimidine The title compound was prepared as described in Example 20, using tetrahydrofuran-2-carbaldehyde in place of 2,3-dihydroxypropanal. $^1$H NMR (500 MHz, DMSO-$d_6$) δ 1.45-1.64 (m, 1H) 1.74-1.98 (m, 2H) 1.98-2.17 (m, 1H) 2.84 (s, 2H) 3.10-3.49 (m, 3H) 3.59-3.89 (m, 6H) 3.96 (d, J=14.65 Hz, 1H) 4.14 (t, J=15.41 Hz, 1H) 4.23-4.38 (m, 1H) 6.49-6.64 (m, 2H) 7.28 (dd, J=8.54, 4.27 Hz, 1H) 7.36-7.46 (m, 2H) 8.91 (s, 1H) 10.01 (s, 1H) 12.73 (s, 1H). MS (ESI$^+$) m/z 409.2 (M+H)$^+$.

Example 25

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide The title compound was prepared as described in Example 20, using N-(4-formylphenyl)acetamide in place of 2,3-dihydroxypropanal. $^1$H NMR (500 MHz, DMSO-$d_6$) δ 1.95-2.14 (m, 3H) 2.67-2.97 (m, 2H) 3.25 (s, 1H) 3.63 (d, J=10.07 Hz, 1H) 3.79 (s, 3H) 3.85-3.93 (m, 2H) 4.37 (d, J=7.32 Hz, 2H) 6.36-6.65 (m, 2H) 7.27 (dd, J=8.70, 4.43 Hz, 1H) 7.36-7.43 (m, 2H) 7.46 (d, J=8.54 Hz, 2H) 7.68 (d, J=8.24 Hz, 2H) 8.89 (s, 1H) 9.96-10.20 (m, 2H) 12.70 (s, 1H). MS (ESI$^+$) m/z 472.2 (M+H)$^+$.

Example 26

4-(5-fluoro-2-methoxyphenyl)-6-[1-(pyridin-2-ylmethyl)-1,2,3,6-tetrahydropyridin-4-yl]-7H-pyrrolo[2,3-d]pyrimidine The title compound was prepared as described in Example 20, using picolinaldehyde in place of 2,3-dihydroxypropanal. $^1$H NMR (500 MHz, DMSO-$d_6$) δ 2.86 (s, 2H) 3.54 (t, J=5.49 Hz, 2H) 3.80 (s, 3H) 4.04 (s, 2H) 4.61 (s, 2H) 6.56 (s, 1H) 6.61 (s, 1H) 7.29 (dd, J=8.85, 3.97 Hz, 1H) 7.38-7.46 (m, 2H) 7.51 (dd, J=7.02, 4.88 Hz, 1H) 7.59 (d, J=7.63 Hz, 1H) 7.81-8.08 (m, 1H) 8.71 (d, J=4.27 Hz, 1H) 8.93 (s, 1H) 12.82 (s, 1H). MS (ESI$^+$) m/z 416.1 (M+H)$^+$.

Example 27

4-(5-fluoro-2-methoxyphenyl)-6-[1-(pyridin-4-ylmethyl)-1,2,3,6-tetrahydropyridin-4-yl]-7H-pyrrolo[2,3-d]pyrimidine The title compound was prepared as described in Example 20, using isonicotinaldehyde in place of 2,3-dihydroxypropanal. The compound was purified after HPLC by flash chromatography on silica (Analogix 280) eluting with 7.5% methanol/dichloromethane with ammonium hydroxide to give the title compound. $^1$H NMR (400 MHz, DMSO-$d_6$) δ 2.64 (t, J=5.65 Hz, 2H) 3.16 (d, J=2.44 Hz, 2H) 3.64 (s, 2H) 3.78 (s, 3H) 6.29 (d, J=1.53 Hz, 1H) 6.55 (s, 1H) 7.11-7.43 (m, 5H) 8.52 (d, J=6.10 Hz, 2H) 8.77 (s, 1H) 12.22 (s, 1H). MS (ESI$^+$) m/z 416.2 (M+H)$^+$.

Example 28

4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine The title compound was prepared as described in Example 20, using 2-(trifluoromethyl)isonicotinaldehyde in place of 2,3-dihydroxypropanal. $^1$H NMR (400 MHz, DMSO-$d_6$) δ 2.84 (s, 2H) 3.73-3.87 (m, 3H) 3.88-4.01 (m, 2H) 4.58 (s, 2H) 6.47-6.61 (m, 2H) 7.21-7.34 (m, 1H) 7.33-7.47 (m, 2H) 7.89 (d, J=4.88 Hz, 1H) 8.13 (s, 1H) 8.75-9.03 (m, 2H) 12.72 (s, 1H). MS (ESI$^+$) m/z 484.2 (M+H)$^+$.

Example 29

N-benzyl-4-fluoro-3-{6-[1-(methylsulfonyl)-1,2,3,6-tetrahydropyridin-4-yl]-7H-pyrrolo[2,3-d]pyrimidin-4-yl}aniline

Example 29A 4-chloro-6-(1-(methylsulfonyl)-1,2,3,6-tetrahydropyridin-4-yl)-7-(phenylsulfonyl)-7H-pyrrolo[2,3-d]pyrimidine To a solution of 4-chloro-6-iodo-7-(phenylsulfonyl)-7H-pyrrolo[2,3-d]pyrimidine (1.9 g, 4.53 mmol) in 6:1 tetrahydrofuran/water (60 mL) was added 1-(methylsulfonyl)-4-(4,4,5,5-tetramethyl-1,3,2-dioxaborolan-2-yl)-1,2,3,6-tetrahydropyridine (1.56 g, 5.43 mmol), [1,1'-bis(diphenylphosphino)ferrocene]dichloropalladium(II)-dichloromethane complex (0.37 g, 0.453 mmol) and cesium carbonate (3.54 g, 10.87 mmol). The mixture was heated at 50° C. overnight, cooled and diluted with 50 mL ethyl acetate. The organic layer was washed with saturated aqueous sodium bicarbonate, water, and brine, dried over magnesium sulfate, filtered, and concentrated. Purification by flash chromatography on silica (Analogix 280) eluting with a gradient of 10% to 60% ethyl acetate/hexanes gave the title compound. MS (ESI$^+$) m/z 452.5 (M)$^+$.

Example 29B 4-fluoro-3-(6-(1-(methylsulfonyl)-1,2,3,6-tetrahydropyridin-4-yl)-7H-pyrrolo[2,3-d]pyrimidin-4-yl)aniline To a solution of Example 29A (1.10 g, 2.429 mmol), 4-fluoro-3-(4,4,5,5-tetramethyl-1,3,2-dioxaborolan-2-yl)aniline (749 mg, 3.16 mmol), and bis(triphenylphosphine)palladium(II) dichloride (170 mg, 0.243 mmol) in 7/2/3 1,2-dimethyoxyethane/ethanol/water (30 mL) was added sodium carbonate (3.64 mL, 7.29 mmol). The mixture was heated at 90° C. for 1 hour, cooled and diluted with 50 mL ethyl acetate. The organic layer was washed with saturated aqueous sodium bicarbonate, water, and brine, dried over magnesium sulfate, filtered, and concentrated. The residue was dissolved in 30 mL dioxane, treated with 6M sodium hydroxide (4.05 mL, 24.29 mmol), heated at 100° C. for 1 hour, cooled and diluted with 50 mL ethyl acetate. The organic layer was washed with saturated aqueous sodium bicarbonate, water and brine, dried over magnesium sulfate, filtered, and concentrated. The residue was triturated with ethyl acetate to give the title compound. MS (ESI$^+$) m/z 388.2 (M+H)$^+$.

Example 29C

N-benzyl-4-fluoro-3-{6-[1-(methylsulfonyl)-1,2,3,6-tetrahydropyridin-4-yl]-7H-pyrrolo[2,3-d]pyrimidin-4-yl}aniline The title compound was prepared as described in Example 20, using Example 29B in place of Example 3, and benzaldehyde in place of 2,3-dihydroxypropanal. $^1$H NMR (500 MHz, DMSO-$d_6$) δ 2.54-2.64 (m, 2H) 2.96 (s, 3H) 3.39 (t, J=5.80 Hz, 2H) 3.87-4.02 (m, 2H) 4.32 (s, 2H) 6.44 (s, 1H) 6.64 (s, 1H) 6.78-6.87 (m, 1H) 6.94 (dd, J=5.95, 2.90 Hz, 1H) 7.12-7.21 (m, 1H) 7.24 (t, J=7.17 Hz, 1H) 7.29-7.40 (m, 4H) 8.90 (s, 1H) 12.76 (s, 1H). MS (ESI$^+$) m/z 478.2 (M+H)$^+$.

Example 30

4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile The title compound was prepared as described in Example 20, using Example 29B in place of Example 3, and 4-formylbenzonitrile in place of 2,3-dihydroxypropanal. $^1$H NMR (500 MHz, DMSO-$d_6$) δ 2.59 (s, 2H) 2.95 (s, 3H) 3.40 (t, J=5.65 Hz, 2H) 3.80-4.02 (m, 2H) 4.43 (s, 2H) 6.43 (s, 1H) 6.63 (s, 1H) 6.71-6.81 (m, 1H) 6.91 (dd, J=5.95, 2.90 Hz, 1H) 7.10-7.21 (m, 1H) 7.56 (d, J=8.24 Hz, 2H) 7.81 (d, J=8.24 Hz, 2H) 8.88 (s, 1H) 12.68 (s, 1H). MS (ESI$^+$) m/z 503.2 (M+H)$^+$.

Example 31

3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile The title compound was prepared as described in Example 20, using Example 29B in place of Example 3, and 3-formylbenzonitrile in place of 2,3-dihydroxypropanal. $^1$H NMR (500 MHz, DMSO-$d_6$) δ 2.60 (s, 2H) 2.96 (s, 3H) 3.39 (t, J=5.65 Hz, 2H) 3.89-3.99 (m, 2H) 4.31-4.44 (m, 2H) 6.43 (s, 1H) 6.63 (s, 1H) 6.74-6.84 (m, 1H) 6.94 (dd, J=5.80, 3.05 Hz, 1H) 7.11-7.22 (m, 1H) 7.56 (t, J=7.63 Hz, 1H) 7.68-7.77 (m, 2H) 7.82 (s, 1H) 8.88 (s, 1H) 12.68 (s, 1H). MS (ESI$^+$) m/z 503.2 (M+H)$^+$.

Example 32

4-fluoro-3-{6-[1-(methyl sulfonyl)-1,2,3,6-tetrahydropyridin-4-yl]-7H-pyrrolo[2,3-d]pyrimidin-4-yl}-N-(tetrahydrofuran-2-ylmethyl)aniline The title compound was prepared as described in Example 20, using Example 29B in place of Example 3, and tetrahydrofuran-2-carbaldehyde in place of 2,3-dihydroxypropanal. $^1$H NMR (500 MHz, DMSO-$d_6$) δ 1.52-1.68 (m, 1H) 1.73-1.92 (m, 2H) 1.92-2.06 (m, 1H) 2.66 (s, 2H) 2.96 (s, 3H) 3.02-3.23 (m, 2H) 3.40 (t, J=5.80 Hz, 2H) 3.57-3.71 (m, 1H) 3.73-3.85 (m, 1H) 3.91-4.08 (m, 3H) 6.67 (d, J=25.94 Hz, 3H) 6.88-7.07 (m, 2H) 7.16-7.28 (m, 1H) 8.98 (s, 1H) 12.96 (s, 1H). MS (ESI$^+$) m/z 472.2 (M+H)$^+$.

Example 33

4-fluoro-3-{6-[1-(methyl sulfonyl)-1,2,3,6-tetrahydropyridin-4-yl]-7H-pyrrolo[2,3-d]pyrimidin-4-yl}-N-(pyridin-2-ylmethyl)aniline The title compound was prepared as described in Example 20, using Example 29B in place of Example 3, and picolinaldehyde in place of 2,3-dihydroxypropanal. $^1$H NMR (500 MHz, DMSO-$d_6$) δ 2.60 (s, 2H) 2.96 (s, 3H) 3.39 (t, J=5.65 Hz, 2H) 3.85-4.02 (m, 2H) 4.59 (s, 2H) 6.45 (s, 1H) 6.63 (s, 1H) 6.76-6.90 (m, 1H) 6.98 (dd, J=5.80, 3.05 Hz, 1H) 7.12-7.25 (m, 1H) 7.56-7.67 (m, 1H) 7.72 (d, J=7.93 Hz, 1H) 8.18 (t, J=7.32 Hz, 1H) 8.70 (d, J=4.88 Hz, 1H) 8.88 (s, 1H) 12.68 (s, 1H). MS (ESI$^+$) m/z 479.2 (M+H)$^+$.

Example 34

4-(5-fluoro-2-methoxyphenyl)-6-[1-(pyridin-3-ylmethyl)-1,2,3,6-tetrahydropyridin-4-yl]-7H-pyrrolo[2,3-d]pyrimidine The title compound was prepared as described in Example 20, using nicotinaldehyde in place of 2,3-dihydroxypropanal. Purification by flash chromatography on silica (Analogix 280) eluting with a gradient of 2% to 10% methanol/dichloromethane gave the title compound. $^1$H NMR (400 MHz, DMSO-$d_6$) δ 2.74 (t, J=5.65 Hz, 2H) 3.24 (d, J=2.44 Hz, 2H) 3.73 (s, 2H) 3.88 (s, 3H) 6.38 (d, J=1.53 Hz, 1H) 6.65 (s, 1H) 7.26-7.37 (m, 1H) 7.38-7.54 (m, 3H) 7.79-7.90 (m, 1H) 8.59 (dd, J=4.88, 1.53 Hz, 1H) 8.64 (d, J=1.53 Hz, 1H) 8.87 (s, 1H) 12.32 (d, J=1.22 Hz, 1H). MS (ESI$^+$) m/z 416.2 (M+H)$^+$.

Example 35

6-[1-(3-fluorobenzyl)-1,2,3,6-tetrahydropyridin-4-yl]-4-(5-fluoro-2-methoxyphenyl)-7H-pyrrolo[2,3-d]pyrimidine The title compound was prepared as described in Example 20, using 3-fluorobenzaldehyde in place of 2,3-dihydroxypropanal. Purification by flash chromatography on silica (Analogix 280) eluting with a gradient of 2% to 10% methanol/dichloromethane gave the title compound. $^1$H NMR (400 MHz, DMSO-$d_6$) δ 2.64 (t, J=5.65 Hz, 2H) 3.13 (d, J=2.75 Hz, 2H) 3.62 (s, 2H) 3.78 (s, 3H) 6.28 (d, J=1.83 Hz, 1H) 6.54 (s, 1H) 7.01-7.27 (m, 4H) 7.28-7.44 (m, 3H) 8.77 (s, 1H) 12.21 (s, 1H). MS (ESI$^+$) m/z 433.2 (M+H)$^+$.

Example 36

6-[1-(3,5-difluorobenzyl)-1,2,3,6-tetrahydropyridin-4-yl]-4-(5-fluoro-2-methoxyphenyl)-7H-pyrrolo[2,3-d]pyrimidine The title compound was prepared as described in Example 20, using 3,5-difluorobenzaldehyde in place of 2,3-dihydroxypropanal. Purification by flash chromatography on silica (Analogix 280) eluting with a gradient of 2% to 10% methanol/dichloromethane gave the title compound. $^1$H NMR (400 MHz, DMSO-$d_6$) δ 2.65 (t, J=5.49 Hz, 2H) 3.15 (d, J=2.75 Hz, 2H) 3.64 (s, 2H) 3.78 (s, 3H) 6.28 (d, J=1.83 Hz, 1H) 6.54 (s, 1H) 6.99-7.17 (m, 3H) 7.17-7.27 (m, 1H) 7.28-7.39 (m, 2H) 8.76 (s, 1H) 12.21 (s, 1H). MS (ESI$^+$) m/z 451.2 (M+H)$^+$.

Example 37

4-fluoro-3-{6-[1-(methyl sulfonyl)-1,2,3,6-tetrahydropyridin-4-yl]-7H-pyrrolo[2,3-d]pyrimidin-4-yl}-N-(pyridin-4-ylmethyl)aniline The title compound was prepared as described in Example 20, using Example 29B in place of Example 3, and isonicotinaldehyde in place of 2,3-dihydroxypropanal. Purification by flash chromatography on silica (Analogix 280) eluting with a gradient of 1% to 10% methanol/dichloromethane gave the title compound. $^1$H NMR (500 MHz, DMSO-$d_6$) δ 2.57 (s, 2H) 2.95 (s, 3H) 3.39 (q, J=5.90 Hz, 2H) 3.93 (d, J=2.44 Hz, 3H) 4.49 (s, 2H) 6.34 (s, 1H) 6.59 (s, 1H) 6.65-6.80 (m, 1H) 6.91 (dd, J=5.80, 3.05 Hz, 1H) 7.14 (t, J=9.61 Hz, 1H) 7.62 (d, J=5.80 Hz, 2H) 8.65 (d, J=5.80 Hz, 2H) 8.79 (s, 1H) 12.42 (s, 1H). MS (ESI$^+$) m/z 478.2. (M)$^+$.

Example 38

6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine The title compound was prepared as described in Example 5, using tetrahydrothiophene-3-sulfonyl chloride 1,1-dioxide in place of methanesulfonyl chloride. Purification by flash chromatography on silica (Analogix 280) eluting with a gradient of 1% to 6% methanol/dichloromethane gave the title compound. $^1$H NMR (500 MHz, DMSO-d$_6$) δ 2.20-2.35 (m, 1H) 2.60 (s, 2H) 3.07-3.24 (m, 2H) 3.34-3.41 (m, 1H) 3.47-3.57 (m, 2H) 3.62 (dd, J=13.43, 8.85 Hz, 1H) 3.78 (s, 3H) 4.06 (d, J=2.44 Hz, 2H) 4.25-4.42 (m, 1H) 6.37 (s, 1H) 6.57 (s, 1H) 7.17-7.28 (m, 1H) 7.29-7.40 (m, 2H) 8.79 (s, 1H) 12.31 (s, 1H). MS (ESI$^+$) m/z 507.1 (M+H)$^+$.

Example 39

4-(5-fluoro-2-methoxyphenyl)-6-[1-(piperidin-4-ylmethyl)-1,2,3,6-tetrahydropyridin-4-yl]-7H-pyrrolo[2,3-d]pyrimidine The title compound was prepared as described in Example 20, using tert-butyl 4-formylpiperidine-1-carboxylate in place of 2,3-dihydroxypropanal. Purification by flash chromatography on silica (Analogix 280) eluting with a gradient of 40% to 80% ethyl acetate/hexanes gave an oily residue which was taken up in 5 mL dichloromethane and treated with excess trifluoroacetic acid for 1 hour. The solvent was removed and the residue dried under vacuum to give the title compound. $^1$H NMR (400 MHz, DMSO-d$_6$) δ 1.29-1.51 (m, 2H) 1.79-2.08 (m, 2H) 2.10-2.31 (m, 1H) 2.75-3.01 (m, 4H) 3.17 (s, 2H) 3.33 (d, J=12.51 Hz, 3H) 3.70 (s, 1H) 3.82 (s, 3H) 3.90 (d, J=12.82 Hz, 1H) 4.23 (d, J=14.95 Hz, 1H) 6.62 (s, 1H) 6.69 (s, 1H) 7.25-7.36 (m, 1H) 7.39-7.51 (m, 2H) 8.56 (d, J=9.77 Hz, 1H) 8.81 (d, J=10.38 Hz, 1H) 8.99 (s, 1H) 10.14 (s, 1H) 13.01 (s, 1H). MS (ESI$^+$) m/z 422.2 (M+H)$^+$.

Example 40

4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine The title compound was prepared as described in Example 5, using 2,2,2-trifluoromethanesulfonyl chloride in place of methanesulfonyl chloride. Purification by flash chromatography on silica (Analogix 280) eluting with a gradient of 40% to 100% ethyl acetate/hexanes gave the title compound. $^1$H NMR (400 MHz, DMSO-d$_6$) δ 2.66 (d, J=1.22 Hz, 2H) 3.65-3.84 (m, 5H) 4.27 (s, 2H) 6.41 (s, 1H) 6.59 (s, 1H) 7.17-7.28 (m, 1H) 7.29-7.41 (m, 2H) 8.80 (s, 1H) 12.36 (s, 1H). MS (ESI$^+$) m/z 457.2 (M+H)$^+$.

Example 41

4-(5-chloro-2-fluoro-3-methylphenyl)-6-[1-(methylsulfonyl)-1,2,3,6-tetrahydropyridin-4-yl]-7H-pyrrolo[2,3-d]pyrimidine

Example 41A 4-chloro-6-(1-(methylsulfonyl)-1,2,3,6-tetrahydropyridin-4-yl)-7H-pyrrolo[2,3-d]pyrimidine The title compound was prepared essentially as described in Example 3E, substituting Example 3D with Example 29A. MS (ESI$^+$) m/z 313.1 (M+H)$^+$.

Example 41B 4-(5-chloro-2-fluoro-3-methylphenyl)-6-[1-(methylsulfonyl)-1,2,3,6-tetrahydropyridin-4-yl]-7H-pyrrolo[2,3-d]pyrimidine A 4 mL vial was charged with a stir bar, a solution of Example 41A (27.50 mg, 0.09 mmol) in 1 mL of ethanol, a solution of (5-chloro-2-fluoro-3-methylphenyl)boronic acid (24.85 mg, 1.5 eq, 0.13 mmol) in 220 µL of ethanol, a 1.0 M aqueous solution of cesium carbonate (175.84 µL, 2 eq, 0.18 mmol), and Siliacat® DPP-Pd (Silicycle®, 0.27 mmol/g loading, 32.56 mg). The loaded vial was seal capped and placed in an Anton Paar Synthos 3000 microwave reactor (900 W maximum) and heated to 120° C. for 15 minutes. Upon completion, the solids were collected by filtration and dried under vacuum. The dried material was then re-dissolved in 1.4 mL of dimethyl sulfoxide/methanol 1:1 (v/v) solution, and purified by preparative HPLC on a Phenomenex® Luna® C8(2) 5 µm 100A AXIA™ column (30 mm×75 mm) A gradient of acetonitrile (A) and 0.1% trifluoroacetic acid in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A) to yield the title compound. $^1$H NMR (400 MHz, DMSO-d$_6$/D$_2$O) δ 2.37 (d, J=2.1 Hz, 3H), 2.65 (s, 2H), 2.95 (d, J=5.2 Hz, 3H), 3.18 (s, 1H), 3.40 (t, J=5.7 Hz, 2H), 3.95 (d, J=3.4 Hz, 2H), 6.57 (d, J=3.8 Hz, 1H), 6.59-6.64 (m, 1H), 7.60 (d, J=5.8 Hz, 2H), 8.85 (s, 1H). MS (ESI$^+$) m/z 421.1 (M+H)$^+$. Examples 42 through 59 were prepared essentially as described in Example 41B, substituting the appropriate boronic acid.

Example 42

4-(2-butoxy-5-fluorophenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 0.75 (t, J=7.4 Hz, 3H), 1.14-1.24 (m, 2H), 1.54 (dq, J=8.2, 6.4 Hz, 2H), 2.61-2.67 (m, 2H), 2.95 (s, 3H), 3.41 (t, J=5.7 Hz, 2H), 3.96 (q, J=2.8 Hz, 2H), 4.05 (t, J=6.4 Hz, 2H), 6.63-6.73 (m, 2H), 7.31 (dd, J=8.9, 4.4 Hz, 1H), 7.41-7.49 (m, 2H), 8.98 (s, 1H). MS (ESI$^+$) m/z 445.2 (M+H)$^+$.

Example 43

4-[5-methyl-2-(propan-2-yloxy)phenyl]-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 1.17 (d, J=6.0 Hz, 6H), 2.35 (s, 3H), 2.65 (s, 2H), 2.95 (s, 3H), 3.41 (t, J=5.6 Hz, 2H), 3.97 (q, J=2.7 Hz, 2H), 4.66 (p, J=6.0 Hz, 1H), 6.66-6.74 (m, 2H), 7.17-7.24 (m, 1H), 7.41-7.47 (m, 2H), 9.00 (s, 1H). MS (ESI$^+$) m/z 427.2 (M+H)$^+$.

Example 44

4-(2-methoxy-5-methylphenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.36 (s, 3H), 2.67 (s, 2H), 2.95 (s, 3H), 3.41 (t, J=5.7 Hz, 2H), 3.82 (s, 3H), 3.97 (q, J=2.8 Hz, 2H), 6.70 (dt, J=4.1, 2.3 Hz, 1H), 6.73 (s, 1H), 7.21-7.25 (m, 1H), 7.49 (d, J=7.3 Hz, 2H), 9.00 (s, 1H). MS (ESI$^+$) m/z 399.1 (M+H)$^+$.

Example 45

4-(5-chloro-2-methoxyphenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.65 (s, 2H), 2.95 (s, 3H), 3.40 (t, J=5.6 Hz, 2H), 3.83 (s, 3H), 3.96 (d, J=3.4 Hz, 2H), 6.59 (s, 1H), 6.63-6.68 (m, 1H), 7.32 (d, J=8.9 Hz, 1H), 7.59-7.69 (m, 2H), 8.93 (s, 1H). MS (ESI$^+$) m/z 419.0 (M+H)$^+$.

Example 46

4-(2,4-difluorophenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.65 (s, 2H), 2.95 (s, 3H), 3.40 (t, J=5.7 Hz, 2H), 3.95 (dt, J=5.3, 3.1 Hz, 2H), 6.59 (d, J=3.5 Hz, 1H), 6.61-6.63 (m, 1H), 7.33 (td, J=8.2, 2.5 Hz, 1H), 7.47 (ddd, J=11.1, 9.3, 2.5 Hz, 1H), 7.89 (td, J=8.6, 6.7 Hz, 1H), 8.87 (d, J=4.7 Hz, 1H). MS (ESI$^+$) m/z 391.1 (M+H)$^+$.

Example 47

6-[1-(methylsulfonyl)-1,2,3,6-tetrahydropyridin-4-yl]-4-[2-(trifluoromethyl)phenyl]-7H-pyrrolo[2,3-d]pyrimidine $^1$H NMR (400 MHz, DMSO-d$_6$/D$_2$O) δ 2.58 (d, J=5.1 Hz, 2H), 2.93 (s, 3H), 3.37 (t, J=5.7 Hz, 2H), 3.93 (q, J=2.6 Hz, 2H), 6.34 (s, 1H), 6.59 (d, J=3.8 Hz, 1H), 7.65 (d, J=7.2 Hz, 1H), 7.82 (dt, J=26.8, 7.4 Hz, 2H), 7.91-8.02 (m, 1H), 8.82 (s, 1H). MS (ESI$^+$) m/z 423.0 (M+H)$^+$.

Example 48

N-(3-{6-[1-(methylsulfonyl)-1,2,3,6-tetrahydropyridin-4-yl]-7H-pyrrolo[2,3-d]pyrimidin-4-yl}phenyl)methanesulfonamide $^1$H NMR (400 MHz, DMSO-d$_6$/D$_2$O) δ 2.70 (s, 2H), 2.96 (s, 3H), 3.06 (s, 3H), 3.44 (t, J=5.7 Hz, 2H), 3.96 (d, J=3.5 Hz, 2H), 6.63 (s, 1H), 6.94 (s, 1H), 7.41 (dd, J=7.2, 2.1 Hz, 1H), 7.60 (t, J=7.9 Hz, 1H), 7.94 (d, J=7.9 Hz, 1H), 8.05 (t, J=2.0 Hz, 1H), 8.84 (s, 1H). MS (ESI$^+$) m/z 448.1 (M+H)$^+$.

Example 49

4-(5-fluoro-2-propoxyphenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 0.75 (t, J=7.4 Hz, 3H), 1.57 (h, J=7.0 Hz, 2H), 2.63 (s, 2H), 2.94 (s, 3H), 3.40 (t, J=5.7 Hz, 2H), 3.95 (t, J=3.1 Hz, 2H), 4.01 (t, J=6.4 Hz, 2H), 6.64 (d, J=6.6 Hz, 2H), 7.25-7.31 (m, 1H), 7.41-7.46 (m, 2H), 8.94 (s, 1H). MS (ESI$^+$) m/z 431.1 (M+H)$^+$.

Example 50

4-(2-fluoro-5-methylphenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.40 (s, 3H), 2.65 (s, 2H), 2.95 (s, 3H), 3.40 (t, J=5.7 Hz, 2H), 3.94 (dd, J=6.2, 3.5 Hz, 2H), 6.58 (d, J=3.5 Hz, 1H), 6.62 (d, J=3.9 Hz, 1H), 7.30-7.37 (m, 1H), 7.45 (ddd, J=7.8, 5.0, 2.3 Hz, 1H), 7.60 (dd, J=7.0, 2.3 Hz, 1H), 8.89 (s, 1H). MS (ESI$^+$) m/z 387.1 (M+H)$^+$.

Example 51

4-[2-fluoro-5-(trifluoromethyl)phenyl]-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.65 (s, 2H), 2.95 (d, J=5.3 Hz, 3H), 3.40 (t, J=5.8 Hz, 2H), 3.95 (s, 2H), 6.57 (d, J=4.2 Hz, 1H), 6.62 (d, J=3.9 Hz, 1H), 7.70 (t, J=9.4 Hz, 1H), 8.04 (d, J=11.2 Hz, 1H), 8.14 (dd, J=6.5, 2.5 Hz, 1H), 8.89 (s, 1H). MS (ESI$^+$) m/z 441.1 (M+H)$^+$.

Example 52

4-[2-fluoro-5-(propan-2-yloxy)phenyl]-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 1.30 (d, J=6.0 Hz, 6H), 2.64 (s, 2H), 2.94 (s, 3H), 3.40 (t, J=5.7 Hz, 2H), 3.95 (d, J=3.5 Hz, 2H), 4.63 (p, J=5.9 Hz, 1H), 6.55 (d, J=3.7 Hz, 1H), 6.61 (d, J=3.8 Hz, 1H), 7.16 (dt, J=9.1, 3.6 Hz, 1H), 7.25 (dd, J=5.7, 3.1 Hz, 1H), 7.32-7.40 (m, 1H), 8.87 (d, J=4.8 Hz, 1H). MS (ESI$^+$) m/z 431.1 (M+H)$^+$.

Example 53

4-(5-methyl-2-propoxyphenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 0.77 (t, J=7.4 Hz, 3H), 1.59 (h, J=7.1 Hz, 2H), 2.35 (s, 3H), 2.64 (s, 2H), 2.95 (s, 3H), 3.41 (t, J=5.7 Hz, 2H), 3.97 (q, J=2.9 Hz, 2H), 4.01 (t, J=6.4 Hz, 2H), 6.65-6.71 (m, 2H), 7.17-7.22 (m, 1H), 7.44 (dd, J=6.0, 2.4 Hz, 2H), 8.99 (s, 1H). MS (ESI$^+$) m/z 427.1 (M+H)$^+$.

Example 54

4-(5-butoxy-2-fluorophenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 0.94 (t, J=7.4 Hz, 3H), 1.40-1.49 (m, 2H), 1.68-1.75 (m, 2H), 2.64 (s, 2H), 2.95 (d, J=5.8 Hz, 3H), 3.40 (t, J=5.7 Hz, 2H), 3.95 (d, J=3.6 Hz, 2H), 4.03 (t, J=6.4 Hz, 2H), 6.55 (d, J=3.7 Hz, 1H), 6.60-6.65 (m, 1H), 7.17 (dt, J=9.1, 3.6 Hz, 1H), 7.26 (dd, J=5.7, 3.2 Hz, 1H), 7.33-7.39 (m, 1H), 8.87 (d, J=5.0 Hz, 1H). MS (ESI$^+$) m/z 445.1 (M+H)$^+$.

Example 55

4-(2-fluoro-3-methoxyphenyl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.60 (m, 2H), 2.94 (s, 3H), 3.37 (d, J=5.8 Hz, 2H), 3.69 (s, 6H), 3.94 (s, 2H), 6.35 (s, 1H), 6.62 (s, 1H), 6.87 (d, J=8.5 Hz, 2H), 7.54 (t, J=8.5 Hz, 1H), 8.90 (s, 1H). MS (ESI$^+$) m/z 403.1 (M+H)$^+$.

Example 56

6-[1-(methylsulfonyl)-1,2,3,6-tetrahydropyridin-4-yl]-4-[3-(trifluoromethoxy)phenyl]-7H-pyrrolo[2,3-d]pyrimidine $^1$H NMR (400 MHz, DMSO-d$_6$/D$_2$O) δ 2.71 (d, J=6.4 Hz, 2H), 2.96 (s, 3H), 3.43 (t, J=5.7 Hz, 2H), 3.96 (d, J=3.6 Hz, 2H), 6.64 (s, 1H), 6.96 (s, 1H), 7.58 (d, J=7.8 Hz, 1H), 7.76 (td, J=8.1, 4.0 Hz, 1H), 8.08 (s, 1H), 8.24 (dt, J=7.8, 1.2 Hz, 1H), 8.85 (s, 1H). MS (ESI$^+$) m/z 439.1 (M+H)$^+$.

Example 57

4-(1-methyl-1H-pyrazol-4-yl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.74 (s, 2H), 2.96 (s, 3H), 3.44 (s, 2H), 3.96 (s, 2H), 3.97 (s, 3H), 6.58 (s, 1H), 7.03 (s, 1H), 8.31 (s, 1H), 8.67 (d, J=4.3 Hz, 2H). MS (ESI$^+$) m/z 359.1 (M+H)$^+$.

Example 58

6-[1-(methylsulfonyl)-1,2,3,6-tetrahydropyridin-4-yl]-4-[2-(trifluoromethoxy)phenyl]-7H-pyrrolo[2,3-d]pyrimidine $^1$H NMR (400 MHz, DMSO-d$_6$/D$_2$O) δ 2.62 (s, 2H), 2.94 (s, 3H), 3.39 (t, J=5.7 Hz, 2H), 3.92-3.96 (m, 2H), 6.48 (s, 1H), 6.60-6.64 (m, 1H), 7.59-7.66 (m, 2H), 7.73 (td, J=7.8, 1.9 Hz, 1H), 7.81 (dd, J=7.6, 1.8 Hz, 1H), 8.87 (s, 1H). MS (ESI$^+$) m/z 439.1 (M+H)$^+$.

Example 59

4-(4-methoxypyridin-3-yl)-6-[1-(methylsulfonyl)-1,2,3,6-tetrahydropyridin-4-yl]-7H-pyrrolo[2,3-d]pyrimidine $^1$H NMR (400 MHz, DMSO-d$_6$/D$_2$O) δ 2.64 (s, 2H), 2.95 (s, 3H), 3.41 (t, J=5.7 Hz, 2H), 3.95 (d, J=4.8 Hz, 2H), 4.11 (s, 3H), 6.59 (s, 1H), 6.62 (s, 1H), 7.75 (d, J=6.8 Hz, 1H), 8.82-8.87 (m, 1H), 8.87-8.92 (m, 2H). MS (ESI$^+$) m/z 386.1 (M+H)$^+$.

Example 60

6-[1-(methylsulfonyl)-1,2,3,6-tetrahydropyridin-4-yl]-4-(morpholin-4-yl)-7H-pyrrolo[2,3-d]pyrimidine To a solution of Example 41A (100 mg, 0.320 mmol) and morpholine (2.52 mL, 3 mmol) in 3 mL tetrahydrofuran/1 mL N,N-dimethylformamide was added N-ethyl-N-isopropylpropan-2-amine (0.084 mL, 0.480 mmol). The resulting reaction was stirred at 60° C. overnight. The solvent was removed in vacuo and the residue dried under high-vacuum for 2 hours. The crude solid was triturated with ethyl acetate, collected by filtration, and dried under high-vacuum to give the title compound. $^1$H NMR (500 MHz, DMSO-d$_6$) δ 11.93 (s, 1H) 8.17 (s, 1H) 6.68 (s, 1H) 6.41 (s, 1H) 3.66-3.93 (m, 8H) 3.37 (t, J=5.65 Hz, 2H) 3.02-3.12 (m, 2H) 2.89-2.98 (m, 3H) 2.62 (s, 2H). MS (ESI$^+$) m/z 364.2 (M+H)$^+$.

Example 61

6-(4,4-difluorocyclohex-1-en-1-yl)-4-(5-fluoro-2-methoxyphenyl)-7H-pyrrolo[2,3-d]pyrimidine

Example 61A 4-(5-fluoro-2-methoxyphenyl)-6-iodo-7H-pyrrolo[2,3-d]pyrimidine

A solution of Example 3C (3.5 g, 6.78 mmol) in 70 mL dioxane was treated with aqueous sodium hydroxide (11.30 mL, 67.8 mmol, 6 M) and stirred at 100° C. for 1 hour. The reaction mixture was cooled and diluted with 300 mL of water. The aqueous mixture was extracted with ethyl acetate (3×), and the combined organic fractions were washed with brine, dried over magnesium sulfate and concentrated to give the title compound. MS (ESI$^+$) m/z 370.1 (M+H)$^+$.

Example 61B 6-(4,4-difluorocyclohex-1-en-1-yl)-4-(5-fluoro-2-methoxyphenyl)-7H-pyrrolo[2,3-d]pyrimidine To a solution of Example 61A (129 mg, 0.528 mmol), 2-(4,4-difluorocyclohex-1-en-1-yl)-4,4,5,5-tetramethyl-1,3,2-dioxaborolane (129 mg, 0.528 mmol), and bis(triphenylphosphine)palladium(II) dichloride (28.5 mg, 0.041 mmol) in 10 mL dimethoxyethane/ethanol/water (7/2/3) was added sodium carbonate (129 mg, 1.219 mmol). The reaction was stirred at 100° C. for 2 hours, cooled and then extracted with ethyl acetate. The organic fraction was washed with saturated sodium bicarbonate, water and brine, then dried over magnesium sulfate and concentrated. The crude material was triturated with ethyl acetate, and the solid was collected by filtration. The solid was purified via flash chromatography: Analogix Intelliflash™ 280, 24 g silica column, 20% to 60% ethyl acetate/hexanes gradient over 30 minutes to give the title compound. $^1$H NMR (400 MHz, DMSO-d$_6$) δ 12.27 (s, 1H) 8.65-8.90 (m, 1H) 7.09-7.48 (m, 3H) 6.45 (s, 1H) 6.37 (s, 1H) 3.73-3.82 (m, 3H) 2.80 (t, J=14.19 Hz, 2H) 2.69 (t, J=5.95 Hz, 2H) 2.08-2.27 (m, 2H). MS (ESI$^+$) m/z 360.2 (M+H)$^+$.

Example 62

6-[1-(methylsulfonyl)-1,2,3,6-tetrahydropyridin-4-yl]-4-(pyrrolidin-1-yl)-7H-pyrrolo[2,3-d]pyrimidine The title compound was prepared essentially as described in Example 60, substituting morpholine with pyrrolidine. $^1$H NMR (400 MHz, DMSO-$d_6$) δ 11.75 (s, 1H) 8.07 (s, 1H) 6.60 (d, J=1.83 Hz, 1H) 6.35 (s, 1H) 3.87 (d, J=2.75 Hz, 2H) 3.72 (s, 4H) 3.37 (t, J=5.65 Hz, 2H) 2.94 (s, 3H) 2.61 (s, 2H) 1.96 (s, 4H). MS (ESI$^+$) m/z 348.2 (M+H)$^+$.

Example 63

4-(4,4-difluoropiperidin-1-yl)-6-[1-(methylsulfonyl)-1,2,3,6-tetrahydropyridin-4-yl]-7H-pyrrolo[2,3-d]pyrimidine The title compound was prepared essentially as described in Example 60, substituting morpholine with 4,4-difluoropiperidine hydrochloride. $^1$H NMR (400 MHz, DMSO-$d_6$) δ 11.96 (s, 1H) 8.19 (s, 1H) 6.68 (d, J=1.22 Hz, 1H) 6.42 (s, 1H) 3.93-4.04 (m, 4H) 3.89 (d, J=2.14 Hz, 2H) 3.38 (t, J=5.65 Hz, 2H) 2.94 (s, 3H) 2.64 (s, 2H) 1.98-2.16 (m, 4H). MS (ESI$^+$) m/z 398.2 (M+H)$^+$.

Example 64

4-(3,3-difluoroazetidin-1-yl)-6-[1-(methylsulfonyl)-1,2,3,6-tetrahydropyridin-4-yl]-7H-pyrrolo[2,3-d]pyrimidine The title compound was prepared essentially as described in Example 60, substituting morpholine with 3,3-difluoroazetidine hydrochloride. $^1$H NMR (400 MHz, DMSO-$d_6$) δ 12.01 (s, 1H) 8.21 (s, 1H) 6.51 (s, 1H) 6.40-6.45 (m, 1H) 4.70 (t, J=12.51 Hz, 4H) 3.89 (d, J=3.05 Hz, 2H) 3.38 (t, J=5.80 Hz, 2H) 2.94 (s, 3H) 2.61 (s, 2H). MS (ESI$^+$) m/z 370.1 (M+H)$^+$.

Example 65

6-(3,6-dihydro-2H-pyran-4-yl)-4-(5-fluoro-2-methoxyphenyl)-7H-pyrrolo[2,3-d]pyrimidine The title compound was prepared essentially as described in Example 61B, substituting 2-(4,4-difluorocyclohex-1-en-1-yl)-4,4,5,5-tetramethyl-1,3,2-dioxaborolane with 2-(3,6-dihydro-2H-pyran-4-yl)-4,4,5,5-tetramethyl-1,3,2-dioxaborolane. $^1$H NMR (400 MHz, DMSO-$d_6$) δ 12.27 (s, 1H) 8.70-8.87 (m, 1H) 7.28-7.40 (m, 2H) 7.16-7.27 (m, 1H) 6.62 (s, 1H) 6.32 (s, 1H) 4.28 (d, J=2.44 Hz, 2H) 3.72-3.87 (m, 5H) 2.46 (d, J=1.22 Hz, 2H). MS (ESI$^+$) m/z 326.1 (M+H)$^+$.

Example 66 tert-butyl 4-[4-(2-ethoxy-5-fluorophenyl)-7H-pyrrolo[2,3-d]pyrimidin-6-yl]-3,6-dihydropyridine-1(2H)-carboxylate

Example 66A tert-butyl 4-(4-(2-ethoxy-5-fluorophenyl)-7-(phenylsulfonyl)-7H-pyrrolo[2,3-d]pyrimidin-6-yl)-5,6-dihydropyridine-1(2H)-carboxylate A mixture of 2-(2-ethoxy-5-fluorophenyl)-4,4,5,5-tetramethyl-1,3,2-dioxaborolane (242 mg, 0.91 mmol), Example 75A (375 mg, 0.79 mmol), [1,1'-bis(diphenylphosphino)ferrocene]dichloropalladium(II)-dichloromethane adduct (64.5 mg, 0.079 mmol), and 1 M sodium carbonate solution (2.37 mL, 2.369 mmol) in dioxane (10 mL) was heated at 130° C. for 50 minutes and then cooled and diluted with ethyl acetate. The resulting mixture was washed with brine, and the organic fraction was dried over sodium sulfate and concentrated. The residue was purified by flash chromatography, eluted with a mixture of ethyl acetate and heptanes to provide the title compound. LC-MS (APCI$^+$) m/z 579.15 (M+H)$^+$.

Example 66B tert-butyl 4-[4-(2-ethoxy-5-fluorophenyl)-7H-pyrrolo[2,3-d]pyrimidin-6-yl]-3,6-dihydropyridine-1(2H)-carboxylate Example 66A (468 mg, 0.81 mmol) in a mixture of methanol (5 mL) and tetrahydrofuran (10 mL) was treated with 1 M NaOH (4.04 mL, 4.40 mmol) at 50° C. overnight. The reaction mixture was cooled and concentrated. The resulting concentrate was acidified with 5% hydrochloric acid to pH 4 and extracted with ethyl acetate. The organic fraction was dried over sodium sulfate and concentrated. The residue was dissolved in 1:1 dimethyl sulfoxide:methanol and loaded onto a C18 column, eluted with 20-80% acetonitrile in 0.1% aqueous trifluoroacetic acid solution at a flow rate of 50 mL/minute to provide the title compound. $^1$H NMR (400 MHz, DMSO-$d_6$) δ 12.26 (s, 1H) 8.79 (s, 1H) 7.28-7.37 (m, 2H) 7.18-7.23 (m, 1H) 6.55 (s, 1H) 6.41 (d, 1H) 4.10 (q, 4H) 3.54 (t, 2H) 2.46-2.50 (m, 2H) 1.42 (s, 9H) 1.16 (t, 3H). LC MS (APCI$^+$) m/z 439 (M+1)$^+$.

Example 67

4-(2-ethoxy-5-fluorophenyl)-6-(1,2,3,6-tetrahydropyridin-4-yl)-7H-pyrrolo[2,3-d]pyrimidine To a solution of Example 66B (220 mg, 0.502 mmol) in 5 mL dichloromethane was added 2,2,2-trifluoroacetic acid (0.387 ml, 5.02 mmol). The reaction was stirred at room temperature overnight. The solvent was removed under reduced pressure, and the residue was dried under high-vacuum for 2 hours. The residue was dissolved with 3 mL methanol, and the mixture was treated with excess 2 M hydrochloric acid/diethyl ether followed by stirring for 20 minutes. The mixture was then diluted with 50 mL diethyl ether, and the solid was collected by filtration. The collected solid was dried under high-vacuum to give the title compound as a hydrochloride salt. $^1$H NMR (400 MHz, DMSO-$d_6$) δ 13.48 (s, 1H) 9.64 (s, 2H) 9.08 (s, 1H) 7.42-7.59 (m, 2H) 7.32 (dd, J=9.16, 4.27 Hz, 1H) 6.80 (d, J=35.71 Hz, 2H) 4.15 (q, J=6.92 Hz, 3H) 3.84 (s, 2H) 3.31 (s, 2H) 2.77 (s, 1H) 1.07-1.28 (m, 3H). MS (ESI$^+$) m/z 339.1 (M+H)$^+$.

Example 68

N-[4-({4-[4-(2-ethoxy-5-fluorophenyl)-7H-pyrrolo[2,3-d]pyrimidin-6-yl]-3,6-dihydropyridin-1(2H)-yl}methyl)phenyl]acetamide To a mixture of Example 67 (75 mg, 0.222 mmol), triethylamine (0.068 mL, 0.488 mmol), and acetic acid (0.063 mL, 1.108 mmol) in dichloromethane (2 mL) was added N-(4-formylphenyl)acetamide (72.3 mg, 0.443 mmol) and MP-(CN)BH$_3$ resin (Biotage, 2.17 mmol/g, 414 mg, 0.887 mmol). The reaction mixture was shaken on an orbital shaker overnight. The reaction mixture was diluted with ethyl acetate, and the resin was filtered off, rinsing with ethyl acetate and dichloromethane. The solvent was removed in vacuo, and the crude residue was purified via flash chromatography: Analogix Intelliflash™ 280, 12 g silica column, 2% to 10% methanol/dichloromethane gradient over 30 minutes to give the title compound. $^1$H NMR (400 MHz, DMSO-$d_6$) δ 12.19 (s, 1H) 9.97 (s, 1H) 8.77 (s, 1H) 7.55 (d, J=8.24 Hz, 2H) 7.13-7.40 (m, 5H) 6.54 (s, 1H) 6.34 (s, 1H) 4.08 (q, J=6.82 Hz, 2H) 3.56 (s, 2H) 2.96-3.22 (m, 4H) 2.65 (s, 2H) 2.04 (s, 3H) 1.09-1.26 (m, 3H). MS (ESI$^+$) m/z 486.2 (M+H)$^+$.

Example 69 tert-butyl [4-({4-[4-(5-fluoro-2-methoxyphenyl)-7H-pyrrolo[2,3-d]pyrimidin-6-yl]-3,6-dihydropyridin-1(2H)-yl}methyl)phenyl]carbamate The title compound was prepared essentially as described in Example 68, substituting Example 67 with Example 3F and N-(4-formylphenyl)acetamide with tert-butyl(4-formylphenyl)carbamate. $^1$H NMR (400 MHz, DMSO-$d_6$) δ 12.21 (s, 1H) 9.32 (s, 1H) 8.77 (s, 1H) 7.42 (d, J=7.93 Hz, 2H) 7.28-7.38 (m, 2H) 7.17-7.27 (m, 3H) 6.53 (s, 1H) 6.28 (s, 1H) 3.77 (s, 3H) 3.45-3.63 (m, 2H) 2.65 (d, J=13.12 Hz, 2H) 2.45-2.55 (m, 3H) 1.47 (s, 9H). MS (ESI$^+$) m/z 530.1 (M+H)$^+$.

Example 70

4-({4-[4-(5-fluoro-2-methoxyphenyl)-7H-pyrrolo[2,3-d]pyrimidin-6-yl]-3,6-dihydropyridin-1(2H)-yl}methyl)aniline The title compound was prepared as a hydrochloride salt essentially as described in Example 67, substituting Example 66 with Example 69. $^1$H NMR (400 MHz, DMSO-$d_6$) δ 12.18 (s, 1H) 8.76 (s, 1H) 7.28-7.40 (m, 2H) 7.15-7.26 (m, 1H) 6.96 (d, J=7.63 Hz, 2H) 6.52 (d, J=8.24 Hz, 3H) 6.26 (s, 1H) 4.95 (s, 2H) 3.77 (s, 3H) 3.40 (s, 2H) 3.05 (s, 2H) 2.54-2.66 (m, 2H) 2.42-2.48 (m, 2H). MS (ESI$^+$) m/z 430.2 (M+H)$^+$.

Example 71 methyl 4-({4-[4-(5-fluoro-2-methoxyphenyl)-7H-pyrrolo[2,3-d]pyrimidin-6-yl]-3,6-dihydropyridin-1(2H)-yl}methyl)benzoate The title compound was prepared essentially as described in Example 68, substituting Example 67 with Example 3F and N-(4-formylphenyl)acetamide with methyl 4-formylbenzoate. $^1$H NMR (400 MHz, DMSO-$d_6$) δ 12.21 (s, 1H) 8.77 (s, 1H) 7.94 (d, J=8.24 Hz, 2H) 7.50 (d, J=8.24 Hz, 2H) 7.29-7.38 (m, 2H) 7.16-7.27 (m, 1H) 6.54 (s, 1H) 6.28 (s, 1H) 3.85 (s, 3H) 3.78 (s, 3H) 3.68 (s, 2H) 3.14 (d, J=1.83 Hz, 2H) 2.65 (t, J=5.49 Hz, 2H) 2.41-2.56 (m, 2H). MS (ESI$^+$) m/z 473.2 (M+H)$^+$.

Example 72

4-({4-[4-(5-fluoro-2-methoxyphenyl)-7H-pyrrolo[2,3-d]pyrimidin-6-yl]-3,6-dihydropyridin-1(2H)-yl}methyl)benzoic acid To a solution of Example 71 (60 mg, 0.127 mmol) in 5 mL dioxane was added 6 M sodium hydroxide (212 µL, 1.270 mmol). The reaction mixture was held at 50° C. for 12 hours and then diluted with 25 mL water. The aqueous mixture was extracted with ethyl acetate (2×), and the organic fractions were discarded. The aqueous layer was diluted with an equal amount of ethyl acetate and made slightly acidic with 2.5 M hydrochloric acid. The aqueous layer was extracted with ethyl acetate (2×), and the combined organic fractions were washed with brine, dried over magnesium sulfate and concentrated to give the title compound. $^1$H NMR (400 MHz, DMSO-$d_6$) δ 12.20 (s, 1H) 8.76 (s, 1H) 7.92 (d, J=7.93 Hz, 2H) 7.47 (d, J=8.24 Hz, 2H) 7.28-7.39 (m, 2H) 7.15-7.27 (m, 1H) 6.54 (s, 1H) 6.28 (d, J=1.53 Hz, 1H) 3.78 (s, 3H) 3.68 (s, 2H) 3.14 (s, 2H) 2.65 (t, J=5.49 Hz, 2H) 2.50 (s, 3H). MS (ESI$^+$) m/z 459.1 (M+H)$^+$.

Example 73 methyl trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylate To a solution of Example 3F (200 mg, 0.503 mmol) in 5 mL N,N-dimethylformamide was added (trans)-4-(methoxycarbonyl)cyclohexanecarboxylic acid (141 mg, 0.755 mmol), $N^1$-((ethylimino)methylene)-$N^3$,$N^3$-dimethylpropane-1,3-diamine hydrochloride (125 mg, 0.654 mmol), 1H-benzo[d][1,2,3]triazol-1-ol hydrate (116 mg, 0.755 mmol) and N-ethyl-N-isopropylpropan-2-amine (0.440 mL, 2.52 mmol). The reaction mixture was stirred at room temperature overnight and then extracted with ethyl acetate. The combined organic fractions were washed with saturated sodium bicarbonate, water, and brine, dried over magnesium sulfate and concentrated. The crude material was purified by flash chromatography: Analogix Intelliflash™ 280, 12 g silica column, 10% to 60% ethyl acetate/hexane gradient over 30 minutes to give the title compound. $^1$H NMR (400 MHz, DMSO-$d_6$) δ 12.29 (d, J=10.99 Hz, 1H) 8.78 (s, 1H) 7.30-7.39 (m, 2H) 7.18-7.27 (m, 1H) 6.58 (s, 1H) 6.35 (s, 1H) 4.30 (s, 1H) 4.16 (s, 1H) 3.79 (s, 3H) 3.63-3.75 (m, 2H) 3.53-3.63 (m, 3H) 2.53-2.77 (m, 2H) 2.22-2.48 (m, 2H) 1.85-2.01 (m, 2H) 1.72 (s, 2H) 1.31-1.54 (m, 4H). MS (ESI$^+$) m/z 459.1 (M+H)$^+$.

Example 74 trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylic acid The title compound was prepared essentially as described in Example 72, substituting Example 71 with Example 73. $^1$H NMR (400 MHz, DMSO-$d_6$) δ 12.67 (s, 1H) 8.89 (s, 1H) 7.41 (dd, J=7.93, 4.58 Hz, 2H) 7.20-7.34 (m, 1H) 6.63 (s, 1H) 6.49 (s, 1H) 4.31 (s, 1H) 4.17 (s, 1H) 3.75-3.86 (m, 3H) 3.63-3.75 (m, 2H) 2.55-2.74 (m, 2H) 2.47 (s, 2H) 2.18 (s, 1H) 1.91 (s, 2H) 1.64-1.79 (m, 2H) 1.28-1.53 (m, 4H). MS (ESI$^+$) m/z 479.2 (M+H)$^+$.

Example 75

4-[4-(5-fluoro-2-methoxyphenyl)-7H-pyrrolo[2,3-d]pyrimidin-6-yl]-N,N-dimethyl-3,6-dihydropyridine-1(2H)-carboxamide

Example 75A tert-butyl 4-(4-chloro-7-(phenylsulfonyl)-7H-pyrrolo [2,3-d]pyrimidin-6-yl)-5,6-dihydropyridine-1(2H)-carboxylate The title compound was prepared essentially as described in Example 3D, substituting Example 3C with 4-chloro-6-iodo-7-(phenylsulfonyl)-7H-pyrrolo[2,3-d]pyrimidine. MS (ESI$^+$) m/z 475.0 (M+H)$^+$.

Example 75B 4-chloro-7-(phenylsulfonyl)-6-(1,2,3,6-tetrahydropyridin-4-yl)-7H-pyrrolo[2,3-d]pyrimidine The title compound was prepared as a hydrochloride salt essentially as described in Example 3F, substituting Example 3E with Example 75A. LC-MS (ESI$^+$) m/z 375.1 (M+H)$^+$.

Example 75C 4-(4-chloro-7-(phenylsulfonyl)-7H-pyrrolo[2,3-d] pyrimidin-6-yl)-N,N-dimethyl-5,6-dihydropyridine-1(2H)-carboxamide To a solution of Example 75B (4.25 g, 10.33 mmol) and diisopropylethylamine (5.41 ml, 31.0 mmol) in 120 mL dichloromethane was added dimethylcarbamic chloride (1.333 g, 12.40 mmol). The mixture was stirred at 15° C. for 5 hours. The reaction was concentrated in vacuo, and the crude material was purified via flash chromatography: Analogix Intelliflash™ 280, 80 g silica column, 1:1 hexane/ethyl acetate to give the title compound. LC-MS (ESI$^+$) m/z 446.0 (M+H)$^+$.

Example 75D 4-(4-chloro-7H-pyrrolo[2,3-d]pyrimidin-6-yl)-N,N-dimethyl-5,6-dihydropyridine-1(2H)-carboxamide The title compound was prepared essentially as described in Example 3E, substituting Example 3D with Example 75C. LC-MS (ESI$^+$) m/z 306.0 (M+H)$^+$.

Example 75E

4-[4-(5-fluoro-2-methoxyphenyl)-7H-pyrrolo[2,3-d] pyrimidin-6-yl]-N,N-dimethyl-3,6-dihydropyridine-1(2H)-carboxamide The title compound was prepared essentially as described in Example 3B, substituting Example 3A with Example 75D. $^1$H NMR (500 MHz, DMSO-d$_6$) δ 12.25 (s, 1H) 8.78 (s, 1H) 7.29-7.39 (m, 2H) 7.19-7.26 (m, 1H) 6.56 (s, 1H) 3.90 (d, J=2.44 Hz, 2H) 3.79 (s, 3H) 3.28-3.38 (m, 2H) 2.69-2.82 (m, 6H) 2.53 (s, 2H). MS (ESI$^+$) m/z 396.2 (M+H)$^+$.

Example 76

4-[4-(2,3-difluorophenyl)-7H-pyrrolo[2,3-d]pyrimidin-6-yl]-N,N-dimethyl-3,6-dihydropyridine-1(2H)-carboxamide The title compound was prepared essentially as described in Example 3B, substituting Example 3A with Example 75D and (5-fluoro-2-methoxyphenyl)boronic acid with 2,3 difluorophenyl boronic acid. $^1$H NMR (500 MHz, DMSO-d$_6$) δ 12.46 (s, 1H) 8.85 (s, 1H) 7.52-7.73 (m, 2H) 7.29-7.49 (m, 1H) 6.61 (s, 1H) 6.53 (d, J=1.22 Hz, 1H) 3.90 (d, J=2.44 Hz, 2H) 3.34-3.38 (m, 2H) 2.71-2.83 (m, 6H) 2.56 (s, 1H). MS (ESI$^+$) m/z 384.2 (M+H)$^+$.

Example 77

(2S)-cyclohexyl({4-[4-(5-fluoro-2-methoxyphenyl)-7H-pyrrolo[2,3-d]pyrimidin-6-yl]cyclohex-3-en-1-yl}amino)acetic acid The title compound was prepared as a hydrochloride salt essentially as described in Example 83C substituting (S)-tert-butyl 2-amino-3,3-dimethylbutanoate hydrochloric acid with (S)-tert-butyl 2-amino-2-cyclohexylacetate hydrochloride. $^1$H NMR (500 MHz, DMSO-d$_6$) δ 13.12 (s, 1H) 8.82-9.67 (m, 3H) 8.34 (s, 2H) 7.42-7.58 (m, 1H) 7.22-7.42 (m, 1H) 6.63 (d, J=22.58 Hz, 2H) 4.00 (s, 2H) 3.78-3.87 (m, 3H) 2.56-2.85 (m, 3H) 2.20-2.40 (m, 1H) 2.04-2.20 (m, 1H) 1.68-1.96 (m, 3H) 1.60 (s, 1H) 0.96-1.41 (m, 5H). MS (ESI$^+$) m/z 479.2 (M+H)$^+$.

Example 78

N-{4-[4-(5-fluoro-2-methoxyphenyl)-7H-pyrrolo[2,3-d]pyrimidin-6-yl]cyclohex-3-en-1-yl}-L-valine The title compound was prepared as a hydrochloride salt essentially as described in Example 83C substituting (S)-tert-butyl 2-amino-3,3-dimethylbutanoate hydrochloric acid with (S)-tert-butyl 2-amino-3-methylbutanoate, hydrochloric acid. $^1$H NMR (400 MHz, DMSO-d$_6$) δ 13.32 (s, 1H) 9.67 (d, J=110.17 Hz, 1H) 8.82-9.24 (m, 2H) 8.41 (s, 2H) 7.43-7.60 (m, 2H) 7.23-7.44 (m, 1H) 6.55-6.83 (m, 2H) 3.97-4.18 (m, 1H) 3.77-3.90 (m, 3H) 3.67-3.78 (m, 2H) 2.60-2.90 (m, 3H) 2.12-2.42 (m, 2H) 1.81-2.03 (m, 1H) 0.90-1.17 (m, 6H). MS (ESI$^+$) m/z 439.2 (M+H)$^+$.

Example 79

4-[4-(5-fluoro-2-methoxyphenyl)-7H-pyrrolo[2,3-d] pyrimidin-6-yl]cyclohex-3-ene-1-carboxylic acid To a suspension of Example 61A (300 mg, 0.813 mmol) and ethyl 4-(4,4,5,5-tetramethyl-1,3,2-dioxaborolan-2-yl)cyclohex-3-enecarboxylate (342 mg, 1.219 mmol) in 10 mL dimethoxyethane/ethanol/water (7:2:3) was added sodium carbonate (345 mg, 3.25 mmol) and dichlorobis(triphenylphosphine) palladium(II) (17.09 mg, 0.024 mmol). The reaction was stirred at 90° C. for 12 hours, then cooled, and extracted with ethyl acetate. The combined organic fractions were washed with saturated sodium bicarbonate (2x), water, and brine, dried over magnesium sulfate and concentrated. The crude material was triturated with ethyl acetate, and the solid was collected by filtration. The solid was dissolved in 15 mL dioxane, treated with 6 M sodium hydroxide (1.355 ml, 8.13 mmol) and stirred at 90° C. for 12 hours. Most of the solvent was removed, and the residue was diluted with 30 mL water. The aqueous mixture was extracted with ethyl acetate (2x), and the organic fractions were discarded. The aqueous layer was made neutral (~pH 7) with 1 M HCl. The solid was collected by filtration and dried under high-vacuum to give the title compound. $^1$H NMR (500 MHz, DMSO-d$_6$) δ 12.16 (s, 1H) 8.75 (s, 1H) 7.28-7.39 (m, 2H) 7.15-7.26 (m, 1H) 6.60

(s, 1H) 6.24 (s, 1H) 3.69-3.85 (m, 3H) 2.26-2.47 (m, 4H) 1.93-2.10 (m, 1H) 1.54-1.77 (m, 1H) MS (ESI$^+$) m/z 368.2 (M+H)$^+$.

Example 80

2-{4-[4-(5-fluoro-2-methoxyphenyl)-7H-pyrrolo[2,3-d]pyrimidin-6-yl]-3,6-dihydropyridin-1(2H)-yl}-N,N-dimethylacetamide To a suspension Example 3F (150 mg, 0.416 mmol) in 4 mL N,N-dimethylformamide was added N-ethyl-N-isopropylpropan-2-amine (0.363 mL, 2.079 mmol) followed by 2-chloro-N,N-dimethylacetamide (0.051 mL, 0.499 mmol). The reaction mixture was stirred at room temperature overnight and then diluted with ethyl acetate. The mixture was washed with saturated sodium bicarbonate, water, and brine, dried over magnesium sulfate and concentrated. The crude material was triturated with ethyl acetate, and the solid was collected by filtration and dried under high vacuum to give the title compound. $^1$H NMR (400 MHz, DMSO-d$_6$) δ 12.21 (s, 1H) 8.77 (s, 1H) 7.29-7.39 (m, 2H) 7.16-7.27 (m, 1H) 6.54 (s, 1H) 6.29 (d, J=1.53 Hz, 1H) 3.78 (s, 3H) 3.26 (s, 2H) 2.97-3.06 (m, 3H) 2.80-2.87 (m, 3H) 2.68-2.79 (m, 2H) 2.50 (d, J=1.53 Hz, 2H). MS (ESI$^+$) m/z 410.1 (M+H)$^+$.

Example 81

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]methanesulfonamide The title compound was prepared essentially as described in Example 68, substituting Example 67 with Example 3F and N-(4-formylphenyl)acetamide with N-(4-formylphenyl)methanesulfonamide. $^1$H NMR (500 MHz, DMSO-d$_6$) δ 12.21 (s, 1H) 9.70 (s, 1H) 8.77 (s, 1H) 7.27-7.38 (m, 4H) 7.15-7.25 (m, 3H) 6.54 (s, 1H) 6.28 (d, J=1.53 Hz, 1H) 3.78 (s, 3H) 3.56 (s, 2H) 3.12 (s, 2H) 2.98 (s, 3H) 2.64 (s, 2H) 2.44-2.53 (m, 2H). MS (ESI$^+$) m/z 508.1 (M+H)$^+$.

Example 82 ethyl ({4-[4-(5-fluoro-2-methoxyphenyl)-7H-pyrrolo[2,3-d]pyrimidin-6-yl]-3,6-dihydropyridin-1(2H)-yl}sulfonyl)carbamate A solution of Example 3F (104 mg, 0.381 mmol), ((4-(dimethylamino)pyridin-1-ium-1-yl)sulfonyl)(ethoxycarbonyl)amide (104 mg, 0.381 mmol) and triethylamine (0.121 mL, 0.866 mmol) in 5 mL N,N-dimethylformamide was stirred at room temperature overnight. The reaction was purified via flash chromatography: Analogix Intelliflash™ 280, 24 g silica column, 0% to 8% methanol/dichloromethane gradient over 30 minutes gave the title compound. $^1$H NMR (500 MHz, DMSO-d$_6$) δ 12.29 (s, 1H) 11.39 (s, 1H) 8.62-8.89 (m, 1H) 7.30-7.38 (m, 2H) 7.18-7.28 (m, 1H) 6.56 (s, 1H) 6.35 (d, J=1.83 Hz, 1H) 3.97-4.13 (m, 4H) 3.70-3.84 (m, 3H) 3.48 (t, J=5.80 Hz, 2H) 2.60 (s, 2H) 1.08-1.23 (m, 3H). MS (ESI$^+$) m/z 476.1 (M+H)$^+$.

Example 83

N-{4-[4-(5-fluoro-2-methoxyphenyl)-7H-pyrrolo[2,3-d]pyrimidin-6-yl]cyclohex-3-en-1-yl}-3-methyl-L-valine Example 83A 4-(5-fluoro-2-methoxyphenyl)-6-(1,4-dioxaspiro[4.5]dec-7-en-8-yl)-7H-pyrrolo[2,3-d]pyrimidine The title compound was prepared essentially as described in Example 61B, substituting 2-(4,4-difluorocyclohex-1-en-1-yl)-4,4,5,5-tetramethyl-1,3,2-dioxaborolane with 4,4,5,5-tetramethyl-2-(1,4-dioxaspiro[4.5]dec-7-en-8-yl)-1,3,2-dioxaborolane. MS (ESI$^+$) m/z 382.2 (M+H)$^+$.

Example 83B 4-(4-(5-fluoro-2-methoxyphenyl)-7H-pyrrolo[2,3-d]pyrimidin-6-yl)cyclohex-3-enone To a suspension of Example 83A (370 mg, 0.970 mmol) in 15 mL dichloromethane was added excess trifluoroacetic acid. The reaction was held at room temperature overnight. The volatiles were removed in vacuo, and the residue was dissolved in 30 mL ethyl acetate. The mixture was washed with saturated sodium bicarbonate and brine, dried over magnesium sulfate, and concentrated to give the title compound. MS (ESI$^+$) m/z 338.2 (M+H)$^+$.

Example 83C

N-{4-[4-(5-fluoro-2-methoxyphenyl)-7H-pyrrolo[2,3-d]pyrimidin-6-yl]cyclohex-3-en-1-yl}-3-methyl-L-valine To a mixture of Example 83B (100 mg, 0.296 mmol), triethylamine (0.091 mL, 0.652 mmol), and acetic acid (0.085 mL, 1.482 mmol) in dichloromethane (3 mL) was added (S)-tert-butyl 2-amino-3,3-dimethylbutanoate hydrochloride (133 mg, 0.593 mmol) and MP-(CN)BH$_3$ resin (Biotage, 2.17 mmol/g, 546 mg, 1.186 mmol). The reaction mixture was shaken on an orbital shaker overnight. The reaction mixture was diluted with 5 mL dichloromethane and the resin filtered off, rinsing with dichloromethane and methanol. The crude material was purified via column chromatography: Analogix Intelliflash™ 280, 12 g silica cartridge, 0-4% methanol/dichloromethane gradient over 30 minutes. The material was dissolved in 5 mL dichloromethane and treated with excess trifluoroacetic acid and stirred at room temperature overnight. The volatiles were removed in vacuo, the residue was dissolved in 5 mL methanol, and the mixture was treated with excess 2 M HCl/diethyl ether. The solution was stirred at room temperature for 20 minutes and then diluted with diethyl ether. The resultant solid was collected by filtration and dried under high vacuum to give the title compound as a hydrochloride salt. $^1$H NMR (400 MHz, DMSO-d$_6$) δ 13.34 (s, 1H) 8.80-9.10 (m, 3H) 8.36 (s, 1H) 7.46-7.57 (m, 2H) 7.27-7.39 (m, 1H) 6.60-6.78 (m, 2H) 4.02 (d, J=10.07 Hz, 1H) 3.76-3.88 (m, 3H) 3.51-3.61 (m, 1H) 3.15-3.36 (m, 2H) 2.57-2.93 (m, 2H) 2.34 (s, 1H) 1.99-2.16 (m, 1H) 1.78-1.98 (m, 1H) 1.15 (s, 9H). MS (ESI$^+$) m/z 453.2 (M+H)$^+$.

Example 84

N-{4-[4-(5-fluoro-2-methoxyphenyl)-7H-pyrrolo[2,3-d]pyrimidin-6-yl]cyclohex-3-en-1-yl}-D-valine The title compound was prepared as a hydrochloride salt essentially as described in Example 83C substituting (S)-tert-butyl 2-amino-3,3-dimethylbutanoate hydrochloride with (R)-tert-butyl 2-amino-3-methylbutanoate hydrochloride. $^1$H NMR (500 MHz, DMSO-$d_6$) δ 13.33 (s, 1H) 8.81-9.24 (m, 1H) 8.43 (s, 2H) 7.51 (t, J=7.78 Hz, 2H) 7.25-7.42 (m, 1H) 6.51-6.83 (m, 2H) 4.04 (s, 1H) 3.80-3.89 (m, 3H) 3.66-3.77 (m, 2H) 3.25-3.44 (m, 1H) 2.94-3.12 (m, 1H) 2.61-2.89 (m, 2H) 2.29 (s, 1H) 2.13-2.26 (m, 1H) 1.84-2.02 (m, 1H) 0.93-1.05 (m, 6H). MS (ESI$^+$) m/z 439.2 (M+H)$^+$.

Example 85

N-{4-[4-(5-fluoro-2-methoxyphenyl)-7H-pyrrolo[2,3-d]pyrimidin-6-yl]cyclohex-3-en-1-yl}-L-leucine The title compound was prepared as a hydrochloride salt essentially as described in Example 83C substituting (S)-tert-butyl 2-amino-3,3-dimethylbutanoate hydrochloride with (S)-tert-butyl 2-amino-4-methylpentanoate hydrochloride. $^1$H NMR (500 MHz, DMSO-$d_6$) δ 13.37 (s, 1H) 9.18-10.28 (m, 2H) 8.92-9.19 (m, 1H) 7.44-7.63 (m, 2H) 7.23-7.43 (m, 1H) 6.51-6.81 (m, 2H) 4.00 (s, 2H) 3.72-3.96 (m, 3H) 3.27-3.45 (m, 1H) 2.56-2.90 (m, 1H) 2.16-2.38 (m, 1H) 1.70-2.04 (m, 4H) 0.79-1.04 (m, 6H). MS (ESI$^+$) m/z 453.2 (M+H)$^+$.

Example 86

4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid

Example 86A ethyl 4-{4-[4-(5-fluoro-2-methoxyphenyl)-7H-pyrrolo[2,3-d]pyrimidin-6-yl]-3,6-dihydropyridin-1(2H)-yl}cyclohexanecarboxylate The title compound was prepared essentially as described in Example 68, substituting Example 67 with Example 3F and N-(4-formylphenyl)acetamide with ethyl 4-oxocyclohexanecarboxylate. MS (ESI$^+$) m/z 479.2 (M+H)$^+$.

Example 86B

4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid To a solution of Example 86A (266 mg, 0.556 mmol) in 4 mL of tetrahydrofuran/water (3:1) was added lithium hydroxide mono hydrate (46.7 mg, 1.112 mmol). The reaction was stirred at room temperature overnight. The volatiles were then removed, and the residue dissolved in 5 mL water and the pH was adjusted to pH ~6-7 with 1 M hydrochloric acid. The solid was collected by filtration and dried under high vacuum overnight to give the title compound as a hydrochloride salt. $^1$H NMR (400 MHz, DMSO-$d_6$) δ 12.26 (s, 1H) 8.81 (s, 1H) 7.13-7.52 (m, 3H) 6.62 (s, 1H) 6.32 (s, 1H) 3.83 (s, 3H) 3.32 (d, J=21.06 Hz, 2H) 2.67-2.86 (m, 2H) 2.56 (s, 1H) 2.41 (s, 1H) 2.10-2.27 (m, 1H) 1.83-2.08 (m, 3H) 1.24-1.76 (m, 6H). MS (ESI$^+$) m/z 451.1 (M+H)$^+$.

Example 87

(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid

Example 87A methyl(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetate The title compound was prepared essentially as described in Example 68, substituting Example 67 with Example 3F and N-(4-formylphenyl)acetamide with methyl 2-(4-oxocyclohexyl)acetate. The crude material was purified by flash chromatography: Analogix 280, 40 g silica cartridge, 10-70% (3:1 ethyl acetate: ethanol) in heptanes gradient over 30 minutes to give the title compound. MS (ESI$^+$) m/z 479.2 (M+H)$^+$.

Example 87B (trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid The title compound was prepared essentially as described in Example 86B, substituting Example 86A with Example 87A. The crude material was purified by HPLC essentially as described in Example 41B to give the title compound as a trifluoroacetate salt. $^1$H NMR (400 MHz, DMSO-$d_6$) δ 13.05 (s, 1H) 10.01 (s, 1H) 9.00 (s, 1H) 7.40-7.51 (m, 2H) 7.27-7.36 (m, 1H) 6.72 (s, 1H) 6.65 (s, 1H) 3.95-4.09 (m, 2H) 3.82 (s, 3H) 3.72 (d, J=8.85 Hz, 1H) 3.18-3.34 (m, 2H) 2.78-2.98 (m, 2H) 2.02-2.22 (m, 4H) 1.88 (d, J=12.21 Hz, 2H) 1.40-1.76 (m, 3H) 1.08 (q, J=12.21 Hz, 2H). MS (ESI$^+$) m/z 465.2 (M+H)$^+$.

CDK9 Enzyme Protocol

CDK9 enzyme activities were measured using LANCE ULight TR-FRET kinase assay reagents (PerkinElmer, Waltham, Mass.). Compounds were directly added in 100% DMSO to white low volume assay plates (Perkin Elmer Proxiplate 6008289) using a Labcyte Echo acoustic dispenser. Assay reagents in serine/threonine kinase assay buffer containing 20 mM HEPES, 10 mM MgCl$_2$, 100 mM Na$_3$VO$_4$, and 0.0075% Triton X-100. were added for final reaction mixture concentrations of 1000 µM ATP, 100 nM U-light MBP peptide (Perkin Elmer TRF0109M) and reaction initiated with 4 nM CDK9/Cyclin T1 (Carna Biosciences 04-110). The kinase reaction was carried out for 30 minutes before addition of stopping buffer to a final of 20 mM EDTA and 0.5 nM of LANCE Ultra Europium anti-phospho-MBP antibody (PerkinElmer TRF0201M) in LANCE detection buffer (PerkinElmer CR97-100). The reaction was equilibrated for 1 hour and the signal read in the Perkin Elmer Envision in TR-FRET mode (excitation at 320 nm and emission at 615/665 nm).

Cell Viability Protocol

Cell viability assays were performed using A431 or H929 cells. A431 cells were seeded in 96-well plates at 10,000 cells/well, and after overnight incubation, treated with compounds at 2-times the final concentration to result in a dose response of 3-fold dilutions from 10 µM to 0.0005 µM (50 µL/well, 0.1% final DMSO concentration). H929 cells were seeded in 96-well plates at 10,000 cells/well and treated immediately with compounds as described above. After 24 hours at 37° C., cell viability was measured using Cell Titer-Glo reagent (Promega) with a luminescence reader. Alternately, cell viability assays were performed in 384-well format. A431 cells were seeded in 384-well plates at 2500 cells/well and, after overnight incubation, treated with compounds in a dose response of 3-fold dilutions from 10 μM to 0.0005 μM (25 nL/well, 0.1% final DMSO concentration). For the H929 viability assay, 25 nL/well of the compounds was dispensed into 384-well plates in a dose response as described above and cells were immediately seeded in 384-well plates at 2500 cells/well. After 24 hours at 37° C., cell viability was measured using Cell TiterGlo reagent (Promega) with a luminescence reader. The results are reported in Table 1.

TABLE 1

| Example | CDK9 IC$_{50}$ (μM) | A431 viability EC$_{50}$ (μM) | H929 viability EC$_{50}$ (μM) |
|---|---|---|---|
| 1 | 0.052 | 0.1 | ND |
| 2 | 0.11 | ND | ND |
| 3 | 0.013 | 0.032 | 0.2 |
| 4 | 0.023 | ND | 0.35 |
| 5 | 0.02 | ND | 0.38 |
| 6 | 0.042 | ND | 0.41 |
| 7 | 0.037 | 0.15 | 0.18 |
| 8 | 0.019 | ND | 0.69 |
| 9 | 0.072 | 0.12 | ND |
| 10 | 0.16 | ND | 0.55 |
| 11 | 0.043 | ND | 0.31 |
| 12 | 0.088 | ND | 0.93 |
| 13 | 0.069 | ND | 0.84 |
| 14 | 0.065 | ND | 1.7 |
| 15 | 0.086 | ND | 0.21 |
| 16 | 0.15 | ND | 1.1 |
| 17 | 0.12 | 0.26 | 0.2 |
| 18 | 0.13 | ND | 0.4 |
| 19 | 0.088 | ND | 0.18 |
| 20 | 0.13 | ND | 0.38 |
| 21 | 0.035 | ND | 0.44 |
| 22 | 0.24 | ND | 1.1 |
| 23 | 0.27 | ND | 0.42 |
| 24 | 0.1 | ND | 0.25 |
| 25 | 0.076 | ND | 0.058 |
| 26 | 0.19 | ND | 0.61 |
| 27 | 0.22 | ND | 0.72 |
| 28 | 0.22 | ND | 1 |
| 29 | 0.13 | ND | 0.29 |
| 30 | 0.13 | ND | 0.23 |
| 31 | 0.11 | ND | 0.16 |
| 32 | 0.26 | ND | 3.6 |
| 33 | 0.3 | ND | ND |
| 34 | 0.17 | ND | 0.63 |
| 35 | 0.15 | ND | 0.93 |
| 36 | 0.17 | ND | 1 |
| 37 | 0.051 | ND | 0.329 |
| 38 | 0.043 | ND | 0.376 |
| 39 | 0.21 | ND | 4.74 |
| 40 | 0.15 | ND | 0.669 |
| 41 | 11.7 | ND | ND |
| 42 | 1.2 | ND | ND |
| 43 | >12.5 | ND | ND |
| 44 | 0.61 | ND | ND |
| 45 | 0.18 | ND | >10 |
| 46 | 0.83 | ND | ND |
| 47 | 1.4 | ND | ND |
| 48 | 0.29 | ND | ND |
| 49 | 1.3 | ND | ND |
| 50 | 1.0 | ND | ND |
| 51 | >12.5 | ND | ND |
| 52 | 10.1 | ND | ND |
| 53 | 2.8 | ND | ND |
| 54 | 4.1 | ND | ND |
| 55 | 1.9 | ND | ND |
| 56 | 1.6 | ND | ND |
| 57 | 2.4 | ND | ND |
| 58 | >12.5 | ND | ND |
| 59 | 0.91 | ND | ND |
| 60 | 4 | ND | ND |
| 61 | 0.062 | ND | 1.4 |
| 62 | 5 | ND | ND |
| 63 | 1.3 | ND | ND |
| 64 | 2 | ND | ND |
| 65 | 0.069 | ND | 1 |
| 66 | 1.5 | ND | ND |
| 67 | 0.3 | ND | ND |
| 68 | 0.20 | ND | 0.42 |
| 69 | 0.45 | ND | ND |
| 70 | 0.091 | ND | 0.16 |
| 71 | 0.11 | ND | 0.78 |
| 72 | 0.11 | 5.2 | 2.4 |
| 73 | 0.070 | ND | 0.15 |
| 74 | 0.11 | ND | 5.9 |
| 75 | 0.016 | ND | 0.60 |
| 76 | 0.068 | ND | 3.5 |
| 77 | 0.29 | ND | 0.60 |
| 78 | 0.75 | ND | 6.8 |
| 79 | 0.29 | ND | 6.7 |
| 80 | 0.11 | 0.13 | 0.12 |
| 81 | 0.075 | 0.11 | 0.10 |
| 82 | 0.071 | ND | 0.78 |
| 83 | 0.32 | ND | 0.52 |
| 84 | 0.44 | ND | 6.4 |
| 85 | 0.17 | ND | 1.7 |
| 86 | 0.40 | ND | 3.6 |
| 87 | 0.30 | ND | 4.1 |

ND = not determined

It is understood that the examples and embodiments described herein are for illustrative purposes only and that various modifications or changes in light thereof will be suggested to persons skilled in the art and are to be included within the spirit and purview of the appended claims. All publications, patents, and patent applications cited herein are hereby incorporated by reference in their entirety for all purposes.

What is claimed is:

1. A compound having Formula (Ia), or a pharmaceutically acceptable salt thereof,

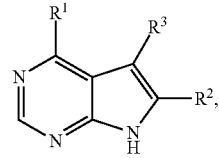

(Ia)

wherein $R^1$ is selected from the group consisting of phenyl, 5 to 6 membered heteroaryl, 4 to 7 membered heterocycloalkyl and 4 to 7 membered heterocycloalkenyl; wherein the $R^1$ phenyl, 5 to 6 membered heteroaryl, 4 to 7 membered heterocycloalkyl and 4 to 7 membered heterocycloalkenyl are optionally substituted with one or more substituents selected from the group consisting of $R^{1A}$, $OR^{1A}$, $NHSO_2R^{1A}$, halo, CN, and $NHR^{1A}$;

$R^{1A}$, at each occurance, is independently selected from the group consisting of $C_1$-$C_3$-haloalkyl, O—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with one to three substituents independently selected from the group consisting of CN, $C_1$-$C_3$ alkyl, halo, OH, $OR^{14}$, $NH_2$, $NHR^{15}$, $NR^{15}R^{16}$, $C(O)NH_2$, $C(O)NHR^{15}$, $C(O)NR^{15}R^{16}$, $SO_2NH_2$, $SO_2NHR^{15}$, $SO_2NR^{15}R^{16}$, $C(O)OH$, and $C(O)OR^{17}$;

$R^2$ is selected from the group consisting of cycloalkyl, cycloalkenyl, heterocycloalkyl and heterocycloalkenyl; wherein the $R^2$ cycloalkyl, cycloalkenyl, heterocycloalkyl and heterocycloalkenyl are optionally substituted with one or more $R^{2A}$;

$R^{2A}$, at each occurance, is independently selected from the group consisting of halo, $NHR^5$, $SO_2R^7$, $SO_2NH_2$, $SO_2NHR^5$, $SO_2NR^5R^6$, $SO_2NHC(O)OR^8$, $C(O)R^8$, $C(O)OR^8$, $C(O)OH$, $C(O)NH_2$, $C(O)NHR^5$, $C(O)NR^5R^6$, $C_1$-$C_5$ alkyl, $C_2$-$C_5$ alkenyl, aryl, 5 to 6 membered heteroaryl, 4 to 7 membered heterocycloalkyl, 4 to 7 membered heterocycloalkenyl, and $C_3$-$C_7$ cycloalkyl; wherein the $R^{2A}$ $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one, two, or three substituents independently selected from the group consisting of $R^4$, $OR^{10}$, $SO_2R^9$, $C(O)R^{10}$, $C(O)OR^{10}$, $NH_2$, $NHR^{11}$, $NR^{11}R^{12}$, $NHC(O)R^{10}$, $NR^{11}C(O)R^{10}$, $NHS(O)_2R^9$, $NR^{11}S(O)_2R^9$, $NHC(O)NH_2$, $NHC(O)NHR^{11}$, $NHC(O)NR^{11}R^{12}$, $NR^{11}C(O)NHR^{12}$, $NR^{11}C(O)NR^{11}R^{13}$, $C(O)NH_2$, $C(O)NHR^{11}$, $C(O)NR^{11}R^{12}$, $SO_2NH_2$, $SO_2NHR^{11}$, $SO_2NR^{11}R^{12}$, $C(O)OH$, OH, CN, and halo;

$R^3$ is selected from the group consisting of hydrogen, $C_1$-$C_4$ alkyl, $NO_2$, CN, F, Cl, Br and I;

$R^4$, at each occurance, is independently selected from the group consisting of $C_1$-$C_5$ alkyl, $C_2$-$C_5$ alkenyl, aryl, 5 to 6 membered heteroaryl, 4 to 7 membered heterocycloalkyl, and $C_3$-$C_7$ cycloalkyl; wherein the $R^4$ $C_1$-$C_5$ alkyl and $C_2$-$C_5$ alkenyl are optionally substituted with one or more substituents selected from the group consisting of halo, $C_1$-$C_3$-haloalkyl, $C(O)OH$, CN, and $NH_2$; wherein the $R^4$ aryl, 5 to 6 membered heteroaryl, 4 to 7 membered heterocycloalkyl, and $C_3$-$C_7$ cycloalkyl are optionally substituted with one or more substituents selected from the group consisting of halo, $C_1$-$C_3$-haloalkyl, $C(O)OH$, CN, $NH_2$, $NHSO_2R^{17}$, $NHC(O)R^{17}$, $C(O)R^{17}$, $C(O)OR^{17}$, and $NHC(O)OR^{17}$;

$R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$, at each occurance, are independently selected from the group consisting of $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl; wherein the $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ $C_1$-$C_6$ alkyl, $C_1$-$C_3$-haloalkyl, $C_2$-$C_5$ alkenyl, aryl, 5 to 6 membered heteroaryl, 4 to 7 membered heterocycloalkyl, and $C_3$-$C_7$ cycloalkyl are optionally substituted with one or more substituents selected from the group consisting of $C_1$-$C_6$ alkyl, $C_3$-$C_7$ cycloalkyl, (O), OH, $C(O)OR^{18}$, $OR^{18}$, and $C(O)OH$; and $R^{18}$, at each occurance, is $C_1$-$C_6$ alkyl.

2. The compound of claim 1, or a pharmaceutically acceptable salt thereof, wherein $R^3$ is hydrogen.

3. The compound of claim 2, or a pharmaceutically acceptable salt thereof, wherein $R^1$ is phenyl; wherein the $R^1$ phenyl is optionally substituted with one or more substituents selected from the group consisting of $R^{1A}$, $OR^{1A}$, $NHSO_2R^{1A}$, halo, and $NHR^{1A}$.

4. The compound of claim 3, or a pharmaceutically acceptable salt thereof, wherein $R^{1A}$, at each occurance, is independently selected from the group consisting of $C_1$-$C_3$-haloalkyl, $O$—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with CN.

5. The compound of claim 2, or a pharmaceutically acceptable salt thereof, wherein $R^1$ is 5 to 6 membered heteroaryl; wherein the $R^1$ 5 to 6 membered heteroaryl is optionally substituted with one or more substituents selected from the group consisting of $R^{1A}$, $OR^{1A}$, $NHSO_2R^{1A}$, halo, and $NHR^{1A}$.

6. The compound of claim 5, or a pharmaceutically acceptable salt thereof, wherein $R^{1A}$, at each occurance, is independently selected from the group consisting of $C_1$-$C_3$-haloalkyl, $O$—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with CN.

7. The compound of claim 2, or a pharmaceutically acceptable salt thereof, wherein $R^1$ is 4 to 7 membered heterocycloalkyl; wherein the $R^1$ 4 to 7 membered heterocycloalkyl is optionally substituted with one or more substituents selected from the group consisting of $R^{1A}$, $OR^{1A}$, $NHSO_2R^{1A}$, halo, and $NHR^{1A}$.

8. The compound of claim 7, or a pharmaceutically acceptable salt thereof, wherein $R^{1A}$, at each occurance, is independently selected from the group consisting of $C_1$-$C_3$-haloalkyl, $O$—$C_1$-$C_3$-haloalkyl, $C_1$-$C_6$-alkyl, $C_1$-$C_3$ alkylene-phenyl, $C_1$-$C_3$ alkylene-(5 to 6 membered heteroaryl), and $C_1$-$C_3$ alkylene-(4 to 7 membered heterocycloalkyl); wherein the $R^{1A}$ phenyl, 5 to 6 membered heteroaryl, and 4 to 7 membered heterocycloalkyl rings are optionally substituted with CN.

9. The compound of claim 2, or a pharmaceutically acceptable salt thereof, wherein $R^2$ is heterocycloalkyl; wherein the $R^2$ heterocycloalkyl is optionally substituted with one or more $R^{2A}$.

10. The compound of claim 9, or a pharmaceutically acceptable salt thereof, wherein $R^{2A}$, at each occurance, is independently selected from the group consisting of halo, $NHR^5$, $SO_2R^7$, $SO_2NHC(O)OR^8$, $C(O)R^8$, $C(O)OR^8$, $C(O)OH$, $C(O)NHR^5$, $C(O)NR^5R^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and OH.

11. The compound of claim 2, or a pharmaceutically acceptable salt thereof, wherein $R^2$ is heterocycloalkenyl; wherein the $R^2$ heterocycloalkenyl is optionally substituted with one or more $R^{2A}$.

12. The compound of claim 11, or a pharmaceutically acceptable salt thereof, wherein $R^{2A}$, at each occurance, is independently selected from the group consisting of halo, $NHR^5$, $SO_2R^7$, $SO_2NHC(O)OR^8$, $C(O)R^8$, $C(O)OR^8$, $C(O)OH$, $C(O)NHR^5$, $C(O)NR^5R^6$, $C_1$-$C_5$ alkyl, and $C_3$-$C_7$ cycloalkyl; wherein the $R^{2A}$ $C_1$-$C_5$ alkyl and $C_3$-$C_7$ cycloalkyl are optionally substituted with one, two, or three substituents independently selected from the group consisting of $R^4$, $C(O)NR^{11}R^{12}$, and OH.

13. A pharmaceutical composition comprising an excipient and a therapeutically effective amount of a compound of claim 1 or a pharmaceutically acceptable salt thereof.

14. A method of inhibiting cyclin-dependent kinase 9 activity in a patient, said method comprising administering to the patient a therapeutically effective amount of a compound of claim 1, or a pharmaceutically acceptable salt thereof.

15. The method of claim 14, further comprising administering to the patient a therapeutically effective amount of at least one additional therapeutic agent.

16. A compound selected from the group consisting of:

4-(5-fluoro-2-methoxyphenyl)-6-(piperidin-4-yl)-7H-pyrrolo[2,3-d]pyrimidine;

4-(5-fluoro-2-methoxyphenyl)-6-(1-methylpiperidin-4-yl)-7H-pyrrolo[2,3-d]pyrimidine;

4-(5-fluoro-2-methoxyphenyl)-6-(1,2,3,6-tetrahydropyridin-4-yl)-7H-pyrrolo[2,3-d]pyrimidine;

4-(5-fluoro-2-methoxyphenyl)-6-(1-methyl-1,2,3,6-tetrahydropyridin-4-yl)-7H-pyrrolo[2,3-d]pyrimidine;

4-(5-fluoro-2-methoxyphenyl)-6-[1-(methylsulfonyl)-1,2,3,6-tetrahydropyridin-4-yl]-7H-pyrrolo[2,3-d]pyrimidine;

1-{4-[4-(5-fluoro-2-methoxyphenyl)-7H-pyrrolo[2,3-d]pyrimidin-6-yl]-3,6-dihydropyridin-1(2H)-yl}ethanone;

1-{4-[4-(5-fluoro-2-methoxyphenyl)-7H-pyrrolo[2,3-d]pyrimidin-6-yl]-3,6-dihydropyridin-1(2H)-yl}-2-hydroxyethanone;

6-[1-(cyclopropylsulfonyl)-1,2,3,6-tetrahydropyridin-4-yl]-4-(5-fluoro-2-methoxyphenyl)-7H-pyrrolo[2,3-d]pyrimidine;

N-benzyl-4-fluoro-3-[6-(piperidin-4-yl)-7H-pyrrolo[2,3-d]pyrimidin-4-yl]aniline;

4-(5-fluoro-2-methoxyphenyl)-6-[1-(propan-2-ylsulfonyl)-1,2,3,6-tetrahydropyridin-4-yl]-7H-pyrrolo[2,3-d]pyrimidine;

cyclopropyl {4-[4-(5-fluoro-2-methoxyphenyl)-7H-pyrrolo[2,3-d]pyrimidin-6-yl]-3,6-dihydropyridin-1(2H)-yl}methanone;

azetidin-2-yl{4-[4-(5-fluoro-2-methoxyphenyl)-7H-pyrrolo[2,3-d]pyrimidin-6-yl]-3,6-dihydropyridin-1(2H)-yl}methanone;

4-({4-[4-(5-fluoro-2-methoxyphenyl)-7H-pyrrolo[2,3-d]pyrimidin-6-yl]-3,6-dihydropyridin-1(2H)-yl}carbonyl)azetidin-2-one;

5-({4-[4-(5-fluoro-2-methoxyphenyl)-7H-pyrrolo[2,3-d]pyrimidin-6-yl]-3,6-dihydropyridin-1(2H)-yl}carbonyl)piperidin-2-one;

{4-[4-(5-fluoro-2-methoxyphenyl)-7H-pyrrolo[2,3-d]pyrimidin-6-yl]-3,6-dihydropyridin-1(2H)-yl}(tetrahydro-2H-pyran-3-yl)methanone;

(1-ethylpyrrolidin-3-yl){4-[4-(5-fluoro-2-methoxyphenyl)-7H-pyrrolo[2,3-d]pyrimidin-6-yl]-3,6-dihydropyridin-1(2H)-yl}methanone;

4-[4-(5-fluoro-2-methoxyphenyl)-7H-pyrrolo[2,3-d]pyrimidin-6-yl]-N-methyl-3,6-dihydropyridine-1(2H)-carboxamide;

1-{4-[4-(5-fluoro-2-methoxyphenyl)-7H-pyrrolo[2,3-d]pyrimidin-6-yl]-3,6-dihydropyridin-1(2H)-yl}-2-methoxyethanone;

4-[4-(5-fluoro-2-methoxyphenyl)-7H-pyrrolo[2,3-d]pyrimidin-6-yl]-N-(prop-2-en-1-yl)-3,6-dihydropyridine-1(2H)-carboxamide;

3-{4-[4-(5-fluoro-2-methoxyphenyl)-7H-pyrrolo[2,3-d]pyrimidin-6-yl]-3,6-dihydropyridin-1(2H)-yl}propane-1,2-diol;

6-(1-benzyl-1,2,3,6-tetrahydropyridin-4-yl)-4-(5-fluoro-2-methoxyphenyl)-7H-pyrrolo[2,3-d]pyrimidine;

4-({4-[4-(5-fluoro-2-methoxyphenyl)-7H-pyrrolo[2,3-d]pyrimidin-6-yl]-3,6-dihydropyridin-1(2H)-yl}methyl)benzonitrile;

3-({4-[4-(5-fluoro-2-methoxyphenyl)-7H-pyrrolo[2,3-d]pyrimidin-6-yl]-3,6-dihydropyridin-1(2H)-yl}methyl)benzonitrile;

4-(5-fluoro-2-methoxyphenyl)-6-[1-(tetrahydrofuran-2-ylmethyl)-1,2,3,6-tetrahydropyridin-4-yl]-7H-pyrrolo[2,3-d]pyrimidine;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]acetamide;

4-(5-fluoro-2-methoxyphenyl)-6-[1-(pyridin-2-ylmethyl)-1,2,3,6-tetrahydropyridin-4-yl]-7H-pyrrolo[2,3-d]pyrimidine;

4-(5-fluoro-2-methoxyphenyl)-6-[1-(pyridin-4-ylmethyl)-1,2,3,6-tetrahydropyridin-4-yl]-7H-pyrrolo[2,3-d]pyrimidine;

4-(5-fluoro-2-methoxyphenyl)-6-(1-{[2-(trifluoromethyl)pyridin-4-yl]methyl}-1,2,3,6-tetrahydropyridin-4-yl)-7H-pyrrolo[2,3-d]pyrimidine;

N-benzyl-4-fluoro-3-{6-[1-(methylsulfonyl)-1,2,3,6-tetrahydropyridin-4-yl]-7H-pyrrolo[2,3-d]pyrimidin-4-yl}aniline;

4-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

3-{[(4-fluoro-3-{6-[1-(methylsulfonyl)-1,2,3,6-tetrahydropyridin-4-yl]-7H-pyrrolo[2,3-d]pyrimidin-4-yl}phenyl)amino]methyl}benzonitrile;

4-fluoro-3-{6-[1-(methylsulfonyl)-1,2,3,6-tetrahydropyridin-4-yl]-7H-pyrrolo[2,3-d]pyrimidin-4-yl}-N-(tetrahydrofuran-2-ylmethyl)aniline;

4-fluoro-3-{6-[1-(methylsulfonyl)-1,2,3,6-tetrahydropyridin-4-yl]-7H-pyrrolo[2,3-d]pyrimidin-4-yl}-N-(pyridin-2-ylmethyl)aniline;

4-(5-fluoro-2-methoxyphenyl)-6-[1-(pyridin-3-ylmethyl)-1,2,3,6-tetrahydropyridin-4-yl]-7H-pyrrolo[2,3-d]pyrimidine;

6-[1-(3-fluorobenzyl)-1,2,3,6-tetrahydropyridin-4-yl]-4-(5-fluoro-2-methoxyphenyl)-7H-pyrrolo[2,3-d]pyrimidine;

6-[1-(3,5-difluorobenzyl)-1,2,3,6-tetrahydropyridin-4-yl]-4-(5-fluoro-2-methoxyphenyl)-7H-pyrrolo[2,3-d]pyrimidine;

4-fluoro-3-{6-[1-(methylsulfonyl)-1,2,3,6-tetrahydropyridin-4-yl]-7H-pyrrolo[2,3-d]pyrimidin-4-yl}-N-(pyridin-4-ylmethyl)aniline;

6-{1-[(1,1-dioxidotetrahydrothiophen-3-yl)sulfonyl]-1,2,3,6-tetrahydropyridin-4-yl}-4-(5-fluoro-2-methoxyphenyl)-7H-pyrrolo[2,3-d]pyrimidine;

4-(5-fluoro-2-methoxyphenyl)-6-[1-(piperidin-4-ylmethyl)-1,2,3,6-tetrahydropyridin-4-yl]-7H-pyrrolo[2,3-d]pyrimidine;

4-(5-fluoro-2-methoxyphenyl)-6-{1-[(trifluoromethyl)sulfonyl]-1,2,3,6-tetrahydropyridin-4-yl}-7H-pyrrolo[2,3-d]pyrimidine;

4-(5-chloro-2-fluoro-3-methylphenyl)-6-[1-(methylsulfonyl)-1,2,3,6-tetrahydropyridin-4-yl]-7H-pyrrolo[2,3-d]pyrimidine;

4-(2-butoxy-5-fluorophenyl)-6-[1-(methylsulfonyl)-1,2,3,6-tetrahydropyridin-4-yl]-7H-pyrrolo[2,3-d]pyrimidine;

4-[5-methyl-2-(propan-2-yloxy)phenyl]-6-[1-(methylsulfonyl)-1,2,3,6-tetrahydropyridin-4-yl]-7H-pyrrolo[2,3-d]pyrimidine;

4-(2-methoxy-5-methylphenyl)-6-[1-(methylsulfonyl)-1,2,3,6-tetrahydropyridin-4-yl]-7H-pyrrolo[2,3-d]pyrimidine;

4-(5-chloro-2-methoxyphenyl)-6-[1-(methylsulfonyl)-1,2,3,6-tetrahydropyridin-4-yl]-7H-pyrrolo[2,3-d]pyrimidine;

4-(2,4-difluorophenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethyl)phenyl]-7H-pyrrolo[2,3-d]pyrimidine;

N-(3-{6-[1-(methylsulfonyl)-1,2,3,6-tetrahydropyridin-4-yl]-7H-pyrrolo[2,3-d]pyrimidin-4-yl}phenyl)methanesulfonamide;

4-(5-fluoro-2-propoxyphenyl)-6-[1-(methylsulfonyl)-1,2,3,6-tetrahydropyridin-4-yl]-7H-pyrrolo[2,3-d]pyrimidine;

4-(2-fluoro-5-methylphenyl)-6-[1-(methylsulfonyl)-1,2,3,6-tetrahydropyridin-4-yl]-7H-pyrrolo[2,3-d]pyrimidine;

4-[2-fluoro-5-(trifluoromethyl)phenyl]-6-[1-(methylsulfonyl)-1,2,3,6-tetrahydropyridin-4-yl]-7H-pyrrolo[2,3-d]pyrimidine;

4-[2-fluoro-5-(propan-2-yloxy)phenyl]-6-[1-(methylsulfonyl)-1,2,3,6-tetrahydropyridin-4-yl]-7H-pyrrolo[2,3-d]pyrimidine;

4-(5-methyl-2-propoxyphenyl)-6-[1-(methylsulfonyl)-1,2,3,6-tetrahydropyridin-4-yl]-7H-pyrrolo[2,3-d]pyrimidine;

4-(5-butoxy-2-fluorophenyl)-6-[1-(methylsulfonyl)-1,2,3,6-tetrahydropyridin-4-yl]-7H-pyrrolo[2,3-d]pyrimidine;

4-(2-fluoro-3-methoxyphenyl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[3-(trifluoromethoxy)phenyl]-7H-pyrrolo[2,3-d]pyrimidine;

4-(1-methyl-1H-pyrazol-4-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-[2-(trifluoromethoxy)phenyl]-7H-pyrrolo[2,3-d]pyrimidine;

4-(4-methoxypyridin-3-yl)-6-[1-(methylsulfonyl)-1,2,3,6-tetrahydropyridin-4-yl]-7H-pyrrolo[2,3-d]pyrimidine;

6-[1-(methylsulfonyl)-1,2,3,6-tetrahydropyridin-4-yl]-4-(morpholin-4-yl)-7H-pyrrolo[2,3-d]pyrimidine;

6-(4,4-difluorocyclohex-1-en-1-yl)-4-(5-fluoro-2-methoxyphenyl)-7H-pyrrolo[2,3-d]pyrimidine;

6-[1-(methylsulfonyl)-1,2,3,6-tetrahydropyridin-4-yl]-4-(pyrrolidin-1-yl)-7H-pyrrolo[2,3-d]pyrimidine;

4-(4,4-difluoropiperidin-1-yl)-6-[1-(methylsulfonyl)-1,2,3,6-tetrahydropyridin-4-yl]-7H-pyrrolo[2,3-d]pyrimidine;

4-(3,3-difluoroazetidin-1-yl)-6-[1-(methylsulfonyl)-1,2,3,6-tetrahydropyridin-4-yl]-7H-pyrrolo[2,3-d]pyrimidine;

6-(3,6-dihydro-2H-pyran-4-yl)-4-(5-fluoro-2-methoxyphenyl)-7H-pyrrolo[2,3-d]pyrimidine;

tert-butyl 4-[4-(2-ethoxy-5-fluorophenyl)-7H-pyrrolo[2,3-d]pyrimidin-6-yl]-3,6-dihydropyridine-1(2H)-carboxylate;

4-(2-ethoxy-5-fluorophenyl)-6-(1,2,3,6-tetrahydropyridin-4-yl)-7H-pyrrolo[2,3-d]pyrimidine;

N-[4-({4-[4-(2-ethoxy-5-fluorophenyl)-7H-pyrrolo[2,3-d]pyrimidin-6-yl]-3,6-dihydropyridin-1(2H)-yl}methyl)phenyl]acetamide;

tert-butyl [4-({4-[4-(5-fluoro-2-methoxyphenyl)-7H-pyrrolo[2,3-d]pyrimidin-6-yl]-3,6-dihydropyridin-1(2H)-yl}methyl)phenyl]carbamate;

4-({4-[4-(5-fluoro-2-methoxyphenyl)-7H-pyrrolo[2,3-d]pyrimidin-6-yl]-3,6-dihydropyridin-1(2H)-yl}methyl)aniline;

methyl 4-({4-[4-(5-fluoro-2-methoxyphenyl)-7H-pyrrolo[2,3-d]pyrimidin-6-yl]-3,6-dihydropyridin-1(2H)-yl}methyl)benzoate;

4-({4-[4-(5-fluoro-2-methoxyphenyl)-7H-pyrrolo[2,3-d]pyrimidin-6-yl]-3,6-dihydropyridin-1(2H)-yl}methyl)benzoic acid;

methyl trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylate;

trans-4-({4-[4-(5-fluoro-2-methoxyphenyl)-7H-pyrrolo[2,3-d]pyrimidin-6-yl]-3,6-dihydropyridin-1(2H)-yl}carbonyl)cyclohexanecarboxylic acid;

4-[4-(5-fluoro-2-methoxyphenyl)-7H-pyrrolo[2,3-d]pyrimidin-6-yl]-N,N-dimethyl-3,6-dihydropyridine-1(2H)-carboxamide;

4-[4-(2,3-difluorophenyl)-7H-pyrrolo[2,3-d]pyrimidin-6-yl]-N,N-dimethyl-3,6-dihydropyridine-1(2H)-carboxamide;

(2S)-cyclohexyl({4-[4-(5-fluoro-2-methoxyphenyl)-7H-pyrrolo[2,3-d]pyrimidin-6-yl]cyclohex-3-en-1-yl}amino)acetic acid;

N-{4-[4-(5-fluoro-2-methoxyphenyl)-7H-pyrrolo[2,3-d]pyrimidin-6-yl]cyclohex-3-en-1-yl}-L-valine;

4-[4-(5-fluoro-2-methoxyphenyl)-7H-pyrrolo[2,3-d]pyrimidin-6-yl]cyclohex-3-ene-1-carboxylic acid;

2-{4-[4-(5-fluoro-2-methoxyphenyl)-7H-pyrrolo[2,3-d]pyrimidin-6-yl]-3,6-dihydropyridin-1(2H)-yl}-N,N-dimethylacetamide;

N-[4-({4-[4-(5-fluoro-2-methoxyphenyl)-7H-pyrrolo[2,3-d]pyrimidin-6-yl]-3,6-dihydropyridin-1(2H)-yl}methyl)phenyl]methanesulfonamide;

ethyl ({4-[4-(5-fluoro-2-methoxyphenyl)-7H-pyrrolo[2,3-d]pyrimidin-6-yl]-3,6-dihydropyridin-1(2H)-yl}sulfonyl)carbamate;

N-{4-[4-(5-fluoro-2-methoxyphenyl)-7H-pyrrolo[2,3-d]pyrimidin-6-yl]cyclohex-3-en-1-yl}-3-methyl-L-valine;

N-{4-[4-(5-fluoro-2-methoxyphenyl)-7H-pyrrolo[2,3-d]pyrimidin-6-yl]cyclohex-3-en-1-yl}-D-valine;

N-{4-[4-(5-fluoro-2-methoxyphenyl)-7H-pyrrolo[2,3-d]pyrimidin-6-yl]cyclohex-3-en-1-yl}-L-leucine;

4-{4-[4-(5-fluoro-2-methoxyphenyl)-7H-pyrrolo[2,3-d]pyrimidin-6-yl]-3,6-dihydropyridin-1(2H)-yl}cyclohexanecarboxylic acid;

(trans-4-{4-[4-(5-fluoro-2-methoxyphenyl)-7H-pyrrolo[2,3-d]pyrimidin-6-yl]-3,6-dihydropyridin-1(2H)-yl}cyclohexyl)acetic acid; and pharmaceutically acceptable salts thereof.

* * * * *